(12) United States Patent
Mercanzini

(10) Patent No.: US 9,889,304 B2
(45) Date of Patent: *Feb. 13, 2018

(54) LEADLESS NEUROSTIMULATOR

(71) Applicant: ALEVA NEUROTHERAPEUTICS, Lausanne (CH)

(72) Inventor: Andre Mercanzini, Saint Sulpice (CH)

(73) Assignee: ALEVA NEUROTHERAPEUTICS, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/426,816

(22) Filed: Feb. 7, 2017

(65) Prior Publication Data

US 2017/0143982 A1    May 25, 2017

Related U.S. Application Data

(60) Continuation of application No. 15/194,033, filed on Jun. 27, 2016, now Pat. No. 9,572,985, which is a division of application No. 14/470,356, filed on Aug. 27, 2014, now Pat. No. 9,403,011.

(51) Int. Cl.
| | |
|---|---|
| *A61N 1/37* | (2006.01) |
| *A61N 1/372* | (2006.01) |
| *A61N 1/378* | (2006.01) |
| *A61N 1/05* | (2006.01) |
| *A61N 1/36* | (2006.01) |
| *A61N 1/375* | (2006.01) |

(52) U.S. Cl.
CPC ....... *A61N 1/37229* (2013.01); *A61N 1/0534* (2013.01); *A61N 1/36125* (2013.01); *A61N 1/36135* (2013.01); *A61N 1/3756* (2013.01); *A61N 1/3787* (2013.01); *A61N 1/37205* (2013.01)

(58) Field of Classification Search
CPC .............. A61N 1/37229; A61N 1/0534; A61N 1/36125; A61N 1/37205; A61N 1/3756; A61N 1/3787
USPC ........................................................... 607/45
See application file for complete search history.

(56) References Cited

U.S. PATENT DOCUMENTS

| | | | |
|---|---|---|---|
| 4,245,645 A | 1/1981 | Arseneault et al. | |
| 4,550,733 A | 11/1985 | Liss et al. | |
| 4,837,049 A | 6/1989 | Byers et al. | |

(Continued)

FOREIGN PATENT DOCUMENTS

| | | |
|---|---|---|
| EP | 0 677 743 | 10/1995 |
| EP | 0 743 839 | 11/1996 |

(Continued)

OTHER PUBLICATIONS

US 8,388,533, 03/2013, Hafezi et al. (withdrawn)

(Continued)

*Primary Examiner* — Paula J Stice
(74) *Attorney, Agent, or Firm* — Foley & Lardner LLP; James De Vellis

(57) ABSTRACT

The present disclosure describes a medical device to provide neurostimulation therapy to a patient's brain. The device can be surgically implanted and can remain in the patient until end of life. The present disclosure also describes accessories which guide the implantation of the device, and the components that form a leadless stimulator implantation kit.

20 Claims, 55 Drawing Sheets

(56) References Cited

U.S. PATENT DOCUMENTS

| | | |
|---|---|---|
| 4,917,093 A | 4/1990 | Dufresne et al. |
| 4,928,297 A | 5/1990 | Tsutsui et al. |
| 4,969,468 A | 11/1990 | Byers et al. |
| 4,989,617 A | 2/1991 | Memberg et al. |
| 5,215,088 A | 6/1993 | Normann et al. |
| 5,345,936 A | 9/1994 | Pomeranz et al. |
| 5,391,250 A | 2/1995 | Cheney et al. |
| 5,400,784 A | 3/1995 | Durand et al. |
| 5,419,777 A | 5/1995 | Hofling |
| 5,496,369 A | 3/1996 | Howard, III |
| 5,524,338 A | 6/1996 | Martyniuk et al. |
| 5,628,317 A | 5/1997 | Starkebaum et al. |
| 5,643,330 A | 7/1997 | Holsheimer et al. |
| 5,679,355 A | 10/1997 | Alexander et al. |
| 5,683,422 A | 11/1997 | Rise |
| 5,697,651 A | 12/1997 | Fernandes |
| 5,697,975 A | 12/1997 | Howard et al. |
| 5,702,429 A | 12/1997 | King |
| 5,713,922 A | 2/1998 | King |
| 5,713,923 A | 2/1998 | Ward et al. |
| 5,716,377 A | 2/1998 | Rise et al. |
| 5,727,552 A | 3/1998 | Ryan |
| 5,752,979 A | 5/1998 | Benabid |
| 5,755,759 A | 5/1998 | Cogan |
| 5,782,798 A | 7/1998 | Rise |
| 5,797,970 A | 8/1998 | Pouvreau |
| 5,800,474 A | 9/1998 | Benabid et al. |
| 5,800,535 A | 9/1998 | Howard, III |
| 5,814,092 A | 9/1998 | King |
| 5,824,029 A | 10/1998 | Weijand et al. |
| 5,792,186 A | 11/1998 | Rise |
| 5,833,709 A | 11/1998 | Rise et al. |
| 5,833,714 A | 11/1998 | Loeb |
| 5,843,148 A | 12/1998 | Gijsbers et al. |
| 5,893,883 A | 4/1999 | Torgerson et al. |
| 5,913,882 A | 6/1999 | King |
| 5,921,924 A | 7/1999 | Avitall |
| 5,927,277 A | 7/1999 | Baudino et al. |
| 5,941,906 A | 8/1999 | Barreras et al. |
| 5,957,958 A | 9/1999 | Schulman et al. |
| 5,975,085 A | 11/1999 | Rise |
| 5,978,702 A | 11/1999 | Ward et al. |
| 5,991,668 A | 11/1999 | Leinders et al. |
| 6,011,996 A | 1/2000 | Gielen et al. |
| 6,018,682 A | 1/2000 | Rise |
| 6,024,095 A | 2/2000 | Stanley, III |
| 6,033,403 A | 3/2000 | Tu et al. |
| 6,038,480 A | 3/2000 | Hrdlicka et al. |
| 6,050,992 A | 4/2000 | Nichols |
| 6,094,598 A | 7/2000 | Elsberry et al. |
| 6,104,960 A | 8/2000 | Duysens et al. |
| 6,109,269 A | 8/2000 | Rise et al. |
| 6,125,300 A | 9/2000 | Weijand et al. |
| 6,128,537 A | 10/2000 | Rise |
| 6,129,685 A | 10/2000 | Howard, III |
| 6,161,047 A | 12/2000 | King et al. |
| 6,205,359 B1 | 3/2001 | Boveja |
| 6,205,361 B1 | 3/2001 | Kuzma et al. |
| 6,216,043 B1 | 4/2001 | Swanson et al. |
| 6,227,203 B1 | 5/2001 | Rise et al. |
| 6,253,109 B1 | 6/2001 | Gielen |
| 6,253,110 B1 | 6/2001 | Brabec et al. |
| 6,263,237 B1 | 7/2001 | Rise |
| 6,266,564 B1 | 7/2001 | Hill et al. |
| 6,295,476 B1 | 9/2001 | Schaenzer |
| 6,319,241 B1 | 11/2001 | King et al. |
| 6,330,466 B1 | 12/2001 | Hofmann et al. |
| 6,337,997 B1 | 1/2002 | Rise |
| 6,343,226 B1 | 1/2002 | Sunde et al. |
| 6,353,762 B1 | 3/2002 | Baudino et al. |
| 6,356,784 B1 | 3/2002 | Lozano et al. |
| 6,356,786 B1 | 3/2002 | Rezai et al. |
| 6,356,787 B1 | 3/2002 | Rezai et al. |
| 6,364,875 B1 | 4/2002 | Stanley, III |
| 6,366,813 B1 | 4/2002 | Dilorenzo |
| 6,374,140 B1 | 4/2002 | Rise |
| 6,375,666 B1 | 4/2002 | Mische |
| 6,379,353 B1 | 4/2002 | Nichols |
| 6,415,187 B1 | 7/2002 | Kuzma et al. |
| 6,434,431 B1 | 8/2002 | Camps et al. |
| 6,479,999 B1 | 11/2002 | Demeester et al. |
| 6,484,059 B2 | 11/2002 | Gielen |
| 6,493,590 B1 | 12/2002 | Wessman et al. |
| 6,529,774 B1 | 3/2003 | Greene |
| 6,538,443 B2 | 3/2003 | Morich et al. |
| 6,549,812 B1 | 4/2003 | Smits |
| 6,556,873 B1 | 4/2003 | Smits |
| 6,560,472 B2 | 5/2003 | Hill et al. |
| 6,560,486 B1 | 5/2003 | Osorio et al. |
| 6,587,733 B1 | 7/2003 | Cross et al. |
| 6,591,128 B1 | 7/2003 | Wu et al. |
| 6,594,524 B2 | 7/2003 | Esteller et al. |
| 6,597,953 B2 | 7/2003 | Boling |
| 6,643,552 B2 | 11/2003 | Edell et al. |
| 6,671,544 B2 | 12/2003 | Baudino |
| 6,675,046 B2 | 1/2004 | Holsheimer |
| 6,687,538 B1 | 2/2004 | Hrdlicka et al. |
| 6,690,973 B2 | 2/2004 | Hill et al. |
| 6,708,064 B2 | 3/2004 | Rezai |
| 6,718,208 B2 | 4/2004 | Hill et al. |
| 6,718,211 B2 | 4/2004 | Smits |
| 6,741,893 B2 | 5/2004 | Smits |
| 6,745,079 B2 | 6/2004 | King |
| 6,757,970 B1 | 7/2004 | Kuzma et al. |
| 6,795,737 B2 | 9/2004 | Gielen et al. |
| 6,804,552 B2 | 10/2004 | Thompson et al. |
| 6,818,396 B1 | 11/2004 | Bloch et al. |
| 6,829,498 B2 | 12/2004 | Kipke et al. |
| 6,850,802 B2 | 2/2005 | Holsheimer |
| 6,871,098 B2 | 3/2005 | Nuttin et al. |
| 6,882,881 B1 | 4/2005 | Lesser et al. |
| 6,892,097 B2 | 5/2005 | Holsheimer |
| 6,892,438 B1 | 5/2005 | Hill et al. |
| 6,904,306 B1 | 6/2005 | Wu et al. |
| 6,909,920 B2 | 6/2005 | Lokhoff et al. |
| 6,920,359 B2 | 7/2005 | Meadows et al. |
| 6,928,320 B2 | 8/2005 | King |
| 6,950,706 B2 | 9/2005 | Rodriguez et al. |
| 6,950,709 B2 | 9/2005 | Baudino |
| 6,978,171 B2 | 12/2005 | Goetz et al. |
| 6,978,178 B2 | 12/2005 | Sommer et al. |
| 6,999,819 B2 | 2/2006 | Swoyer et al. |
| 7,006,859 B1 | 2/2006 | Osorio et al. |
| 7,010,351 B2 | 3/2006 | Firlik et al. |
| 7,010,356 B2 | 3/2006 | Jog et al. |
| 7,024,246 B2 | 4/2006 | Acosta et al. |
| 7,035,690 B2 | 4/2006 | Goetz |
| 7,047,082 B1 | 5/2006 | Schrom et al. |
| 7,047,084 B2 | 5/2006 | Erickson et al. |
| 7,050,856 B2 | 5/2006 | Stypulkowski |
| 7,051,419 B2 | 5/2006 | Schrom et al. |
| 7,061,240 B2 | 6/2006 | Ham et al. |
| 7,063,767 B1 | 6/2006 | Tyson et al. |
| 7,076,292 B2 | 7/2006 | Forsberg |
| 7,077,822 B1 | 7/2006 | Howard, III |
| 7,107,104 B2 | 9/2006 | Keravel et al. |
| 7,133,718 B2 | 11/2006 | Bakken et al. |
| 7,146,222 B2 | 12/2006 | Boling |
| 7,151,961 B1 | 12/2006 | Whitehurst et al. |
| 7,174,219 B2 | 2/2007 | Wahlstrand et al. |
| 7,177,701 B1 | 2/2007 | Pianca |
| 7,181,288 B1 | 2/2007 | Rezai et al. |
| 7,184,829 B2 | 2/2007 | Hill et al. |
| 7,187,978 B2 | 3/2007 | Malek et al. |
| 7,191,016 B2 | 3/2007 | Marshall et al. |
| 7,191,018 B2 | 3/2007 | Gielen et al. |
| 7,200,439 B2 | 4/2007 | Zdeblick et al. |
| 7,203,548 B2 | 4/2007 | Whitehurst et al. |
| 7,204,798 B2 | 4/2007 | Zdeblick et al. |
| 7,204,833 B1 | 4/2007 | Osorio et al. |
| 7,209,787 B2 | 4/2007 | Dilorenzo |
| 7,212,851 B2 | 5/2007 | Donoghue et al. |
| 7,212,867 B2 | 5/2007 | Van Venrooij et al. |
| 7,214,189 B2 | 5/2007 | Zdeblick |

(56) References Cited

U.S. PATENT DOCUMENTS

| | | |
|---|---|---|
| 7,216,000 B2 | 5/2007 | Sieracki et al. |
| 7,216,001 B2 | 5/2007 | Hacker et al. |
| 7,231,256 B2 | 6/2007 | Wahlstrand et al. |
| 7,236,822 B2 | 6/2007 | Dobak, III |
| 7,242,984 B2 | 7/2007 | Dilorenzo |
| 7,276,061 B2 | 10/2007 | Schaer et al. |
| 7,280,867 B2 | 10/2007 | Frei et al. |
| 7,282,030 B2 | 10/2007 | Frei et al. |
| 7,282,050 B2 | 10/2007 | Starkebaum et al. |
| 7,286,878 B2 | 10/2007 | Stypulkowski |
| 7,286,882 B2 | 10/2007 | Cole |
| 7,288,066 B2 | 10/2007 | Drew |
| 7,289,851 B2 | 10/2007 | Gunderson et al. |
| 7,289,852 B2 | 10/2007 | Helfinstine et al. |
| 7,295,880 B2 | 11/2007 | Gielen |
| 7,298,143 B2 | 11/2007 | Jaermann et al. |
| 7,307,223 B2 | 12/2007 | Tyson et al. |
| 7,313,430 B2 | 12/2007 | Urquhart et al. |
| 7,313,440 B2 | 12/2007 | Miesel |
| 7,315,759 B2 | 1/2008 | Markowitz et al. |
| 7,317,947 B2 | 1/2008 | Wahlstrand et al. |
| 7,317,948 B1 | 1/2008 | King et al. |
| 7,319,899 B2 | 1/2008 | Keizer |
| 7,319,904 B2 | 1/2008 | Cross et al. |
| 7,321,798 B2 | 1/2008 | Muhlenberg et al. |
| 7,321,837 B2 | 1/2008 | Osorio et al. |
| 7,322,832 B2 | 1/2008 | Kronich et al. |
| 7,328,057 B2 | 2/2008 | Freas et al. |
| 7,328,068 B2 | 2/2008 | Spinelli et al. |
| 7,328,069 B2 | 2/2008 | Gerber |
| 7,330,760 B2 | 2/2008 | Heruth et al. |
| 7,337,010 B2 | 2/2008 | Howard et al. |
| 7,343,206 B2 | 3/2008 | Sage et al. |
| 7,346,395 B2 | 3/2008 | Lozano et al. |
| 7,356,369 B2 | 4/2008 | Phillips et al. |
| 7,359,837 B2 | 4/2008 | Drew |
| 7,366,572 B2 | 4/2008 | Heruth et al. |
| 7,367,956 B2 | 5/2008 | King |
| 7,369,891 B2 | 5/2008 | Augustijn et al. |
| 7,369,893 B2 | 5/2008 | Gunderson |
| 7,369,894 B2 | 5/2008 | Gerber |
| 7,385,443 B1 | 6/2008 | Denison |
| 7,388,378 B2 | 6/2008 | Gray et al. |
| 7,389,147 B2 | 6/2008 | Wahlstrand et al. |
| 7,390,311 B2 | 6/2008 | Hildebrand et al. |
| 7,391,257 B1 | 6/2008 | Denison et al. |
| 7,392,089 B2 | 6/2008 | Wahlstrand et al. |
| 7,395,113 B2 | 7/2008 | Heruth et al. |
| 7,400,927 B1 | 7/2008 | Litvin |
| 7,406,351 B2 | 7/2008 | Wesselink |
| 7,418,292 B2 | 8/2008 | Shafer |
| 7,421,297 B2 | 9/2008 | Giftakis et al. |
| 7,427,280 B2 | 9/2008 | Gerber |
| 7,429,938 B1 | 9/2008 | Corndorf |
| 7,433,734 B2 | 10/2008 | King |
| 7,442,183 B2 | 10/2008 | Baudino et al. |
| 7,447,545 B2 | 11/2008 | Heruth et al. |
| 7,450,996 B2 | 11/2008 | MacDonald et al. |
| 7,463,917 B2 | 12/2008 | Martinez |
| 7,463,928 B2 | 12/2008 | Lee et al. |
| 7,474,247 B1 | 1/2009 | Heinks et al. |
| 7,479,910 B1 | 1/2009 | Heinks et al. |
| 7,483,748 B2 | 1/2009 | Torgerson et al. |
| 7,489,966 B2 | 2/2009 | Leinders et al. |
| 7,489,970 B2 | 2/2009 | Lee et al. |
| 7,491,181 B2 | 2/2009 | Heruth et al. |
| 7,497,844 B2 | 3/2009 | Spear et al. |
| 7,497,863 B2 | 3/2009 | Solar et al. |
| 7,502,217 B2 | 3/2009 | Zhao et al. |
| 7,505,815 B2 | 3/2009 | Lee et al. |
| 7,505,869 B2 | 3/2009 | Hartlaub |
| 7,515,961 B2 | 4/2009 | Germanson et al. |
| 7,519,431 B2 | 4/2009 | Goetz et al. |
| 7,519,432 B2 | 4/2009 | Bolea et al. |
| 7,520,890 B2 | 4/2009 | Phillips |
| 7,526,339 B2 | 4/2009 | Lahti et al. |
| 7,526,340 B2 | 4/2009 | Drew |
| 7,526,341 B2 | 4/2009 | Goetz et al. |
| 7,529,582 B1 | 5/2009 | Dilorenzo |
| 7,529,586 B2 | 5/2009 | Wahlstrand et al. |
| 7,542,803 B2 | 6/2009 | Heruth et al. |
| 7,546,164 B2 | 6/2009 | King |
| 7,546,166 B2 | 6/2009 | Michels et al. |
| 7,548,775 B2 | 6/2009 | Kipke et al. |
| 7,548,786 B2 | 6/2009 | Lee et al. |
| 7,551,951 B1 | 6/2009 | Osorio et al. |
| 7,551,960 B1 | 6/2009 | Forsberg et al. |
| 7,555,345 B2 | 6/2009 | Wahlstrand et al. |
| 7,561,921 B2 | 7/2009 | Phillips et al. |
| 7,563,141 B2 | 7/2009 | Alexander et al. |
| 7,563,541 B2 | 7/2009 | Howard et al. |
| 7,578,819 B2 | 8/2009 | Bleich et al. |
| 7,580,756 B2 | 8/2009 | Schulte et al. |
| 7,582,387 B2 | 9/2009 | Howard et al. |
| 7,590,451 B2 | 9/2009 | Tronnes et al. |
| 7,590,453 B2 | 9/2009 | Heruth et al. |
| 7,590,455 B2 | 9/2009 | Heruth et al. |
| 7,591,970 B2 | 9/2009 | Olson |
| 7,594,828 B2 | 9/2009 | Alexander et al. |
| 7,594,889 B2 | 9/2009 | St. Ores et al. |
| 7,596,399 B2 | 9/2009 | Singhal et al. |
| 7,596,408 B2 | 9/2009 | Singhal et al. |
| 7,596,415 B2 | 9/2009 | Brabec et al. |
| 7,599,730 B2 | 10/2009 | Hunter et al. |
| 7,603,161 B2 | 10/2009 | Wurmfeld et al. |
| 7,603,177 B2 | 10/2009 | Sieracki et al. |
| 7,604,629 B2 | 10/2009 | Gerber et al. |
| 7,604,644 B2 | 10/2009 | Schulte et al. |
| 7,608,458 B2 | 10/2009 | Soykan et al. |
| 7,610,083 B2 | 10/2009 | Drew et al. |
| 7,611,483 B2 | 11/2009 | Gerber et al. |
| 7,614,743 B2 | 11/2009 | Geiger |
| 7,615,015 B2 | 11/2009 | Coleman |
| 7,616,998 B2 | 11/2009 | Nuttin et al. |
| 7,617,002 B2 | 11/2009 | Goetz |
| 7,620,454 B2 | 11/2009 | Dinsmoor et al. |
| 7,622,303 B2 | 11/2009 | Soykan et al. |
| 7,622,988 B2 | 11/2009 | Denison et al. |
| 7,623,053 B2 | 11/2009 | Terry et al. |
| 7,623,918 B2 | 11/2009 | Goetz |
| 7,623,919 B2 | 11/2009 | Goetz et al. |
| 7,623,923 B2 | 11/2009 | Gerber et al. |
| 7,623,930 B2 | 11/2009 | Zeijlemaker et al. |
| 7,624,293 B2 | 11/2009 | Osorio et al. |
| 7,628,780 B2 | 12/2009 | Bonner et al. |
| 7,631,415 B2 | 12/2009 | Phillips et al. |
| 7,632,225 B2 | 12/2009 | Stypulkowski |
| 7,635,541 B2 | 12/2009 | Scott et al. |
| 7,637,867 B2 | 12/2009 | Zdeblick |
| 7,640,059 B2 | 12/2009 | Forsberg et al. |
| 7,640,060 B2 | 12/2009 | Zdeblick |
| 7,641,992 B2 | 1/2010 | Howard et al. |
| 7,642,013 B2 | 1/2010 | Howard et al. |
| 7,647,111 B2 | 1/2010 | Ries et al. |
| 7,647,116 B2 | 1/2010 | Bauhahn |
| 7,647,117 B2 | 1/2010 | Bauhahn |
| 7,647,121 B2 | 1/2010 | Wahlstrand et al. |
| 7,650,291 B2 | 1/2010 | Rosenfeld et al. |
| 7,653,433 B2 | 1/2010 | Lozano et al. |
| 7,657,318 B2 | 2/2010 | King et al. |
| 7,657,319 B2 | 2/2010 | Goetz et al. |
| 7,660,620 B2 | 2/2010 | Zeijlemaker et al. |
| 7,660,630 B2 | 2/2010 | Dudding et al. |
| 7,662,140 B2 | 2/2010 | Heruth et al. |
| 7,662,509 B2 | 2/2010 | Howard et al. |
| 7,663,066 B2 | 2/2010 | Tyson et al. |
| 7,664,551 B2 | 2/2010 | Cigaina |
| 7,664,552 B2 | 2/2010 | Wahlstrand et al. |
| 7,668,601 B2 | 2/2010 | Hegland et al. |
| 7,671,594 B2 | 3/2010 | Gray |
| 7,676,271 B2 | 3/2010 | Wahlstrand et al. |
| 7,676,273 B2 | 3/2010 | Goetz et al. |
| 7,676,274 B2 | 3/2010 | Hung et al. |
| 7,680,540 B2 | 3/2010 | Jensen et al. |

(56) References Cited

U.S. PATENT DOCUMENTS

| | | |
|---|---|---|
| 7,682,355 B2 | 3/2010 | Gerber et al. |
| 7,682,745 B2 | 3/2010 | Howard et al. |
| 7,684,860 B2 | 3/2010 | Wahlstrand et al. |
| 7,684,873 B2 | 3/2010 | Gerber |
| 7,689,289 B2 | 3/2010 | King |
| 7,697,972 B2 | 4/2010 | Verard et al. |
| 7,697,995 B2 | 4/2010 | Cross et al. |
| 7,706,124 B2 | 4/2010 | Zhao et al. |
| 7,706,889 B2 | 4/2010 | Gerber et al. |
| 7,711,421 B2 | 5/2010 | Shafer et al. |
| 7,711,428 B2 | 5/2010 | Janzig et al. |
| 7,711,436 B2 | 5/2010 | Stone |
| 7,713,194 B2 | 5/2010 | Zdeblick |
| 7,713,195 B2 | 5/2010 | Zdeblick |
| 7,720,548 B2 | 5/2010 | King |
| 7,729,768 B2 | 6/2010 | White et al. |
| 7,729,780 B2 | 6/2010 | Vardiman |
| 7,738,958 B2 | 6/2010 | Zdeblick et al. |
| 7,742,823 B2 | 6/2010 | King et al. |
| 7,756,588 B2 | 7/2010 | Jog et al. |
| 7,797,029 B2 | 9/2010 | Gibson et al. |
| 7,822,483 B2 | 10/2010 | Stone et al. |
| 7,853,303 B2 | 12/2010 | Nikumb et al. |
| 7,877,149 B2 | 1/2011 | Zdeblick |
| 7,899,539 B2 | 3/2011 | Whitehurst et al. |
| 7,925,329 B2 | 4/2011 | Zdeblick et al. |
| 7,930,035 B2 | 4/2011 | Dilorenzo |
| 7,935,056 B2 | 5/2011 | Zdeblick |
| 7,941,202 B2 | 5/2011 | Hetke et al. |
| 7,945,336 B2 | 5/2011 | Sauter-Starace et al. |
| 7,969,161 B2 | 6/2011 | Behzadi et al. |
| 7,974,705 B2 | 7/2011 | Zdeblick et al. |
| 7,978,064 B2 | 7/2011 | Zdeblick et al. |
| 7,979,105 B2 | 7/2011 | Kipke et al. |
| 7,983,751 B2 | 7/2011 | Zdeblick et al. |
| 8,000,794 B2 | 8/2011 | Lozano |
| 8,000,808 B2 | 8/2011 | Hegland et al. |
| 8,032,224 B2 | 10/2011 | Miesel et al. |
| 8,036,737 B2 | 10/2011 | Goetz et al. |
| 8,036,743 B2 | 10/2011 | Savage et al. |
| 8,036,748 B2 | 10/2011 | Zdeblick et al. |
| 8,055,334 B2 | 11/2011 | Savage et al. |
| 8,055,353 B2 | 11/2011 | Kreidler et al. |
| 8,099,170 B2 | 1/2012 | Jensen et al. |
| 8,114,021 B2 | 2/2012 | Robertson et al. |
| 8,115,618 B2 | 2/2012 | Robertson et al. |
| 8,121,687 B2 | 2/2012 | Jensen et al. |
| 8,123,684 B2 | 2/2012 | Zdeblick |
| 8,172,762 B2 | 5/2012 | Robertson |
| 8,187,161 B2 | 5/2012 | Li et al. |
| 8,195,308 B2 | 6/2012 | Frank et al. |
| 8,204,586 B2 | 6/2012 | Zdeblick |
| 8,258,962 B2 | 9/2012 | Robertson et al. |
| 8,261,428 B2 | 9/2012 | Fang et al. |
| 8,280,514 B2 | 10/2012 | Lozano et al. |
| 8,332,020 B2 | 12/2012 | Zdeblick |
| 8,355,768 B2 | 1/2013 | Masmanidis et al. |
| 8,412,347 B2 | 4/2013 | Zdeblick |
| 8,473,061 B2 | 6/2013 | Moffitt et al. |
| 8,473,069 B2 | 6/2013 | Bi et al. |
| 8,489,203 B2 | 7/2013 | Ortmann |
| 8,788,064 B2 | 7/2014 | Mercanzini et al. |
| 8,874,232 B2 | 10/2014 | Chen |
| 8,897,891 B2 | 11/2014 | Romero |
| 8,938,308 B2 | 1/2015 | Meadows |
| 9,403,011 B2 * | 8/2016 | Mercanzini ........ A61N 1/3756 |
| 9,474,894 B2 | 10/2016 | Mercanzini et al. |
| 2002/0062143 A1 | 5/2002 | Baudino et al. |
| 2003/0004553 A1 | 1/2003 | Grill et al. |
| 2003/0023282 A1 | 1/2003 | Barrett et al. |
| 2003/0036780 A1 | 2/2003 | Barrett et al. |
| 2003/0060822 A1 | 3/2003 | Schaer et al. |
| 2003/0083724 A1 | 5/2003 | Jog et al. |
| 2003/0100823 A1 | 5/2003 | Kipke et al. |
| 2003/0135253 A1 | 7/2003 | Kokones et al. |
| 2003/0176892 A1 | 9/2003 | Shalev |
| 2004/0002635 A1 | 1/2004 | Hargrove et al. |
| 2004/0015205 A1 | 1/2004 | Whitehurst et al. |
| 2004/0039434 A1 | 2/2004 | Schrom et al. |
| 2004/0098074 A1 | 5/2004 | Erickson et al. |
| 2004/0102828 A1 | 5/2004 | Lowry et al. |
| 2004/0122335 A1 | 6/2004 | Sackellares et al. |
| 2004/0133390 A1 | 7/2004 | Osorio et al. |
| 2004/0138517 A1 | 7/2004 | Osorio et al. |
| 2004/0138536 A1 | 7/2004 | Frei et al. |
| 2004/0138720 A1 | 7/2004 | Naisberg et al. |
| 2004/0138722 A1 | 7/2004 | Carroll et al. |
| 2004/0152958 A1 | 8/2004 | Frei et al. |
| 2004/0172089 A1 | 9/2004 | Whitehurst et al. |
| 2004/0193021 A1 | 9/2004 | Zdeblick et al. |
| 2004/0215288 A1 | 10/2004 | Lee et al. |
| 2004/0220637 A1 | 11/2004 | Zdeblick et al. |
| 2004/0225335 A1 | 11/2004 | Whitehurst et al. |
| 2004/0243011 A1 | 12/2004 | Plaza |
| 2004/0249417 A1 | 12/2004 | Ransbury et al. |
| 2004/0254483 A1 | 12/2004 | Zdeblick et al. |
| 2005/0004627 A1 | 1/2005 | Gibson et al. |
| 2005/0008660 A1 | 1/2005 | Kipke et al. |
| 2005/0010261 A1 | 1/2005 | Luders et al. |
| 2005/0021103 A1 | 1/2005 | Dilorenzo |
| 2005/0027284 A1 | 2/2005 | Lozano et al. |
| 2005/0033136 A1 | 2/2005 | Govari et al. |
| 2005/0038489 A1 | 2/2005 | Grill |
| 2005/0049655 A1 | 3/2005 | Boveja et al. |
| 2005/0070971 A1 | 3/2005 | Fowler et al. |
| 2005/0075681 A1 | 4/2005 | Rezai et al. |
| 2005/0113882 A1 | 5/2005 | Cameron et al. |
| 2005/0137647 A1 | 6/2005 | Wallace et al. |
| 2005/0143790 A1 | 6/2005 | Kipke et al. |
| 2005/0154425 A1 | 7/2005 | Boveja et al. |
| 2005/0171558 A1 | 8/2005 | Abovitz et al. |
| 2005/0182455 A1 | 8/2005 | Thrope et al. |
| 2005/0209511 A1 | 9/2005 | Heruth et al. |
| 2005/0209513 A1 | 9/2005 | Heruth et al. |
| 2005/0209643 A1 | 9/2005 | Heruth et al. |
| 2005/0222642 A1 | 10/2005 | Przybyszewski et al. |
| 2005/0240242 A1 | 10/2005 | Dilorenzo |
| 2005/0245988 A1 | 11/2005 | Miesel |
| 2006/0004422 A1 | 1/2006 | De Ridder |
| 2006/0015153 A1 | 1/2006 | Gliner et al. |
| 2006/0030897 A1 | 2/2006 | Gilmer et al. |
| 2006/0041295 A1 | 2/2006 | Osypka |
| 2006/0049957 A1 | 3/2006 | Surgenor et al. |
| 2006/0058588 A1 | 3/2006 | Zdeblick |
| 2006/0058727 A1 | 3/2006 | Bernabei |
| 2006/0058855 A1 | 3/2006 | Gill |
| 2006/0095105 A1 | 5/2006 | Jog et al. |
| 2006/0116581 A1 | 6/2006 | Zdeblick et al. |
| 2006/0129203 A1 | 6/2006 | Garabedian et al. |
| 2006/0135877 A1 | 6/2006 | Giftakis et al. |
| 2006/0149336 A1 | 7/2006 | Meadows |
| 2006/0149337 A1 | 7/2006 | John |
| 2006/0149340 A1 | 7/2006 | Karunasiri |
| 2006/0167497 A1 | 7/2006 | Armstrong et al. |
| 2006/0173263 A1 | 8/2006 | He et al. |
| 2006/0173510 A1 | 8/2006 | Besio et al. |
| 2006/0178709 A1 | 8/2006 | Foster et al. |
| 2006/0195154 A1 | 8/2006 | Jaax et al. |
| 2006/0200206 A1 | 9/2006 | Firlik et al. |
| 2006/0212090 A1 | 9/2006 | Lozano et al. |
| 2006/0241717 A1 | 10/2006 | Whitehurst et al. |
| 2006/0258951 A1 | 11/2006 | Bleich et al. |
| 2006/0264777 A1 | 11/2006 | Drew |
| 2006/0265022 A1 | 11/2006 | John et al. |
| 2006/0276866 A1 | 12/2006 | McCreery |
| 2006/0282014 A1 | 12/2006 | Kipke et al. |
| 2006/0293720 A1 | 12/2006 | Dilorenzo |
| 2006/0293721 A1 | 12/2006 | Tarver et al. |
| 2007/0027498 A1 | 2/2007 | Maschino et al. |
| 2007/0027500 A1 | 2/2007 | Maschino et al. |
| 2007/0027514 A1 | 2/2007 | Gerber |
| 2007/0043268 A1 | 2/2007 | Russell |
| 2007/0060974 A1 | 3/2007 | Lozano |
| 2007/0067002 A1 | 3/2007 | Lozano |

(56) References Cited

U.S. PATENT DOCUMENTS

| | | |
|---|---|---|
| 2007/0067003 A1 | 3/2007 | Sanchez et al. |
| 2007/0088403 A1 | 4/2007 | Wyler et al. |
| 2007/0088404 A1 | 4/2007 | Wyler et al. |
| 2007/0093870 A1 | 4/2007 | Maschino |
| 2007/0100389 A1 | 5/2007 | Jaax et al. |
| 2007/0100392 A1 | 5/2007 | Maschino et al. |
| 2007/0100393 A1 | 5/2007 | Whitehurst et al. |
| 2007/0100398 A1 | 5/2007 | Sloan |
| 2007/0106143 A1 | 5/2007 | Flaherty |
| 2007/0123765 A1 | 5/2007 | Hetke et al. |
| 2007/0123944 A1 | 5/2007 | Zdeblick |
| 2007/0135721 A1 | 6/2007 | Zdeblick |
| 2007/0142872 A1 | 6/2007 | Mickle et al. |
| 2007/0150024 A1 | 6/2007 | Leyde et al. |
| 2007/0173890 A1 | 7/2007 | Armstrong |
| 2007/0173896 A1 | 7/2007 | Zdeblick |
| 2007/0173897 A1 | 7/2007 | Zdeblick |
| 2007/0173901 A1 | 7/2007 | Reeve |
| 2007/0173908 A1 | 7/2007 | Begnaud |
| 2007/0179558 A1 | 8/2007 | Gliner et al. |
| 2007/0179569 A1 | 8/2007 | Zdeblick |
| 2007/0185537 A1 | 8/2007 | Zdeblick |
| 2007/0185544 A1 | 8/2007 | Dawant et al. |
| 2007/0185548 A1 | 8/2007 | Zdeblick |
| 2007/0185549 A1 | 8/2007 | Zdeblick |
| 2007/0197892 A1 | 8/2007 | Shen et al. |
| 2007/0203537 A1 | 8/2007 | Goetz et al. |
| 2007/0203546 A1 | 8/2007 | Stone et al. |
| 2007/0208394 A1 | 9/2007 | King et al. |
| 2007/0213784 A1 | 9/2007 | Pless |
| 2007/0213785 A1 | 9/2007 | Osorio et al. |
| 2007/0213786 A1 | 9/2007 | Sackellares et al. |
| 2007/0219591 A1 | 9/2007 | Zdeblick et al. |
| 2007/0225674 A1 | 9/2007 | Molnar et al. |
| 2007/0225773 A1 | 9/2007 | Shen et al. |
| 2007/0225774 A1 | 9/2007 | Eskandar et al. |
| 2007/0233192 A1 | 10/2007 | Craig |
| 2007/0249953 A1 | 10/2007 | Frei et al. |
| 2007/0249954 A1 | 10/2007 | Virag et al. |
| 2007/0250133 A1 | 10/2007 | Carlson et al. |
| 2007/0255323 A1 | 11/2007 | Werder et al. |
| 2007/0255338 A1 | 11/2007 | Wahlstrand |
| 2007/0255374 A1 | 11/2007 | Kolafa et al. |
| 2007/0255531 A1 | 11/2007 | Drew |
| 2007/0265683 A1 | 11/2007 | Ehrlich |
| 2007/0282389 A1 | 12/2007 | Moxon et al. |
| 2007/0293908 A1 | 12/2007 | Cowan et al. |
| 2008/0021514 A1 | 1/2008 | Pless |
| 2008/0021517 A1 | 1/2008 | Dietrich |
| 2008/0027289 A1 | 1/2008 | Zdeblick |
| 2008/0027487 A1 | 1/2008 | Patel et al. |
| 2008/0027503 A1 | 1/2008 | Marrosu et al. |
| 2008/0027504 A1 | 1/2008 | Bedenbaugh |
| 2008/0027540 A1 | 1/2008 | Cumming |
| 2008/0039895 A1 | 2/2008 | Fowler et al. |
| 2008/0046012 A1 | 2/2008 | Covalin et al. |
| 2008/0046013 A1 | 2/2008 | Lozano |
| 2008/0058630 A1 | 3/2008 | Robertson |
| 2008/0077186 A1 | 3/2008 | Thompson et al. |
| 2008/0077191 A1 | 3/2008 | Morrell |
| 2008/0103547 A1 | 5/2008 | Okun et al. |
| 2008/0103548 A1 | 5/2008 | Fowler et al. |
| 2008/0103578 A1 | 5/2008 | Gerber |
| 2008/0114417 A1 | 5/2008 | Leyde |
| 2008/0119900 A1 | 5/2008 | Dilorenzo |
| 2008/0139870 A1 | 6/2008 | Gliner et al. |
| 2008/0140152 A1 | 6/2008 | Imran et al. |
| 2008/0154328 A1 | 6/2008 | Thompson et al. |
| 2008/0154331 A1 | 6/2008 | John et al. |
| 2008/0161881 A1 | 7/2008 | Firlik et al. |
| 2008/0161896 A1 | 7/2008 | Sauter-Starace et al. |
| 2008/0172103 A1 | 7/2008 | Kao et al. |
| 2008/0177196 A1 | 7/2008 | Burdick et al. |
| 2008/0188905 A1 | 8/2008 | Swartz |
| 2008/0195166 A1 | 8/2008 | Sun et al. |
| 2008/0195227 A1 | 8/2008 | Boling et al. |
| 2008/0208283 A1 | 8/2008 | Vetter et al. |
| 2008/0208287 A1 | 8/2008 | Palermo et al. |
| 2008/0215125 A1 | 9/2008 | Farah et al. |
| 2008/0221642 A1 | 9/2008 | Humayun et al. |
| 2008/0242976 A1 | 10/2008 | Robertson et al. |
| 2008/0255439 A1 | 10/2008 | Tang et al. |
| 2008/0255629 A1 | 10/2008 | Jenson et al. |
| 2008/0255647 A1 | 10/2008 | Jensen et al. |
| 2008/0269835 A1 | 10/2008 | Carlson et al. |
| 2008/0269842 A1 | 10/2008 | Giftakis et al. |
| 2008/0269854 A1 | 10/2008 | Hegland et al. |
| 2008/0275526 A1 | 11/2008 | Lozano |
| 2008/0284599 A1 | 11/2008 | Zdeblick et al. |
| 2008/0294218 A1 | 11/2008 | Savage et al. |
| 2008/0300652 A1 | 12/2008 | Lim et al. |
| 2008/0306394 A1 | 12/2008 | Zdeblick et al. |
| 2008/0312726 A1 | 12/2008 | Frank et al. |
| 2008/0316020 A1 | 12/2008 | Robertson et al. |
| 2009/0027504 A1 | 1/2009 | Lim et al. |
| 2009/0062879 A1 | 3/2009 | Li et al. |
| 2009/0082645 A1 | 3/2009 | Hafezi et al. |
| 2009/0105784 A1 | 4/2009 | Massoud-Ansari et al. |
| 2009/0118806 A1 | 5/2009 | Vetter et al. |
| 2009/0132042 A1 | 5/2009 | Hetke et al. |
| 2009/0171416 A1 | 7/2009 | Firlik et al. |
| 2009/0177144 A1 | 7/2009 | Masmanidis et al. |
| 2009/0187196 A1 | 7/2009 | Vetter |
| 2009/0204183 A1 | 8/2009 | Kreidler et al. |
| 2009/0240314 A1 | 9/2009 | Kong et al. |
| 2009/0253977 A1 | 10/2009 | Kipke et al. |
| 2009/0256702 A1 | 10/2009 | Robertson et al. |
| 2009/0292325 A1 | 11/2009 | Cederna et al. |
| 2009/0299174 A1 | 12/2009 | Wright et al. |
| 2009/0306728 A1 | 12/2009 | Wright et al. |
| 2009/0306729 A1 | 12/2009 | Doerr |
| 2009/0312770 A1 | 12/2009 | Kozai et al. |
| 2009/0318824 A1 | 12/2009 | Nishida et al. |
| 2009/0325424 A1 | 12/2009 | Aarts et al. |
| 2010/0014541 A1 | 1/2010 | Harriman |
| 2010/0015274 A1 | 1/2010 | Fill |
| 2010/0030298 A1 | 2/2010 | Martens et al. |
| 2010/0036468 A1 | 2/2010 | Decre et al. |
| 2010/0069717 A1 | 3/2010 | Hafezi et al. |
| 2010/0076536 A1 | 3/2010 | Merz et al. |
| 2010/0087853 A1 | 4/2010 | Kipke et al. |
| 2010/0100152 A1 | 4/2010 | Martens et al. |
| 2010/0106178 A1 | 4/2010 | Obermiller et al. |
| 2010/0114193 A1 | 5/2010 | Lozano et al. |
| 2010/0114234 A1 | 5/2010 | Zdeblick |
| 2010/0114250 A1 | 5/2010 | Zdeblick |
| 2010/0130844 A1 | 5/2010 | Williams et al. |
| 2010/0145216 A1 | 6/2010 | He et al. |
| 2010/0145414 A1 | 6/2010 | Decre et al. |
| 2010/0152747 A1 | 6/2010 | Padiy et al. |
| 2010/0198315 A1 | 8/2010 | Martens et al. |
| 2010/0249883 A1 | 9/2010 | Zdeblick |
| 2010/0274305 A1 | 10/2010 | Gliner et al. |
| 2010/0292602 A1 | 11/2010 | Worrell et al. |
| 2010/0298908 A1 | 11/2010 | Vardiman |
| 2010/0298917 A1 | 11/2010 | Vardiman |
| 2010/0298918 A1 | 11/2010 | Vardiman |
| 2010/0312188 A1 | 12/2010 | Robertson et al. |
| 2010/0312228 A1 | 12/2010 | Zdeblick et al. |
| 2010/0318163 A1 | 12/2010 | Zdeblick |
| 2010/0331807 A1 | 12/2010 | Whitehurst et al. |
| 2011/0001488 A1 | 1/2011 | Behzadi et al. |
| 2011/0022124 A1 | 1/2011 | Zdeblick et al. |
| 2011/0034964 A1 | 2/2011 | Bi et al. |
| 2011/0034970 A1 | 2/2011 | Barker |
| 2011/0040203 A1 | 2/2011 | Savage et al. |
| 2011/0071766 A1 | 3/2011 | Dolan et al. |
| 2011/0130809 A1 | 6/2011 | Zdeblick |
| 2011/0152988 A1 | 6/2011 | Whitehurst et al. |
| 2011/0154655 A1 | 6/2011 | Hetke et al. |
| 2011/0184495 A1 | 7/2011 | Wang et al. |
| 2011/0190860 A1 | 8/2011 | Harberts et al. |
| 2011/0196454 A1 | 8/2011 | Strand et al. |
| 2011/0208225 A1 | 8/2011 | Martens et al. |

(56) References Cited

U.S. PATENT DOCUMENTS

| | | |
|---|---|---|
| 2011/0213382 A1 | 9/2011 | Decre et al. |
| 2011/0218417 A1 | 9/2011 | Boogaard et al. |
| 2011/0224757 A1 | 9/2011 | Zdeblick et al. |
| 2011/0224765 A1 | 9/2011 | Harberts et al. |
| 2011/0224766 A1 | 9/2011 | Tol et al. |
| 2011/0282179 A1 | 11/2011 | Zdeblick |
| 2011/0301665 A1 | 12/2011 | Mercanzini et al. |
| 2012/0004520 A1 | 1/2012 | Whitworth et al. |
| 2012/0004527 A1 | 1/2012 | Thompson et al. |
| 2012/0004716 A1 | 1/2012 | Langhammer et al. |
| 2012/0007734 A1 | 1/2012 | Berkman et al. |
| 2012/0022341 A1 | 1/2012 | Zdeblick |
| 2012/0035684 A1 | 2/2012 | Thompson et al. |
| 2012/0053344 A1 | 3/2012 | Lagos Gonzalez |
| 2012/0059444 A1 | 3/2012 | Pardoel et al. |
| 2012/0062379 A1 | 3/2012 | Hafezi et al. |
| 2012/0095355 A1 | 4/2012 | Zdeblick |
| 2012/0109262 A1 | 5/2012 | Martens |
| 2012/0109599 A1 | 5/2012 | Martens |
| 2012/0116188 A1 | 5/2012 | Frank et al. |
| 2012/0136420 A1 | 5/2012 | Pardoel et al. |
| 2012/0150256 A1 | 6/2012 | Martens |
| 2012/0184837 A1 | 7/2012 | Martens et al. |
| 2012/0253442 A1 | 10/2012 | Gliner et al. |
| 2012/0277821 A1 | 11/2012 | Martens et al. |
| 2012/0296444 A1 | 11/2012 | Greenberg et al. |
| 2012/0303088 A1 | 11/2012 | Van Kaam et al. |
| 2012/0303089 A1 | 11/2012 | Martens et al. |
| 2012/0303107 A1 | 11/2012 | Decre et al. |
| 2012/0316630 A1 | 12/2012 | Firlik et al. |
| 2013/0009691 A1 | 1/2013 | Blanken et al. |
| 2013/0030366 A1 | 1/2013 | Robertson et al. |
| 2013/0046356 A1 | 2/2013 | Jensen et al. |
| 2013/0060102 A1 | 3/2013 | Zdeblick |
| 2013/0085361 A1 | 4/2013 | Mercanzini et al. |
| 2013/0131754 A1 | 5/2013 | Sarvazyan |
| 2013/0144132 A1 | 6/2013 | Hafezi et al. |
| 2013/0172716 A1 | 7/2013 | Lozano et al. |
| 2013/0193950 A1 | 8/2013 | Hafezi et al. |
| 2013/0204318 A1 | 8/2013 | Young |
| 2013/0223028 A1 | 8/2013 | Arne et al. |
| 2013/0231188 A1 | 9/2013 | Berberich et al. |
| 2013/0282090 A1 | 10/2013 | Decre et al. |
| 2013/0345780 A1 | 12/2013 | Tabada et al. |
| 2013/0345789 A1 | 12/2013 | Havel et al. |
| 2014/0039578 A1 | 2/2014 | Whitehurst et al. |

FOREIGN PATENT DOCUMENTS

| | | |
|---|---|---|
| EP | 0 892 654 | 1/1999 |
| EP | 0 895 483 | 2/1999 |
| EP | 0 959 942 | 12/1999 |
| EP | 1 048 319 | 11/2000 |
| EP | 1 062 973 | 12/2000 |
| EP | 1 102 607 | 5/2001 |
| EP | 1 257 320 | 11/2002 |
| EP | 1 446 189 | 8/2004 |
| EP | 1 514 576 | 3/2005 |
| EP | 1 750 798 | 2/2007 |
| EP | 1 890 764 | 2/2008 |
| EP | 1 931 419 | 6/2008 |
| EP | 1 985 579 | 10/2008 |
| EP | 1 993 665 | 11/2008 |
| EP | 2 046 441 | 4/2009 |
| EP | 2 066 396 B1 | 6/2009 |
| EP | 2 069 003 | 6/2009 |
| EP | 2 131 916 | 12/2009 |
| EP | 2 167 188 | 3/2010 |
| EP | 2 320 221 | 5/2011 |
| EP | 2 341 979 | 7/2011 |
| EP | 2 456 513 A1 | 5/2012 |
| EP | 2 542 303 A1 | 1/2013 |
| EP | 2 559 454 A1 | 2/2013 |
| EP | 2 604 313 | 6/2013 |
| EP | 2 620 179 A1 | 7/2013 |
| EP | 2 623 154 A1 | 8/2013 |
| EP | 2 626 108 A1 | 8/2013 |
| EP | 2 626 109 A1 | 8/2013 |
| EP | 2 626 110 A1 | 8/2013 |
| EP | 2 626 111 A1 | 8/2013 |
| EP | 2 656 875 A1 | 10/2013 |
| EP | 2 656 876 A1 | 10/2013 |
| EP | 2 674 193 A1 | 12/2013 |
| WO | WO-98/10010 | 3/1998 |
| WO | WO-02/068042 | 9/2002 |
| WO | WO-03/022354 | 3/2003 |
| WO | WO-03/028521 | 4/2003 |
| WO | WO-03/066152 | 8/2003 |
| WO | WO-03/066153 A2 | 8/2003 |
| WO | WO-03/066157 | 8/2003 |
| WO | WO-2004/045707 | 6/2004 |
| WO | WO-2005/002467 | 1/2005 |
| WO | WO-2005/067792 | 7/2005 |
| WO | WO-2005/112216 | 11/2005 |
| WO | WO-2006/029257 | 3/2006 |
| WO | WO-2006/047265 | 5/2006 |
| WO | WO-2006/104432 | 10/2006 |
| WO | WO-2007/002144 | 1/2007 |
| WO | WO-2007/009070 | 1/2007 |
| WO | WO-2007/011611 | 1/2007 |
| WO | WO-2007/025356 | 3/2007 |
| WO | WO-2007/028003 A2 | 3/2007 |
| WO | WO-2007/042999 | 4/2007 |
| WO | WO-2007/092330 | 8/2007 |
| WO | WO-2007/100428 | 9/2007 |
| WO | WO-2007/108718 | 9/2007 |
| WO | WO-2008/003318 | 1/2008 |
| WO | WO-2008/005478 | 1/2008 |
| WO | WO-2008/016881 | 2/2008 |
| WO | WO-2008/035285 | 3/2008 |
| WO | WO-2008/035344 | 3/2008 |
| WO | WO-2008/051463 | 5/2008 |
| WO | WO-2008/064269 A2 | 5/2008 |
| WO | WO-2008/068759 | 6/2008 |
| WO | WO-2008/075294 | 6/2008 |
| WO | WO-2008/077440 | 7/2008 |
| WO | WO-2008/089726 | 7/2008 |
| WO | WO-2008/107822 | 9/2008 |
| WO | WO-2008/109298 | 9/2008 |
| WO | WO-2008/133616 | 11/2008 |
| WO | WO-2008/133683 | 11/2008 |
| WO | WO-2008/138305 | 11/2008 |
| WO | WO-2010/014686 | 2/2010 |
| WO | WO-2010/055421 | 5/2010 |
| WO | WO-2011/115999 | 9/2011 |
| WO | WO-2013/014206 | 1/2013 |
| WO | WO-2016/030823 | 3/2016 |

OTHER PUBLICATIONS

US 8,469,885, 06/2013, Hafezi et al. (withdrawn)
U.S. Appl. No. 07/151,961, filed Feb. 3, 1988, Masahiko Okunuki et al.
U.S. Appl. No. 07/184,829.
Australian Patent Examination Report No. 1 dated Jan. 30, 2014 in corresponding Australian Application No. 2010326613, 2 pages.
Australian Patent Examination Report No. 1 dated Jan. 31, 2014 in corresponding Australian Application No. 2009315316, 3 pages.
Benabid, et al. "Combined (Thalamotomy and Stimulation) Stereotactic Surgery of the VIM Thalamic Nucleus for Bilateral Parkinson Disease", Proceedings of the Meeting of the American Society for Stereotactic and Functional Neurosurgery, Montreal 1987 Appl. Neurophysiol. 50: 344-346.
CA Office Action in CA Application No. 2795159 dated Jan. 27, 2017 (4 pages).
CA Office Action on CA Appln. No. 2782710 dated Aug. 14, 2017 (5 pages).
Canadian Office Action for Application No. 2,743,575 dated Sep. 25, 2014, 3 pages.
Cogan, S., et al. "Plasma-enhanced chemical vapor deposited silicon carbide as an implantable dielectric coating." Journal of Biomedical Materials Research Part A 67.3 (2003): 856-867.

(56) References Cited

OTHER PUBLICATIONS

Communication from the European Patent Office in Application No. 09795810.2 dated Sep. 14, 2011.
Decision of Rejection and Decision for Dismissal of Amendment in JP Patent Application No. 2011-543841 dated May 15, 2014.
Decision of Rejection for Japanese Appl. Serial No. 2012-541491 dated Oct. 26, 2015.
EIC Biomedical, "Thin-film Encapsulation for Neural Recording and Stimulation Electrodes", Silicon carbide and oxycarbide, Apr. 2008: pp. 1-2.
English translation of Notice of Reasons for Rejection in JP application No. 2011-543841 dated Oct. 21, 2013.
European Communication and Search Report for Application No. 09795810.2 dated Sep. 25, 2013.
European Communication dated May 22, 2013 including search report for EP application No. 12198290.4-1652.
European Search Report for Appl. Ser. No. 09803534.8 dated Jul. 21, 2011.
European Search Report for Appl. Ser. No. 13169272.5 dated Aug. 30, 2013.
European Search Report for application No. EP 14172592 dated Aug. 28, 2014, 8 pages.
Examination Report for EP09795810.2 dated Jun. 22, 2012.
Examination Report from European Patent Office in 09 795 810.2 dated May 8, 2014.
Examination Report in AU Patent Application No. 2009276603 dated Mar. 3, 2014.
Examination report in AU Patent Application No. 2011234422 dated Feb. 11, 2014.
Examination Report in EP Patent Application No. 11 711 884.4 dated Mar. 28, 2014.
Extended European Search Report on EP Appln. No. 16199868.7 dated Apr. 28, 2017 (7 pages).
Fierce Medical Devices, "Medtronic Announces First U.S. Implant of World's Smallest, Minimally Invasive Cardiac Pacemaker", Feb. 20, 2014, pp. 1-3.
Gibney, "St. Jude places its Nanostim leadless pacemaker in a U.K. patient", Fierce Medical Devices, Jan. 27, 2014, pp. 1-3.
International Preliminary Report on Patentability for PCT/EP2010/068658 dated Jun. 5, 2012.
International Preliminary Report on Patentability for PCT/IB2009/007715 dated May 17, 2011.
International Preliminary Report on Patentability for PCT/IB2015/056437 dated Mar. 9, 2017.
International Preliminary Report on Patentability for PCT/IB2015/056438 dated Mar. 9, 2017.
International Preliminary Report on Patentability for PCT/US2009/052077 dated Feb. 1, 2011.
International Preliminary Report on Patentability on PPCT/IB2015/053610 dated Dec. 1, 2016 (8 pages).
International Search Report and Written Opinion for PCT Appl. Ser. No. PCT/IB2015/053610 dated Jul. 20, 2015.
International Search Report and Written Opinion for PCT Appl. Ser. No. PCT/IB2015/056437 dated Nov. 5, 2015.
International Search Report and Written Opinion for PCT Appl. Ser. No. PCT/IB2015/056438 dated Nov. 5, 2015.
International Search Report and Written Opinion for PCT/EP2010/068658 dated Mar. 21, 2011.
International Search Report and Written Opinion for PCT/IB2017/050551 dated Mar. 29, 2017.
International Search Report and Written Opinion in Application No. PCT/EP2011/055045 dated Jul. 18, 2011.
International Search Report and Written Opinion in PCT/US09/52077 dated Sep. 25, 2009.
International Search Report for PCT/IB2009/007715 dated Apr. 22, 2010.
Notice of Allowance for U.S. Appl. No. 14/287,917 dated Apr. 15, 2015.
Notice of Allowance on U.S. Appl. No. 14/470,423 dated Jun. 15, 2016.
Notice of Allowance on U.S. Appl. No. 14/945,952 dated Dec. 7, 2016.
Notice of Allowance on U.S. Appl. No. 15/194,033 dated Oct. 27, 2016.
Notice of Reasons for Rejection for Japanese Patent Application No. 2011-543841 dated May 30, 2013.
Notice of Reasons for Rejection in JP Patent Application No. 2011-521276 dated Mar. 3, 2014.
Notice of Reasons for Rejection in JP Patent Application No. 2011-521276 dated May 30, 2013.
Notice of Reasons for Rejections for Japanese Patent Appl. Serial No. 2012-541491 dated Aug. 28, 2014, 8 pages.
Office Action for CA 2,732,309 dated Nov. 8, 2016.
Office Action for CA 2,782,710 dated Oct. 19, 2016.
Office Action for Canadian Appl. Ser. No. 2732309 dated Dec. 7, 2015.
Office Action for Canadian Appl. Ser. No. 2743575 dated Jan. 21, 2015 (4 pages).
Office Action for Canadian Appl. Ser. No. 2743575 dated Jun. 11, 2015.
Office Action for Canadian Appl. Ser. No. 2743575 dated Sep. 14, 2015.
Office Action for EPO Appl. Ser. No. 10787404.2 dated May 6, 2015.
Office Action for EPO Appl. Ser. No. 14172592.9 dated Aug. 20, 2015.
Office Action for European Application No. 10787404.2 dated Mar. 26, 2013.
Office Action for Japanese Appl. Ser. No. 2013-501857 dated Jun. 1, 2015.
Office Action for Japanese Appl. Ser. No. 2013-501857 dated Sep. 17, 2014.
Office Action on U.S. Appl. No. 14/731,296 dated Oct. 5, 2016.
Office Action on U.S. Appl. No. 14/945,952 dated Jul. 26, 2016.
Office Action on U.S. Appl. No. 15/194,033 dated Aug. 22, 2016.
Office Action on U.S. Appl. No. 15/281,468 dated Dec. 7, 2016.
Pollak, et al. "Effets de la Stimulation du Noyau Sous-Thalamique Dans La Maladie De Parkinson", Rev. Neurol (Paris),149, 3, 175-176. Mason, Paris, 1993.
Rousche, et al., "Flexible polyimide-based intracortical electrode arrays with bioactive capability," IEEE Transactions on Biomedical Engineering 48(3): 361-371 (Mar. 2001).
Search Report for EP 16190439.6 dated Jul. 27, 2017.
Second Notice of Reasons for Rejection for Japanese Application No. 2012-541491 dated Apr. 8, 2015.
Sepulveda et al., "Finite Element Analysis of Current Pathways with Implanted Electrodes", J. Biomed. Eng. 1983, vol. 5, pp. 41-48.
U.S. Corrected Notice of Allowability for U.S. Appl. No. 14/470,356 dated May 18, 2016.
U.S. Notice of Allowance for U.S. Appl. No. 14/287,917 dated Jul. 20, 2015.
U.S. Notice of Allowance for U.S. Appl. No. 14/309,491 dated May 11, 2016.
U.S. Notice of Allowance for U.S. Appl. No. 14/316,154 dated Apr. 20, 2015.
U.S. Notice of Allowance for U.S. Appl. No. 14/470,356 dated Apr. 13, 2016.
U.S. Notice of Allowance for U.S. Appl. No. 14/470,356 dated Mar. 18, 2016.
U.S. Notice of Allowance for U.S. Appl. No. 13/512,936 dated Feb. 20, 2014.
U.S. Notice of Allowance for U.S. Appl. No. 13/512,936 dated Nov. 25, 2013.
U.S. Notice of Allowance for U.S. Appl. No. 13/056,261 dated May 8, 2014.
U.S. Notice of Allowance in U.S. Appl. No. 13/128,821 dated Dec. 24, 2013.
U.S. Notice of Allowance in U.S. Appl. No. 13/128,821 dated Mar. 25, 2014.
U.S. Notice of Allowance on U.S. Appl. No. 13/638,435 dated Sep. 16, 2016.
U.S. Notice of Allowance on U.S. Appl. No. 15/422,393 dated Jul. 11, 2017.

(56) References Cited

OTHER PUBLICATIONS

U.S. Notice of Allowance on U.S. Appl. No. 15/422,393 dated Aug. 14, 2017.
U.S. Office Action for U.S. Appl. No. 13/128,821 dated Nov. 14, 2013.
U.S. Office Action for U.S. Appl. No. 13/638,435 dated Feb. 10, 2016.
U.S. Office Action for U.S. Appl. No. 13/638,435 dated Jun. 30, 2015.
U.S. Office Action for U.S. Appl. No. 13/638,435 dated Mar. 12, 2015.
U.S. Office Action for U.S. Appl. No. 14/309,491 dated Jul. 28, 2015.
U.S. Office Action for U.S. Appl. No. 14/309,491 dated Mar. 3, 2016.
U.S. Office Action for U.S. Appl. No. 14/470,423 dated Jan. 21, 2016.
U.S. Office Action for U.S. Appl. No. 13/128,821 dated Dec. 14, 2012.
U.S. Office Action for U.S. Appl. No. 13/128,821 dated Apr. 24, 2012.
U.S. Office Action for U.S. Appl. No. 14/316,154 dated Dec. 18, 2014.
U.S. Office Action for U.S. Appl. No. 13/512,936 dated Aug. 14, 2013.
U.S. Office Action for U.S. Appl. No. 13/056,261 dated Jan. 9, 2014.
U.S. Office Action in U.S. Appl. No. 13/056,261 dated Aug. 7, 2013.
U.S. Office Action on U.S. Appl. No. 14/287,917 dated Sep. 26, 2014.
U.S. Office Action on U.S. Appl. No. 14/731,296 dated Apr. 6, 2017.
U.S. Office Action on U.S. Appl. No. 15/281,468 dated Jun. 14, 2017.
U.S. Office Action on U.S. Appl. No. 15/369,766 dated Apr. 20, 2017.
Written Opinion for PCT/EP2010/068658 dated Jun. 1, 2012.
Written Opinion for Singapore Application No. 201103393-3 dated May 2, 2012.
Written Opinion of the International Search Authority for PCT/IB2009/07715 dated May 12, 2011.

* cited by examiner

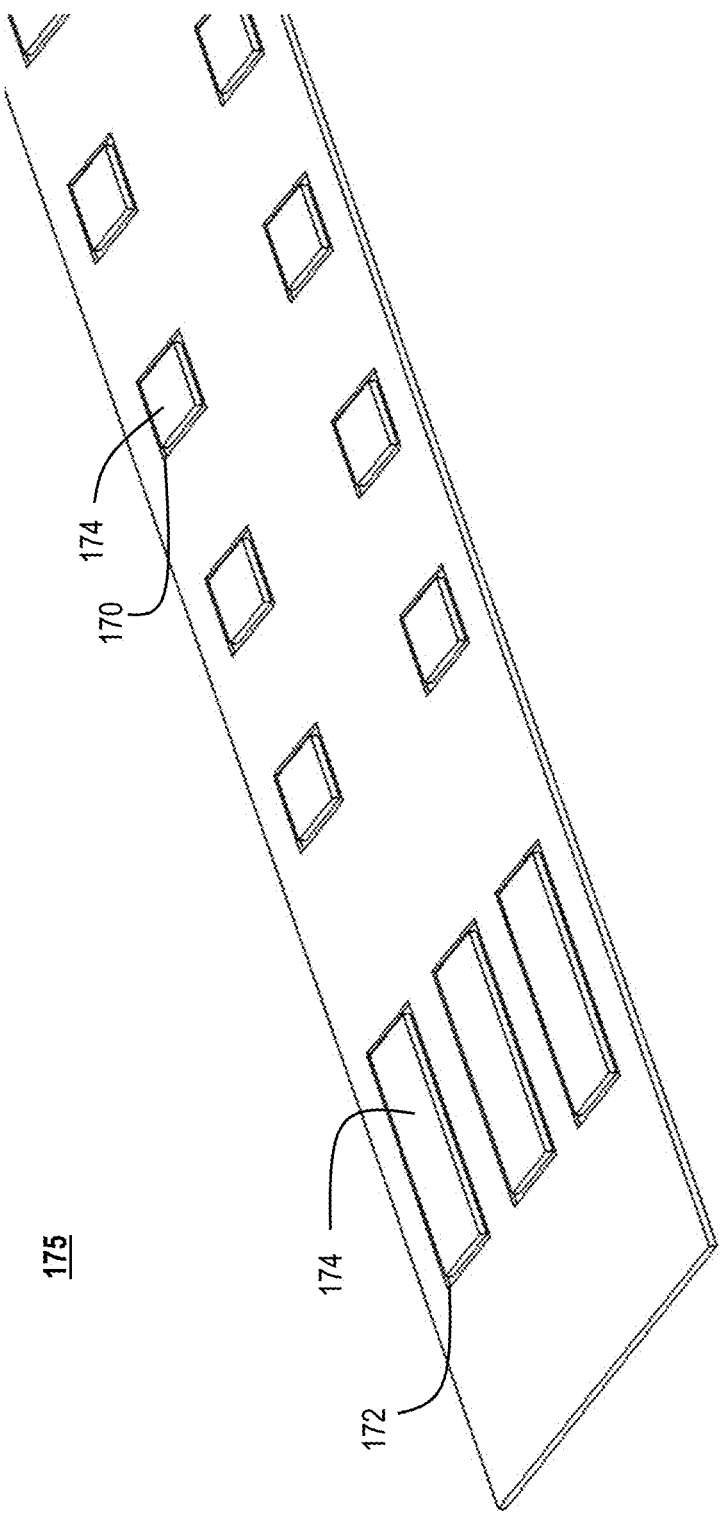

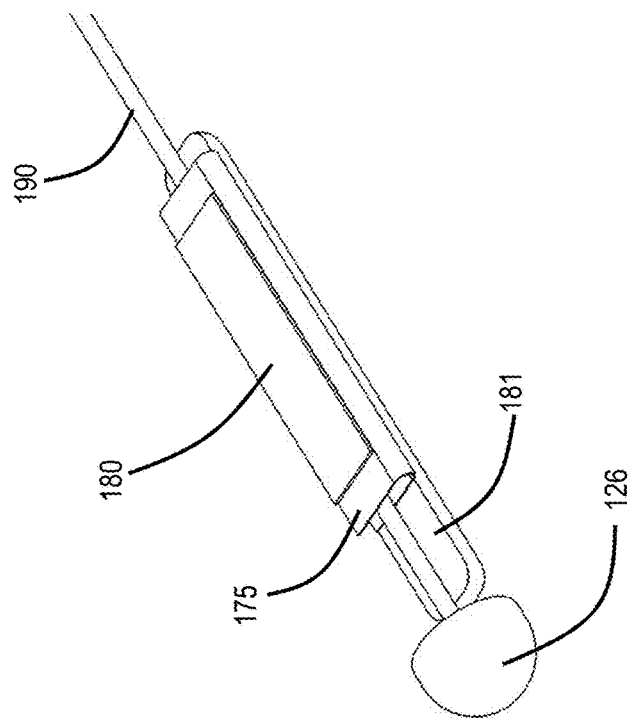
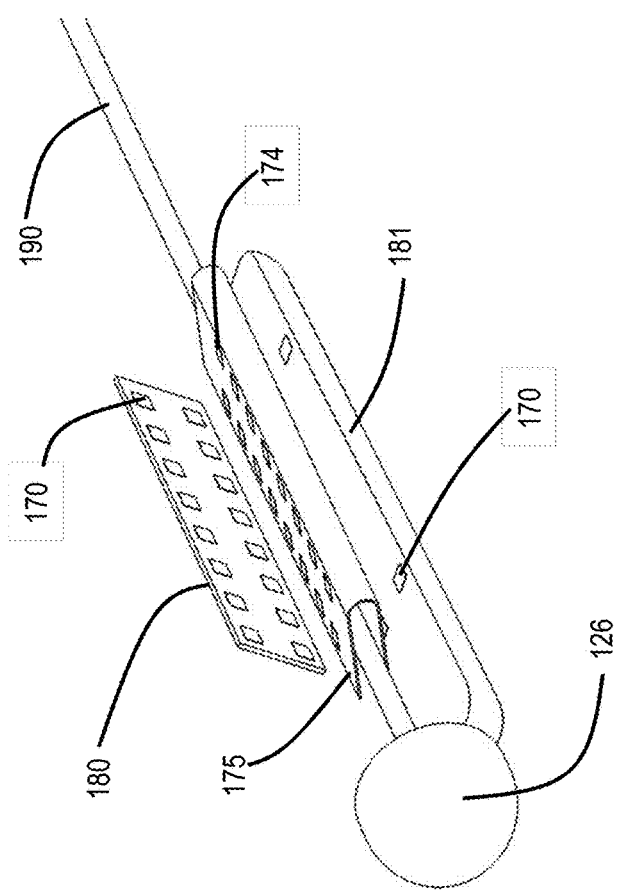
FIG. 20A
FIG. 20B

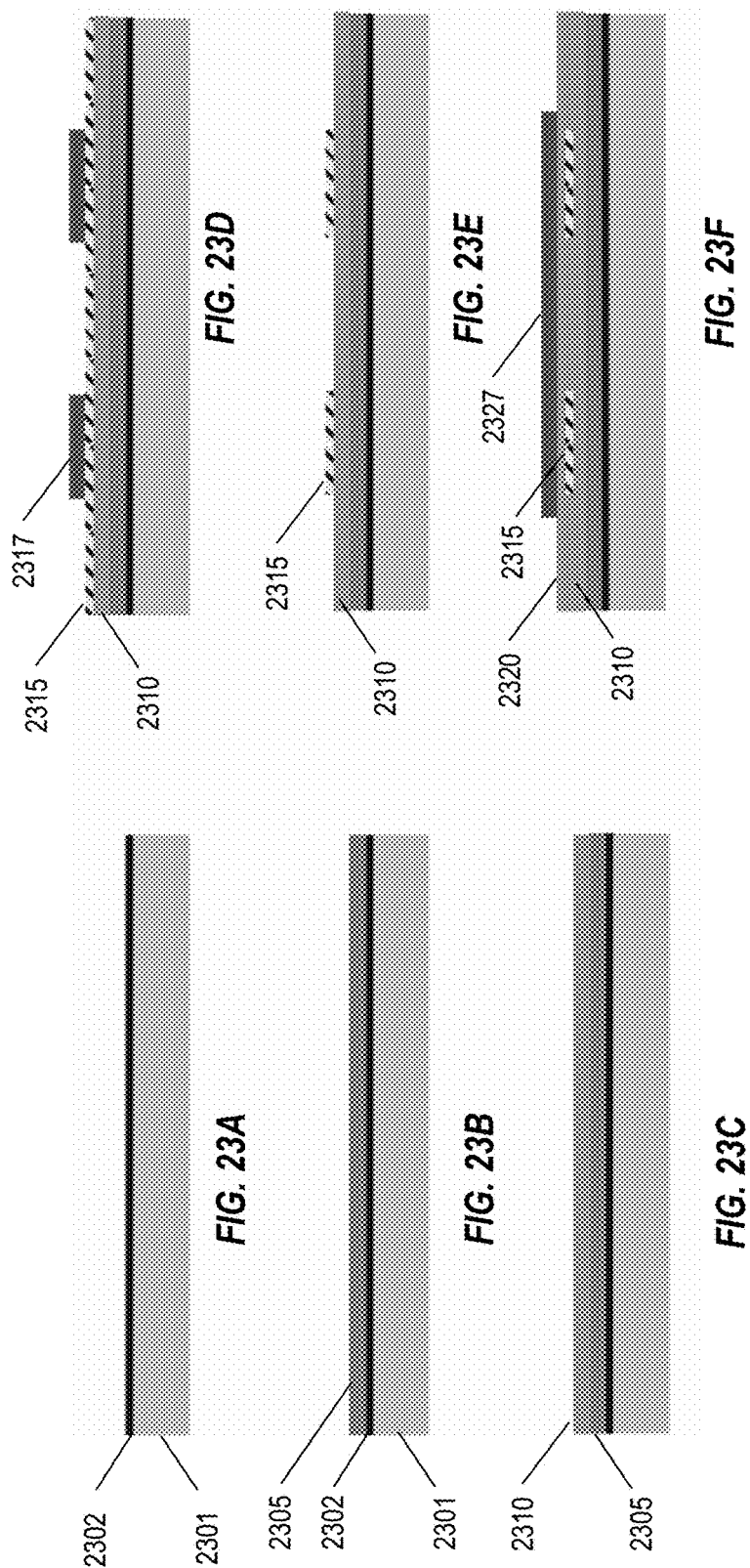

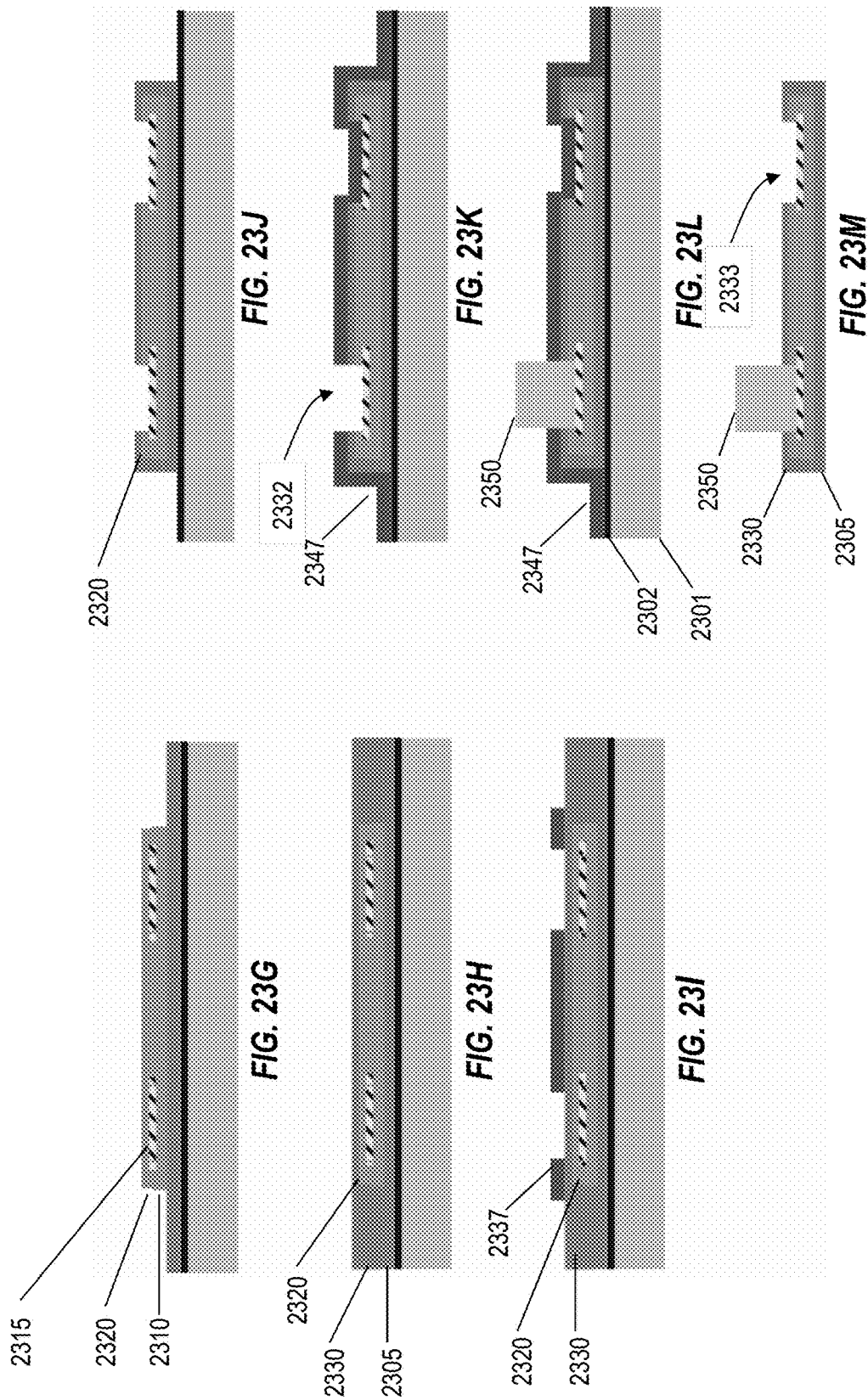

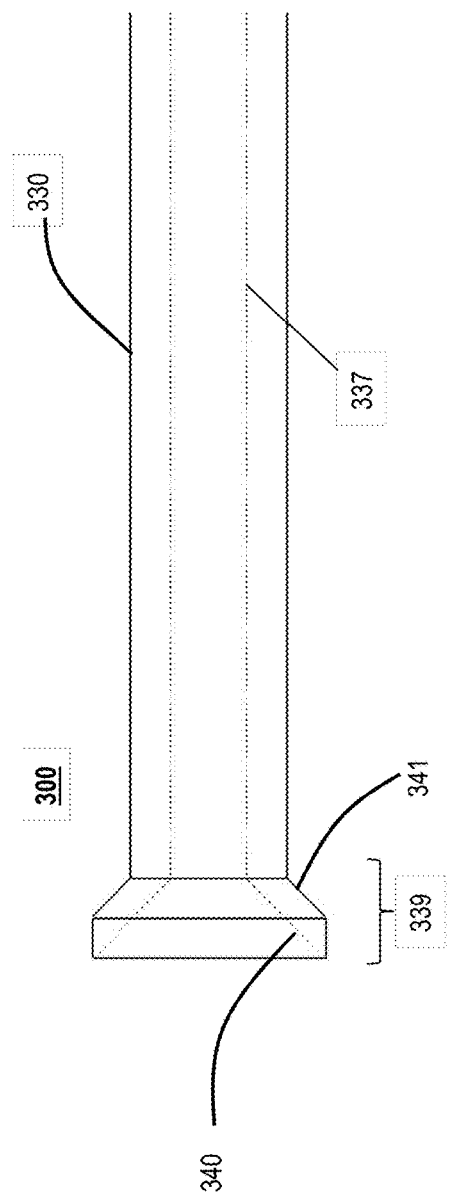
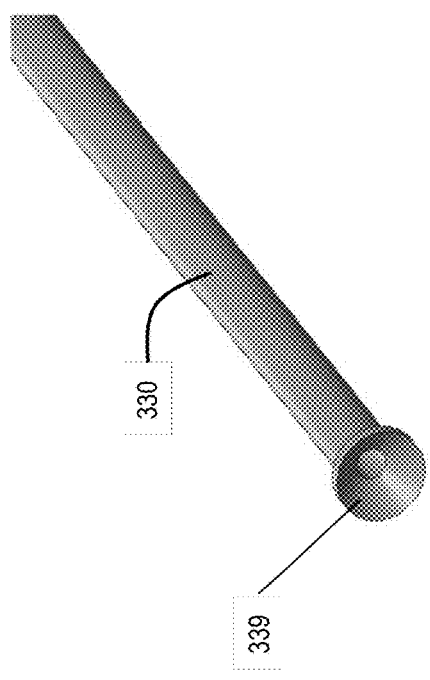
FIG. 25A
FIG. 25B

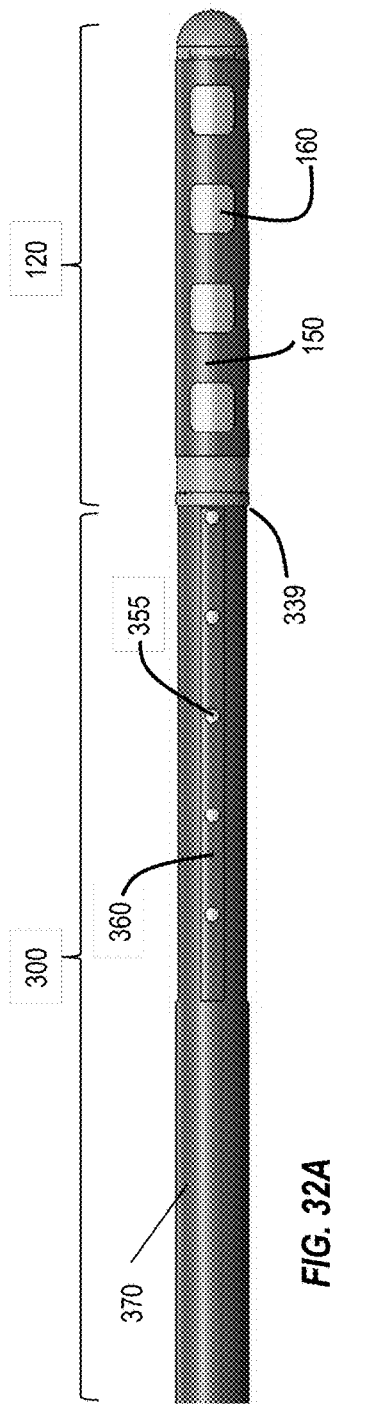
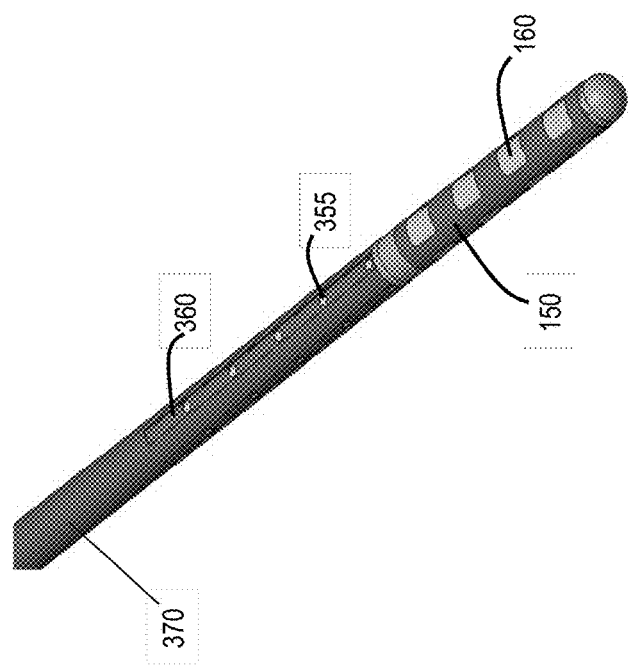
FIG. 32A
FIG. 32B

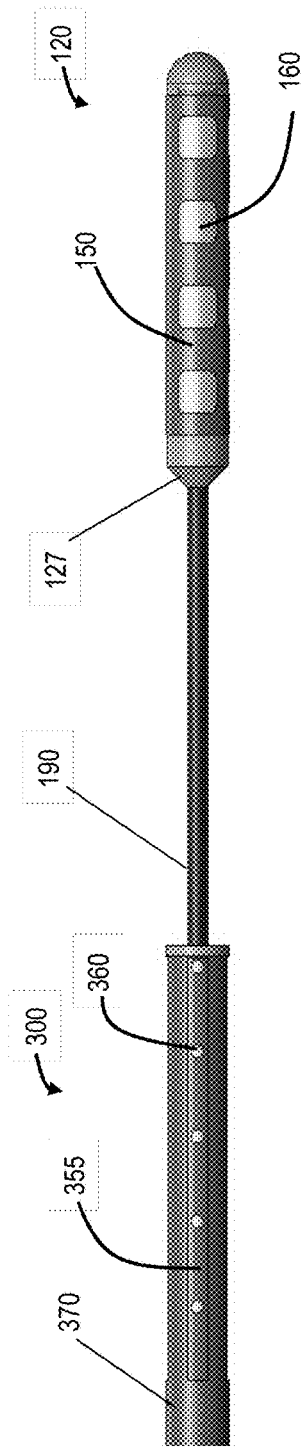
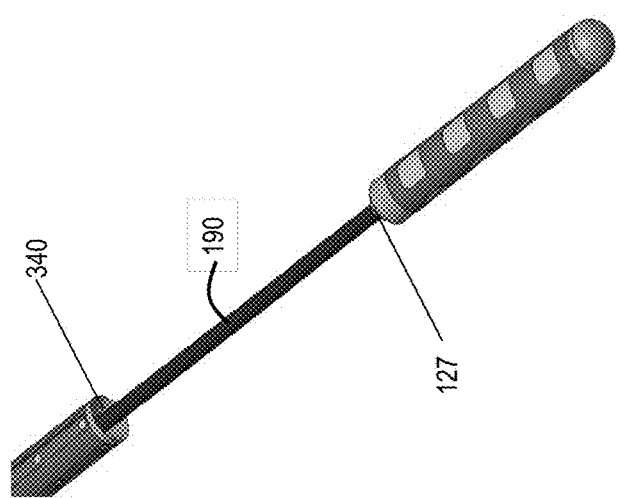
FIG. 34A
FIG. 34B

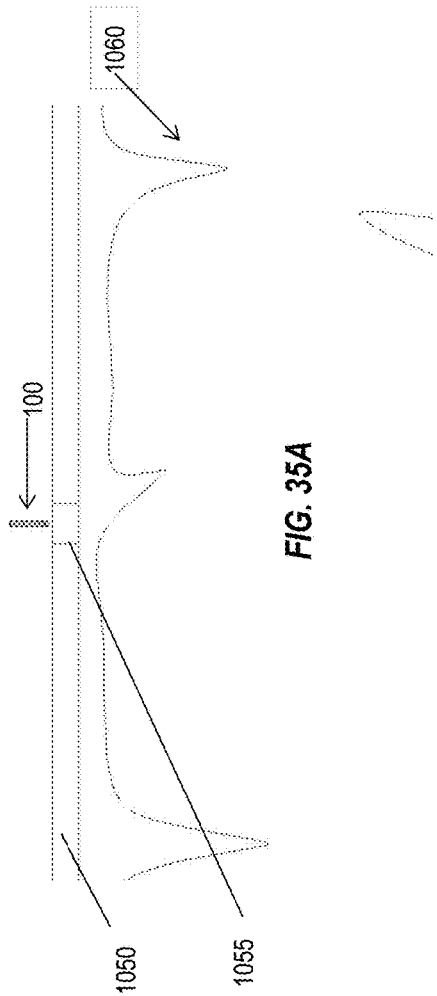
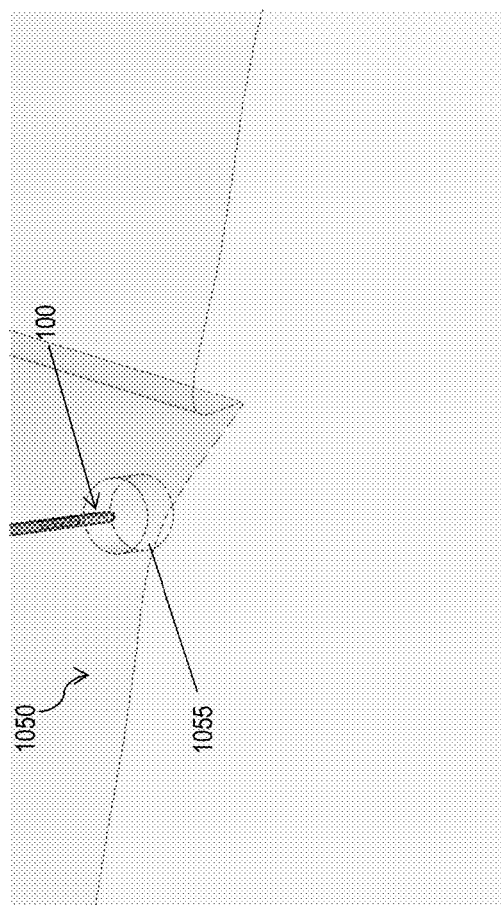

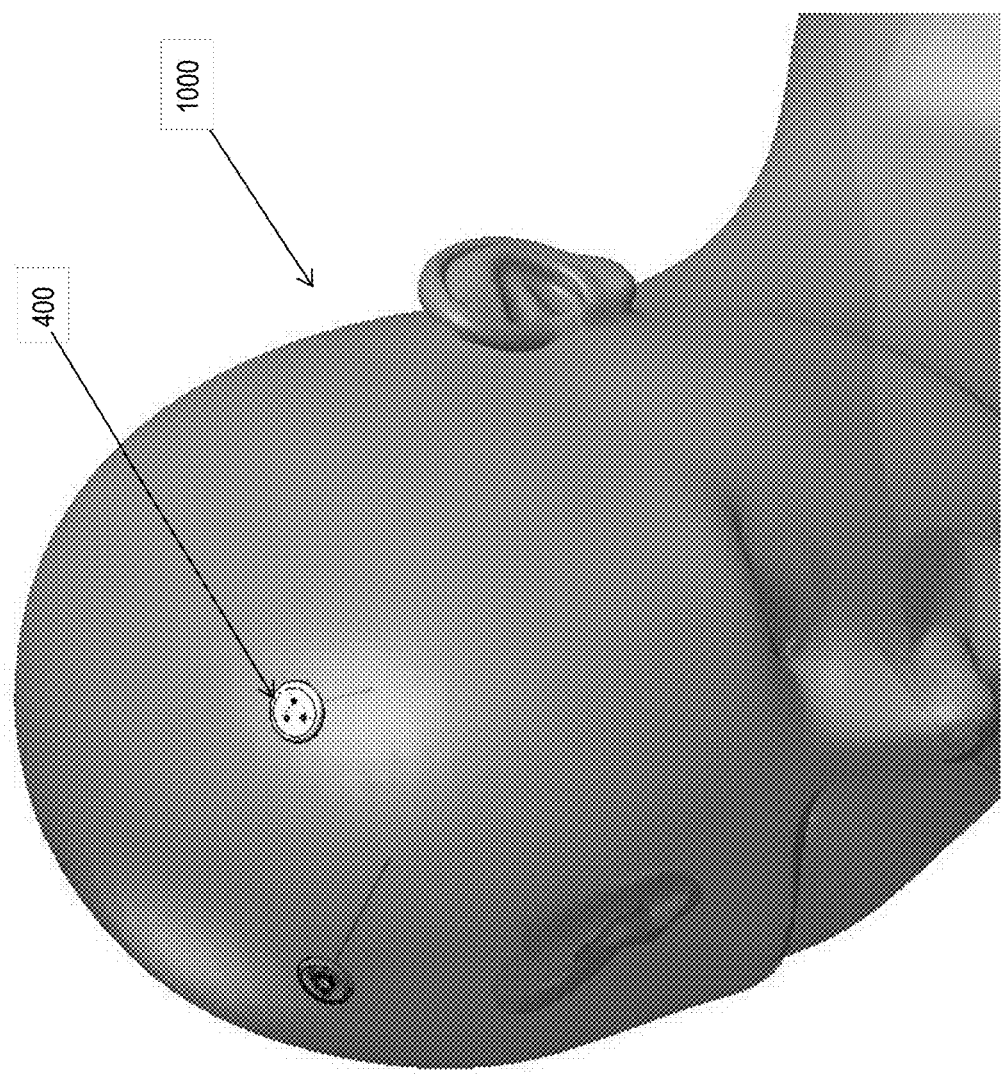

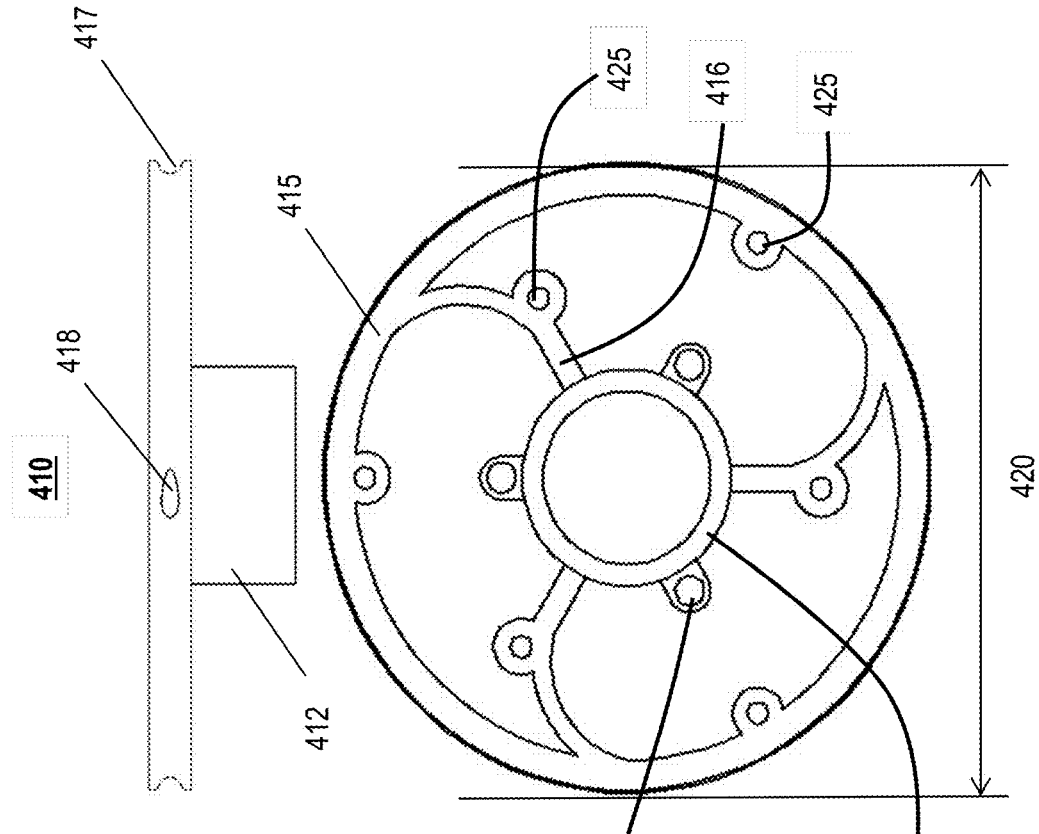

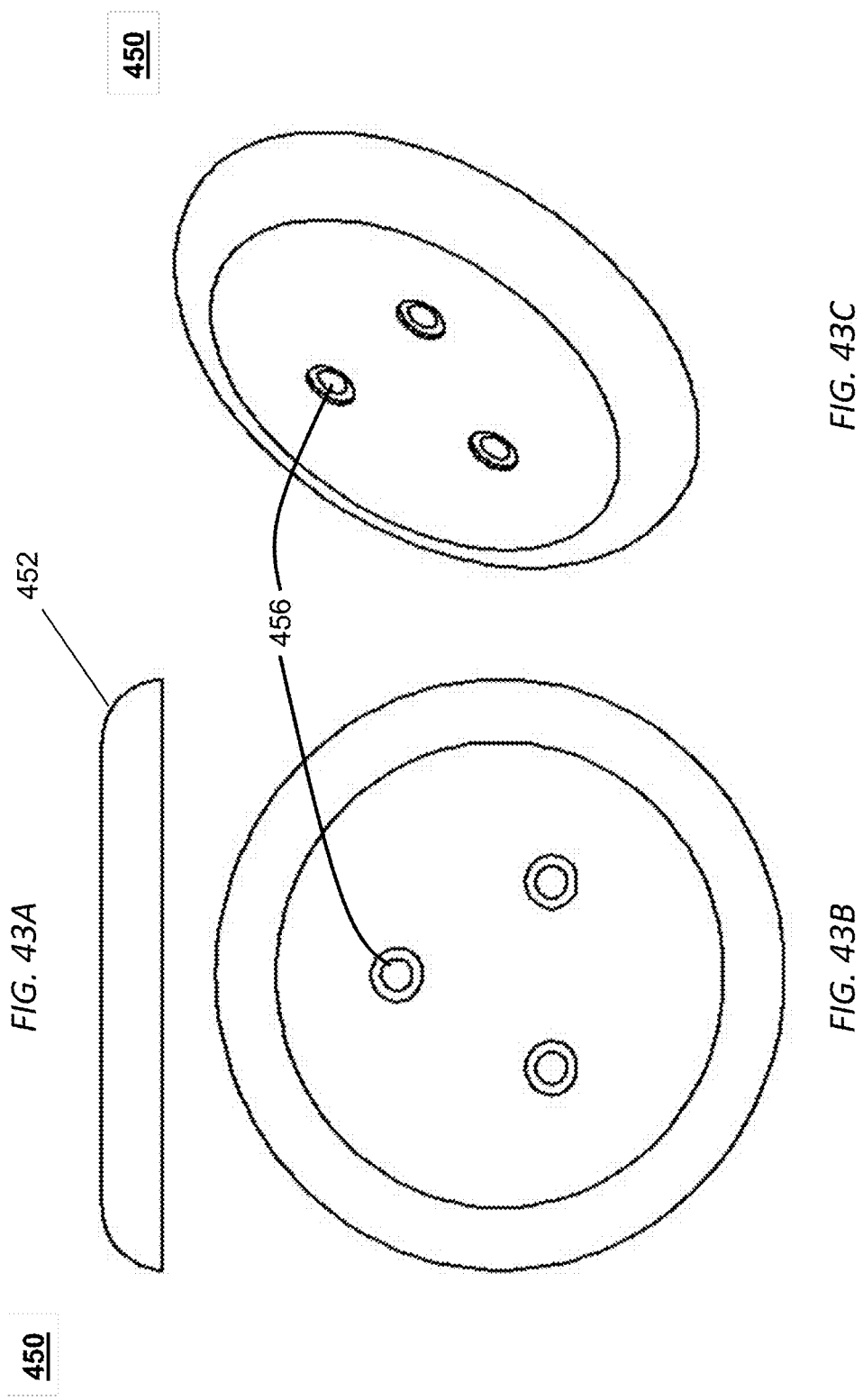

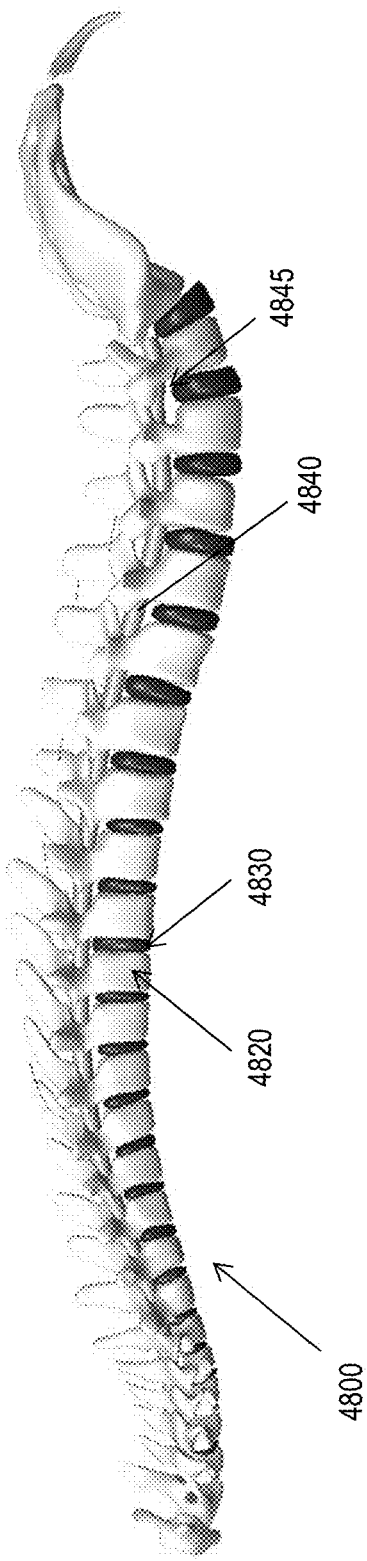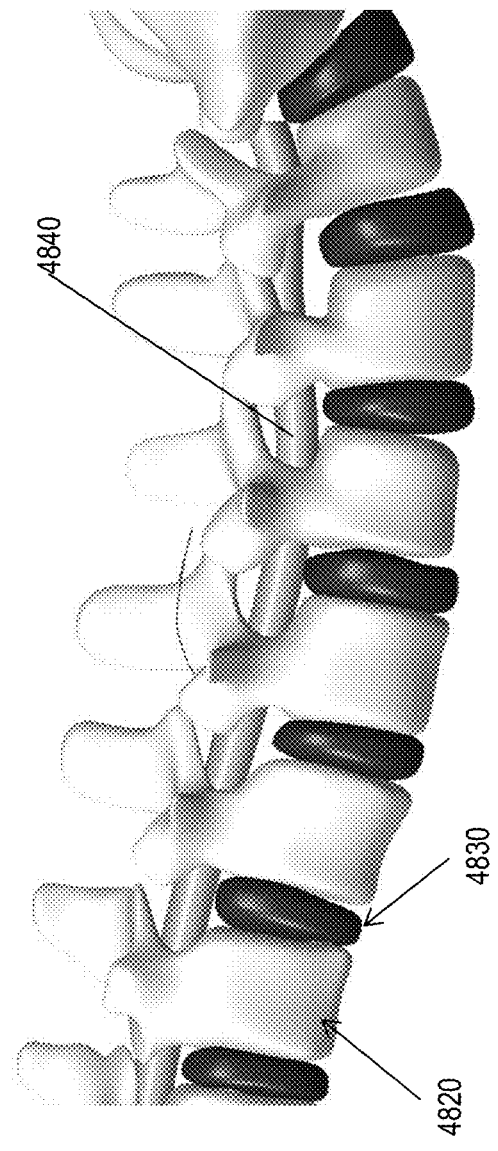
FIG. 48A
FIG. 48B

LEADLESS NEUROSTIMULATOR

CROSS-REFERENCE TO RELATED APPLICATIONS

The present application claims the benefit of priority under 35 U.S.C. § 120 as a continuation of U.S. patent application Ser. No. 15/194,033, filed Jun. 27, 2016 and issued as U.S. Pat. No. 9,572,985 on Feb. 21, 2017, which claims the benefit of priority under 35 U.S.C. § 121 as a divisional of U.S. patent application Ser. No. 14/470,356, filed on Aug. 27, 2014 and issued on Aug. 2, 2016 as U.S. Pat. No. 9,403,011. The contents of the foregoing applications are incorporated by reference in their entirety.

BACKGROUND

Deep brain stimulation (DBS) is a neurostimulation therapy which involves electrical stimulation systems that stimulate the human brain and body. DBS can be used to treat a number of neurological disorders. Typically DBS involves electrically stimulating a target area of the brain.

SUMMARY

According to one aspect of the disclosure a neurostimulation device includes a stimulation capsule with a proximal and distal end. The stimulation capsule includes a MEMS film with a plurality of electrodes. The MEMS film defines a lumen. The stimulation capsule also includes a stimulation source disposed within the lumen and electrically coupled to at least one of the plurality of electrodes. The stimulation capsule can also include a power supply disposed within the lumen and electrically coupled with the stimulation source. The stimulation capsule can include a tether coupled with the proximal end of the stimulation capsule.

In some implementations, a diameter of the stimulation capsule is less than a diameter of the tether. The tether can include an antenna or the MEMS film can include a strip or a serpentine antenna. The antenna can be configured to operate at a center frequency of one of 6.790 MHz, 13.560 MHz, 27.120 MHz, 40.680 MHz, 433.920 MHz, 915.000 MHz, 2.450 GHz, 5.800 GHz, and 24.125 GHz. In some implementations, the antenna is forms a loop. The antenna can be used to program the stimulation capsule, and the antenna can include one or more wires in electrical communication with the stimulation capsule. The one or more wires can each couple with a wire tether contact disposed on a ribbon cable. The ribbon cable can extend from a distal end of the MEMS film into the lumen.

In some implementations, the stimulation source and the power supply are disposed on the ribbon cable. The power supply can be battery or super-capacitor. A recording circuit can also be coupled with the ribbon cable. In some implementations, the MEMS film includes a first polymeric layer, a first barrier layer, a metal layer, a second barrier layer, and a second polymeric layer.

According to another aspect of the disclosure, a method of manufacturing a stimulation device includes forming a MEMS film. The MEMS film can include a plurality of electrodes and a ribbon cable extending from a distal end of the MEMS film. The method can also include coupling a stimulation source with a first plurality of contacts. The first plurality of contacts can be disposed on a first face of the ribbon cable and can be in electrical communication with at least one of the plurality of electrodes. A power supply can be coupled with a second plurality of contacts. The second plurality of contacts can be disposed on a second face of the ribbon cable. The method also includes folding the ribbon cable toward a face of the MEMS film, and forming, with the MEMS film, a lumen. The ribbon cable can be disposed within the lumen.

In some implementations, the method also includes coupling a recording circuit on a third plurality of contacts disposed on the first face of the ribbon cable. The first face of the ribbon cable can be different than the second face of the ribbon cable.

The method can also include filling the lumen with an encapsulating epoxy. A lead wire can be coupled with a tether contact. The tether contact can be disposed toward a distal tip of the ribbon cable. In some implementations, the method includes heat molding the MEMS film to form the lumen. The power source can include a rechargeable battery of a super capacitor.

BRIEF DESCRIPTION OF THE DRAWINGS

The figures, described herein, are for illustration purposes only. Various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings. The systems and methods may be better understood from the following illustrative description with reference to the following drawings in which:

FIG. 7 illustrates an enlarged view of example contact pads for the MEMS film of FIGS. 5 and 6.

FIGS. 20A and 20B illustrate the internal arrangement of an example leadless stimulator.

FIGS. 23A-23M illustrate an example thin-film microfabrication method for fabricating a MEMS film.

FIGS. 25A and 25B illustrate a cut away and perspective view, respectively, of the distal end of the guide tube for the deployment system of FIG. 24.

FIGS. 32A and 32B illustrate the distal end of the example deployment system of FIG. 24.

FIGS. 34A and 34B illustrate the distal end of the example deployment system of FIG. 24, with the guide tube separated from the leadless stimulator.

FIGS. 35A-38B illustrate an example method of implanting the leadless stimulator.

FIG. 39 illustrates a patient with a burr hole cover frame.

FIGS. 42A-42C illustrate the example lower part of the burr hole cover frame from FIG. 39.

FIGS. 43A, 43B, and 43C illustrate side, top, and perspective views of the burr hole cover cap.

FIGS. 48A-48E illustrates an example of the leadless stimulator implanted near a patient's spinal cord.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes a medical device to provide neurostimulation therapy to a patient's brain. The device can be surgically implanted and generally can remain in the patient until end of life. The present disclosure also describes accessories which guide the implantation of the device, and the components that form a leadless stimulator implantation kit.

Figure 1A:
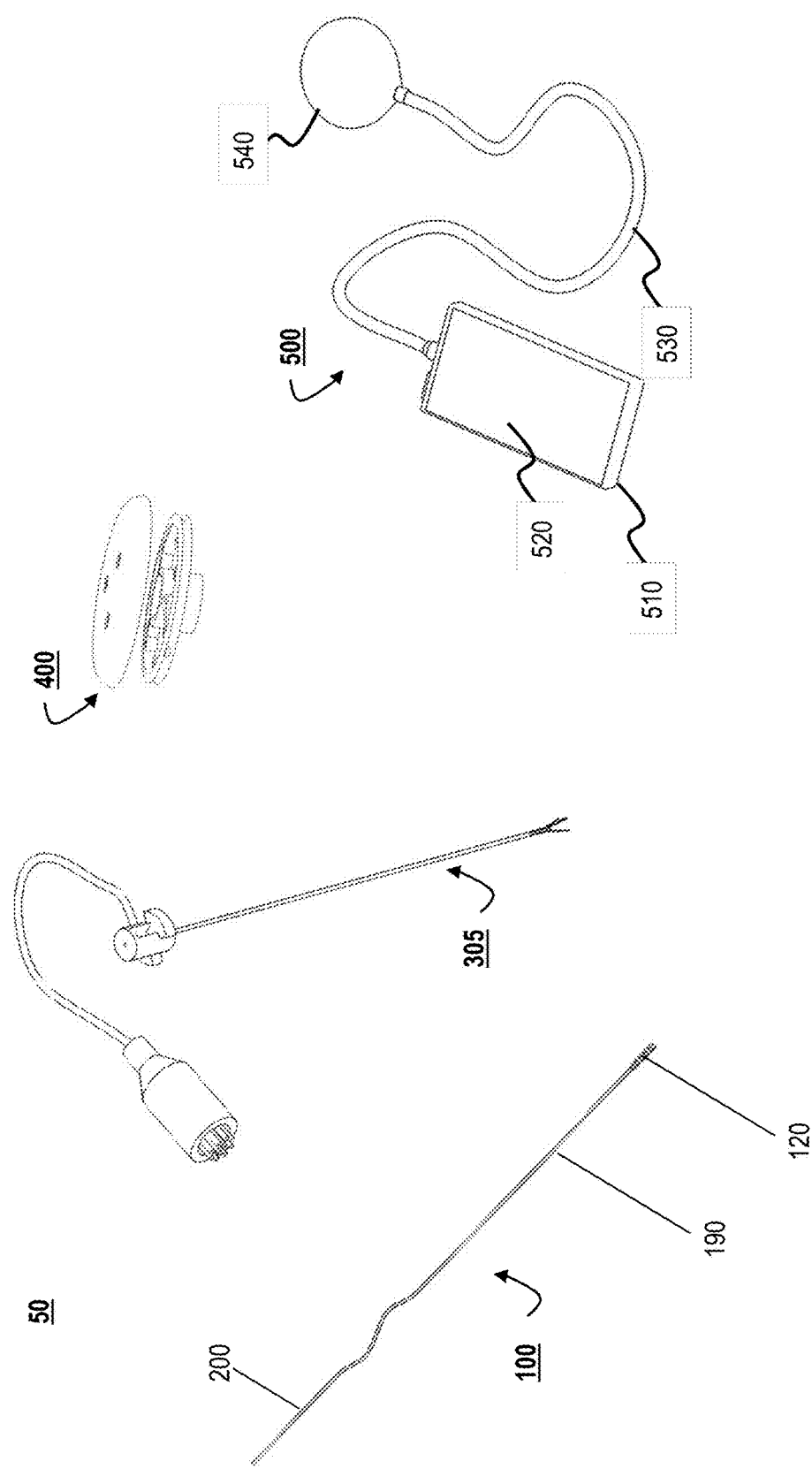
FIGS. 1A and 1B illustrates an example leadless stimulator system.

FIG. 1A illustrates an example leadless stimulator system 50. The leadless stimulator system 50 can include a leadless stimulator 100, a deployment system 305, a burr hole cover frame 400, and an external programmer 500. The leadless stimulator 100 can include an antenna 200 and a stimulation capsule 120. The stimulation capsule 120 is coupled with the antenna 200 by a tether 190. The deployment system 305 can be used to implant the leadless stimulator 100 into a patient—for example, into a patient's brain through a craniotomy. The burr hole cover frame 400 can be used to secure the antenna 200 and the correctly position the antenna 200 for communication with the external programmer 500. The external programmer 500 can read and write data to the leadless stimulator 100 through wireless communication with the leadless stimulator 100 using the antenna 200 of the leadless stimulator 100.

As illustrated in FIG. 1, the leadless stimulator system 50 can include an external programmer 500. The external programmer 500 can include a main unit 510, which holds the power source and electronics for the operation of the external programmer 500. The main unit 510 can include a screen 520 to provide visual information to the user. In some implementations, the screen 520 is a touch screen. The external programmer 500 can also include an antenna tether 530 that tethers the external programmer 500 to the external antenna 540. In some implementations, the external antenna 540 can have a diameter that provides efficient communication with the leadless stimulator 100 via the antenna 200 of the leadless stimulator 100. For example, the external antenna 540 could have a diameter between about 25 mm and about 75 mm or between about 45 mm and about 55 mm while the implanted antenna 200 can have a diameter between about 15 mm and about 35 mm or between about 20 mm and about 30 mm. The external programmer 500 can communicate with the leadless stimulator 100 wirelessly after the implantation of the leadless stimulator 100. The external programmer 500 can send data to the leadless stimulator 100 in order to set the stimulation parameters of the leadless stimulator 100. For example, the external programmer 500 can set signal attributes such as frequency, pulse width, amplitude, polarity, and signal shape, along with additional stimulation parameters, or a combination thereof. The final delivered pulses can be charge balanced, such that the pulse can have a cathodal and anodal phase. In some implementations, it is advantageous for the electrode if the amount of charge delivered during the cathodal phase is substantially equal to the amount of charge delivered during the anodal phase. Generally the pulses have a pulse width between 20 us and 1 ms, and the pulse frequency is between 20 Hz and 10 kHz depending on the clinical application. The external programmer 500 can also be used to turn the leadless stimulator 100 on or off. The external programmer 500 can also be used to control the post-operative neural recording features of the leadless stimulator 100. The external programmer 500 can be used to download data (e.g., usage data and recorded physiological data) from the leadless stimulator 100. In some implementations, the external programmer 500 can receive the data from the leadless stimulator 100 in substantially real time and in other implementations the leadless stimulator 100 may store the data for later retrieval with the external programmer 500.

In some implementations, the external programmer 500 may be used to recharge the internal batteries of the leadless stimulator 100. The external antenna 540 can be used to inductively couple power from an external power source to the leadless stimulator 100. In other implementations, the leadless stimulator 100 can have no internal power source. In this case the inductively coupled power from external programmer 500 can be used to power the leadless stimulator 100. In general, the leadless stimulator 100 can consume between about 5 mW and about 15 mW in clinical operation, and therefore the external programmer 500 is configured to supply sufficient power to charge the leadless stimulator 100 based on these demands.

Figure 1B:
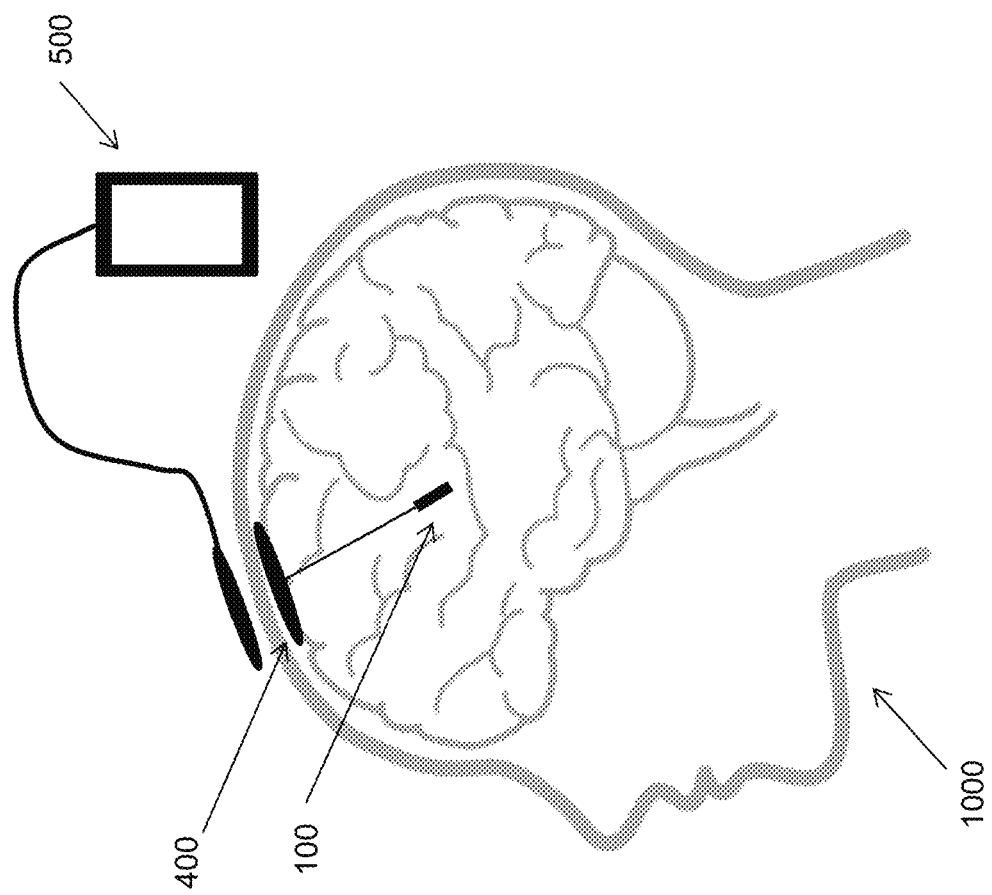

FIG. 1B illustrates the leadless stimulator 100 implanted into a patient's brain system 50 with the burr hole cover frame 400 and the external programmer 500 external to the patient's brain. The leadless stimulator 100 can be implanted responsive to the patient having a surgical planning procedure that involves MRI and/or CT scans to localize brain targets, thereafter the leadless neurostimulator 100 can be implanted in the deep brain using components of the leadless neurostimulator system 50. The deployment system 305 can push the leadless neurostimulator 100 to the brain target, and subsequently removed leaving the leadless stimulator 100 towards the brain target. The implantable antenna 200 remains remain extra-cranial. The burr hole cover frame 400 is used to fill the burr hole and stabilize the leadless stimulator 100. As described below, in some implementations, implantable antenna 200 is wrapped around the burr hole cover frame 400 to provide the correct diameter for efficient extra-corporeal communication. After implantation and surgical recovery, the external programmer 500 is used to program the leadless stimulator 100. The external programmer 500 can also provide power, or in some implementations recharge, the leadless stimulator 100.

Figure 2:
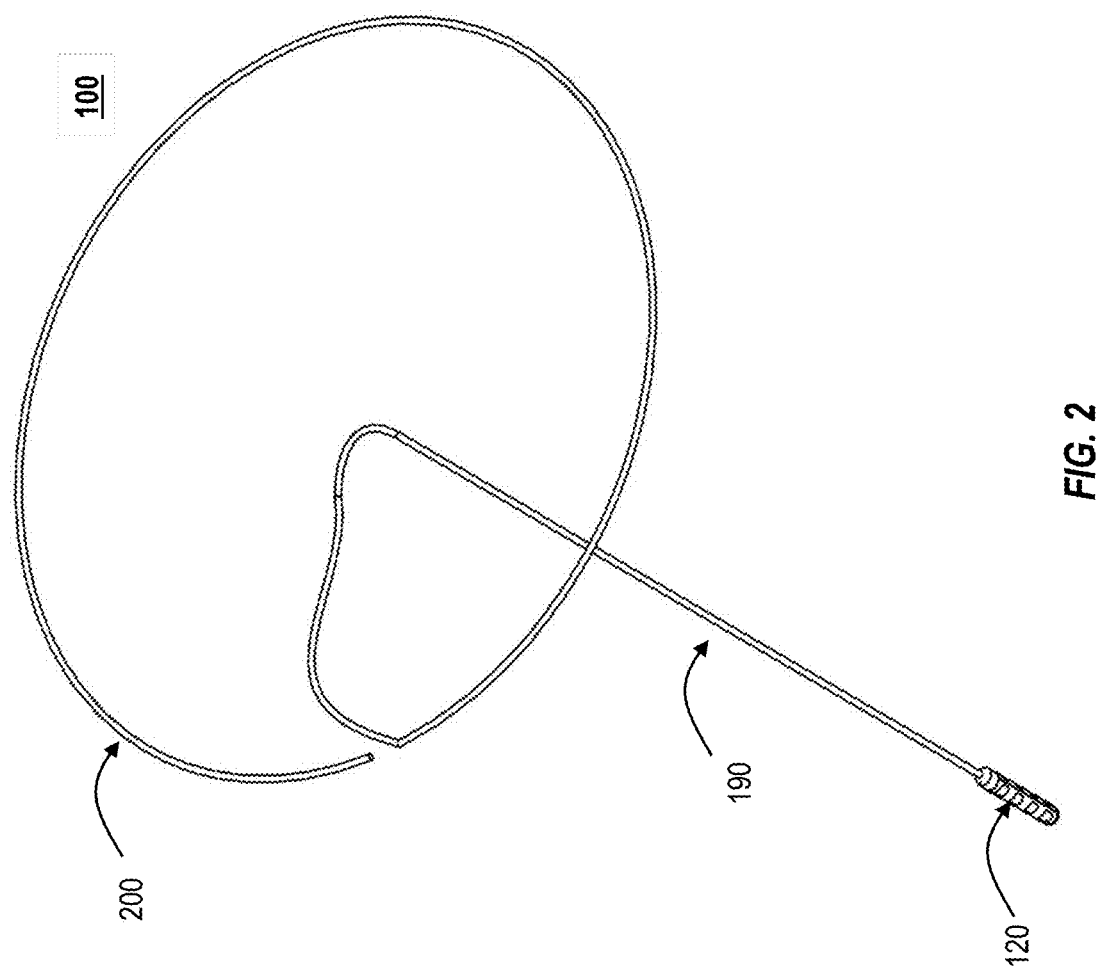
FIGS. 2 and 3 illustrate an example leadless stimulator from the leadless stimulator system of FIG. 1A.
Figure 3:
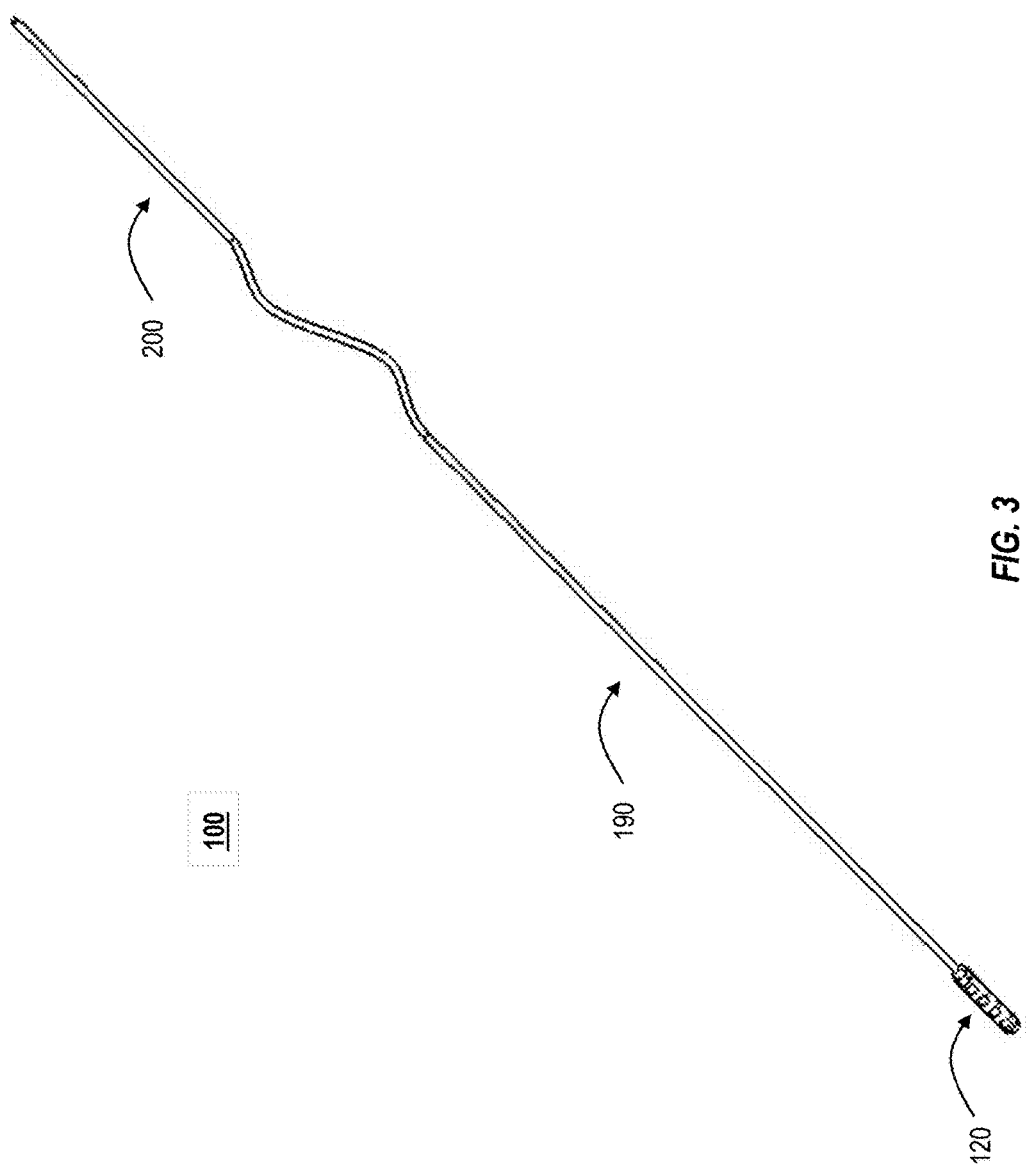

FIGS. 2 and 3 illustrate the leadless stimulator 100. In FIG. 2 the antenna 200 is in a wrapped configuration, and in FIG. 3 the antenna 200 is in an outstretched configuration. The leadless stimulator 100 can include a stimulation capsule 120, a tether 190, and an antenna 200. The stimulation capsule 120 can include a plurality of electrodes and can record and/or stimulate the neurological tissue into which it is implanted.

The leadless stimulator 100 also includes an antenna 200 that can be coupled to the stimulation capsule 120 with the tether 190. The tether 190 can provide a mechanical and electrical coupling between the antenna 200 and the stimulation capsule 120. In some implementations, the antenna 200 is reversibly coupled with the tether 190 and in other implementations the antenna 200 is permanently coupled with the tether 190. In some implementations, the tether 190 and the antenna 200 refer to the same part of the leadless stimulator 100. For example, the part of the antenna outside of the patient may be referred to as the antenna 200 while the portion of the antenna inside the patient may be referred to as the tether 190. As illustrated in FIGS. 2 and 3, part, or all, of the tether 190 and antenna 200 can be flexible. For example, the antenna 200 can be configured to be flexible enough to enable the antenna 200 to be coiled within a burr cover that is implanted in the patient's skull or to form a loop as illustrated in FIG. 2. The tether 190 and the antenna 200 have a diameter of about 0.5 mm, but could range from as small as 0.2 mm to as large as 2 mm. The wires that form the antenna 200 can form a bifurcated tail body. The bifurcated tail body forms an antenna loop. The antenna 200 can include a wire coil that is embedded in a flexible, elastomeric body. The antenna loop may be flexible enough be stretched over a burr hole cover, which can position the antenna 200 in a predetermined shape (e.g., a loop of a predetermined diameter). In other implementations, as illustrated if FIG. 2, the antenna 200 may be wound into a circular loop of the predetermined diameter. The below discussed burr hole cover frame may be used to ensure the antenna 200 maintains the predetermined diameter.

The predetermined diameter of the antenna can enable the efficient coupling of antenna 200 and the external antenna 540 of the external programmer 500. In some implementations, the leadless stimulator 100 communicates wirelessly with the external programmer 500 over the 27 MHz frequency. Other frequencies which could be used are any of those determined by the International Telecommunication Union Radiocommunication Sector (ITU-R) in their reserved Industrial, Scientific, and Medical (ISM) Bands such as for example, but not limited to, 6.780 Mhz, 13.560 MHz, 40.680 MHz, 2.450 GHz, 5.80 GHz. The antenna diameter can be inversely proportional to the wavelength of the signal the antenna 200 transmits over. For example, with a 27 MHz frequency the loop diameter of the antenna 200 can be about 25 mm in diameter. In general, the loop diameter of the antenna is about half the wavelength of the frequency used to communicate with the antenna.

Figure 4:
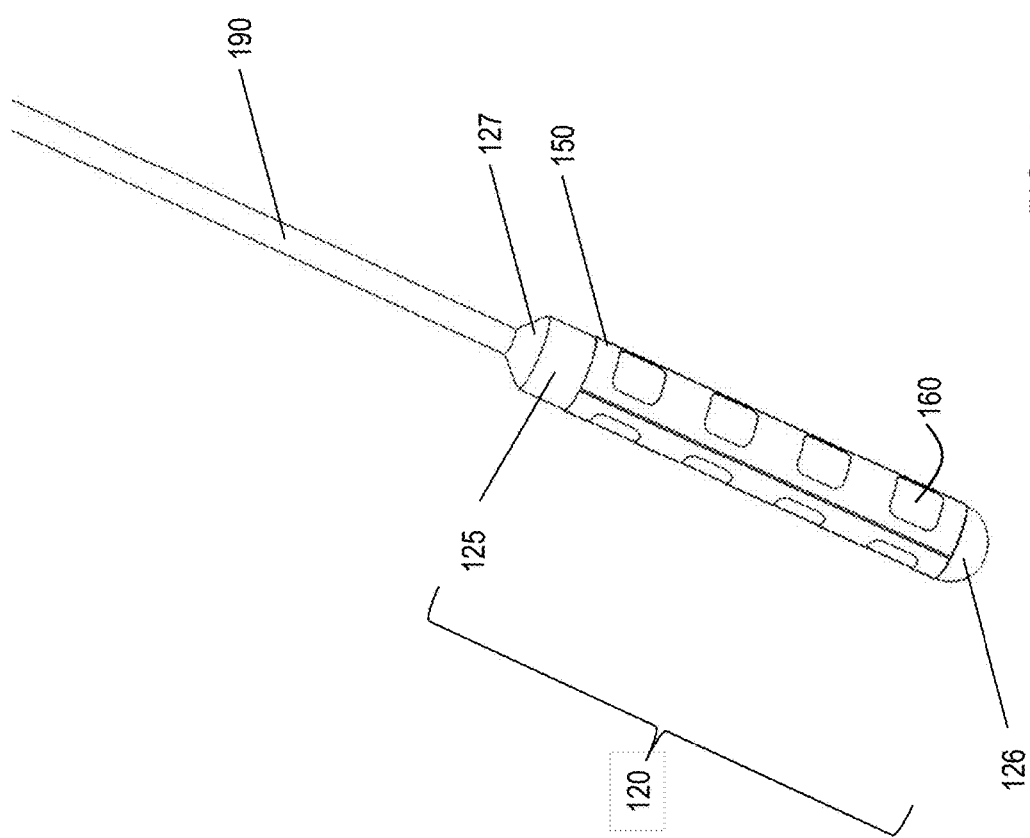
FIG. 4 illustrates an enlarged view of the leadless stimulator from FIGS. 2 and 3.

FIG. 4 illustrates an enlarged view of the distal end of the leadless stimulator 100 from FIGS. 1-3. The stimulation capsule 120 is coupled with the tether 190 at the proximal end 127 of the capsule body 125. The capsule body 125 can be conical or cylindrical in shape. The proximal end 127 can mate with the distal end of a cannula (not illustrated) during the implantation procedure. In general, the capsule body 125 includes a polymeric material and houses the active electronic components of the leadless stimulator 100. In some implementations, electronic components may also be housed in the tether 190 and antenna 200. The stimulation capsule 120 can include a hemispherical distal tip 126. The distal tip 126 can include electronic components. These electronic components are generally integrated circuits, resistors, capacitors, or a combination thereof.

The stimulation capsule 120 can be cylindrical and have a larger diameter than the tether 190. In some implementations, the diameter of the stimulation capsule 120 is between about 0.3 mm and about 3 mm, between about 0.75 mm and about 2.5 mm, between about 1 mm and about 2 mm, or between about 1.2 mm and about 1.6 mm.

The stimulation capsule 120 can also include a MEMS film 150. The MEMS film 150 can manufactured as a substantially planar film, which is coupled around the capsule body 125. In some implementations, the MEMS film 150 is wrapped to form a cylindrical shape and then glued or co-molded into place. The MEMS film 150 can include one or more electrodes 160. As illustrated in FIG. 4, the MEMS film 150 includes twelve electrodes (only eight of the electrodes 160 are visible in FIG. 4). In some implementations, the electrodes 160 can be implemented in a noble metal, such as platinum. In other implementations, the electrodes 160 can be implemented in gold, titanium, iridium oxide, platinum grey, platinum black, and oxides of titanium. As illustrated the electrodes 160 substantially square with rounded corners. In some implementations, the electrodes 160 can be circular, rectangular, or any other shape. In some implementations, the electrodes 160 can be used for physiological recordings and simulations.

Figure 6:
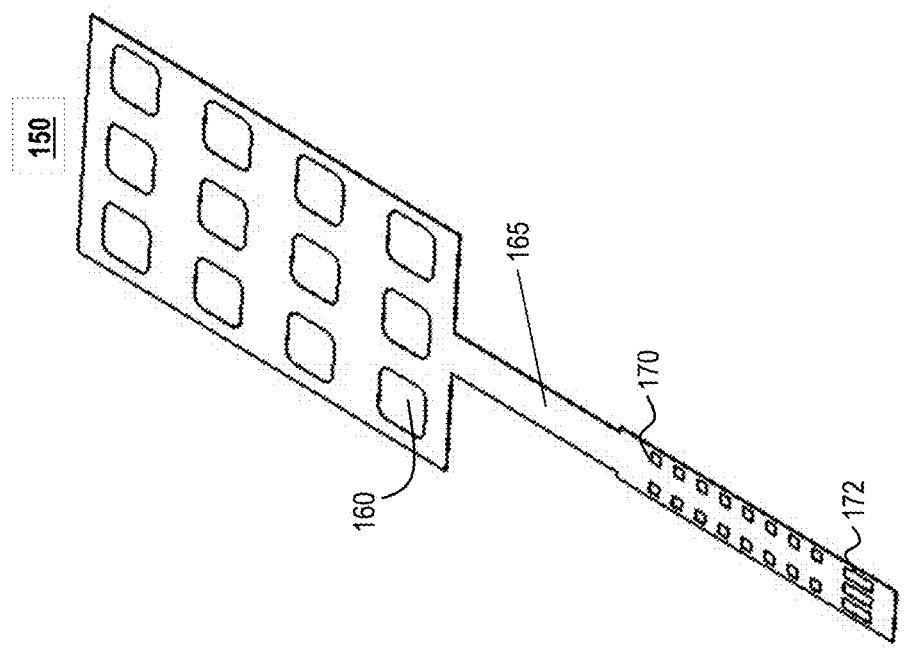
FIGS. 5 and 6 illustrate an example MEMS film for use in the example leadless stimulator of FIG. 1A.
Figure 5:
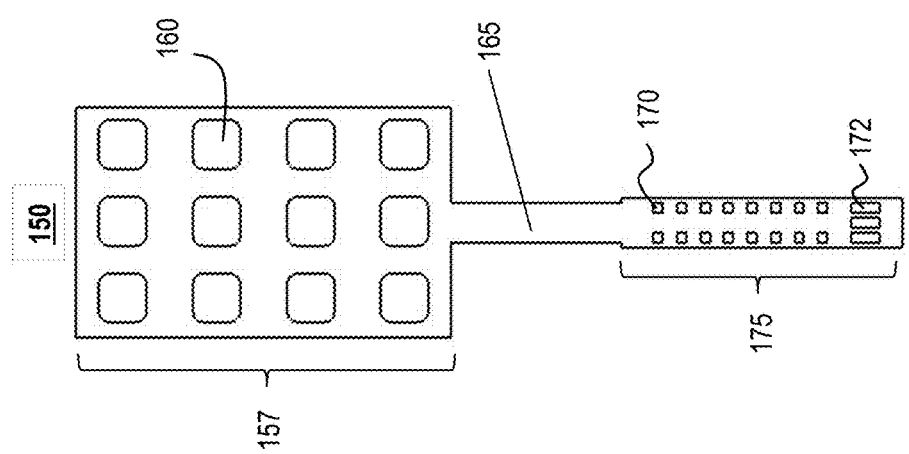

FIGS. 5 and 6 illustrate the MEMS film 150 in its substantially planar configuration. The MEMS film 150 includes twelve electrodes 160 disposed across the exterior portion 157 of the MEMS film 150. In some implementations, the MEMS film 150 has about 4, 6, 8, 12, 16, 24, 36, 48, 64, or more electrodes 160. The electrodes 160 can be arranged in specific patterns. For example, FIGS. 5 and 6 illustrate an electrode arrangement that includes three columns and four rows of electrodes 160. In other implementations, the electrodes 160 can be rectangular electrodes that span the width of the exterior portion 157 and form ring electrodes when the MEMS film 150 is rolled into its cylindrical shape.

The MEMS film 150 also includes a ribbon cable 165. The lower portion of the ribbon cable 165 includes the contact pad 175. The contact pad 175 includes a plurality of contacts 170. Each of the contacts 170 can be coupled with one or more of the electrodes 160 through traces embedded within the MEMS film 150. For example, the MEMS film 150 may include twelve electrodes 160 and twelve contacts 170. In this example, each of the contacts 170 may be coupled with a different one of the twelve electrodes 160. In some implementations, the contact pad 175 may include fewer contacts 170 than electrodes 160. In this example, one or more electrodes 160 may be coupled with the same contact 170, such that they may be stimulated (or recorded from) as a single unit. In some implementations, the contact pad 175 includes contacts 170 configured for different purposes. For example, the contact pad 175 illustrated in FIGS. 5 and 6 includes a second type of contacts—the wire tether contacts 172. The different types of contacts are generally referred to as contacts 170. The wire tether contacts 172 are used to couple the MEMS film 150 to the wires of the tether 190 and antenna 200. The contacts 170 may be coupled to an application-specific integrated circuit (ASIC) or other electronic component that is housed within the stimulation capsule 120.

FIG. 7 illustrates an enlarged view of the contact pad 175 from FIGS. 5 and 6. In some implementations, a metal layer 174 is deposited on the contacts 170. The metal layer 174 can include gold or other metal such as platinum, titanium, or copper. In some implementations, the addition of a metal layer 174 increases the ease of welding or attaching electronic components (e.g., antenna wires) to the contacts 170. In some implementations, the metal layer 174 improves the contacts' 170 ability to go undergo flip-chip bonding. The improvement in creating a contact with the contacts 170 may be caused by the metal layer 174 rising above the polyimide surface of the contact pad 175, making it easier for electronic components to be coupled to the contacts 170.

Figure 8:
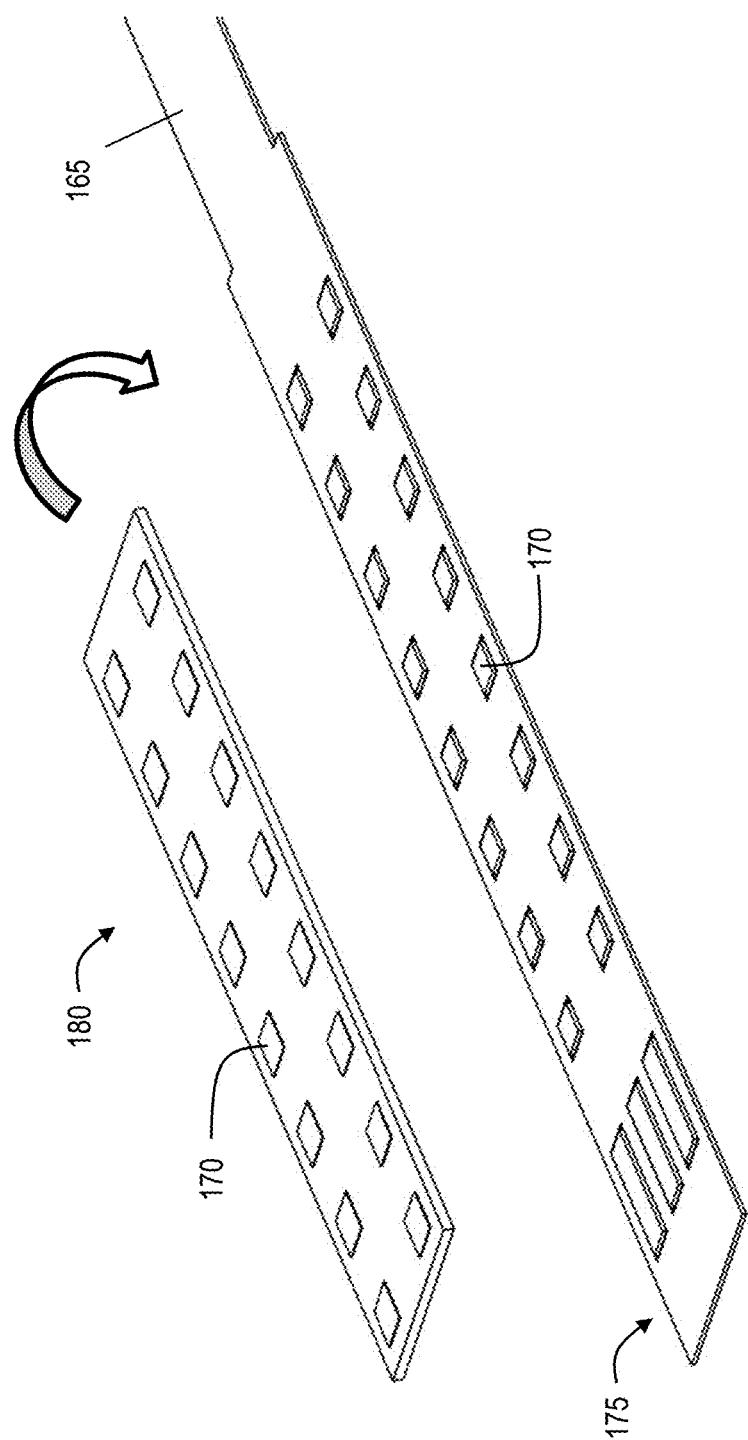
FIGS. 8-13 illustrate an example, assembled contact pad for the MEMS film of FIGS. 5 and 6.
Figure 9:
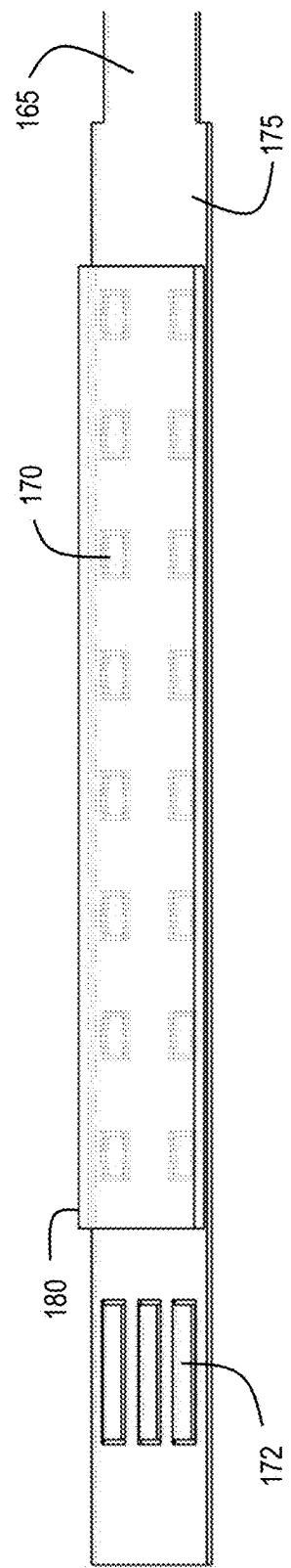

FIGS. 8-13 illustrate the assembly of an example contact pad 175. FIG. 8 illustrates an ASIC 180 prior to its coupling with the contact pad 175. In some implementations, the internal electronics of the stimulation capsule 120 are coupled to the contact pad 175. As illustrated, a single ASIC 180 is coupled with the contact pad 175; however, the electronic components of the leadless stimulator 100 can be divided among a plurality of ASICs 180, batteries, passive electronic components (e.g., resistors and capacitors), or other electronic components. The ASIC 180 includes a plurality of contacts 170, which are bound to the contacts 170 of the contact pad 175. The contacts 170 of the ASIC 180 can have the same pitch (e.g., spacing) as the pitch of the contact pad 175, such that the contacts 170 align and can be coupled together. In some implementations, the ASIC 180 is coupled with the contact pad 175 when the MEMS film 150 is a planar configuration—prior to the MEMS film 150 being formed into a cylindrical (or other) shape. For example, the ASIC 180 may be coupled with the contact pad 175 prior to the contact pad 175 being removed from the substrate on which it was fabricated. The ASIC 180 can be thinned to a thickness of about 50 µm, and generally has a thickness between about 20 and about 550 µm, prior to the ASIC 180 being coupled with the contact pad 175. FIG. 9 illustrates the contact pad 175 after the ASIC 180 is bound to the contact pad 175. As illustrated, the contacts 170 of the ASIC 180 are aligned and coupled with the contacts 170 of the contact pad 175. In some implementations, the ASIC 180 includes the stimulation source that is used to stimulate tissue via the electrodes 160. The ASIC 180 can also include a recording circuit. In some implementations, the stimulation capsule includes a plurality of ASIC 180.

Figure 10:
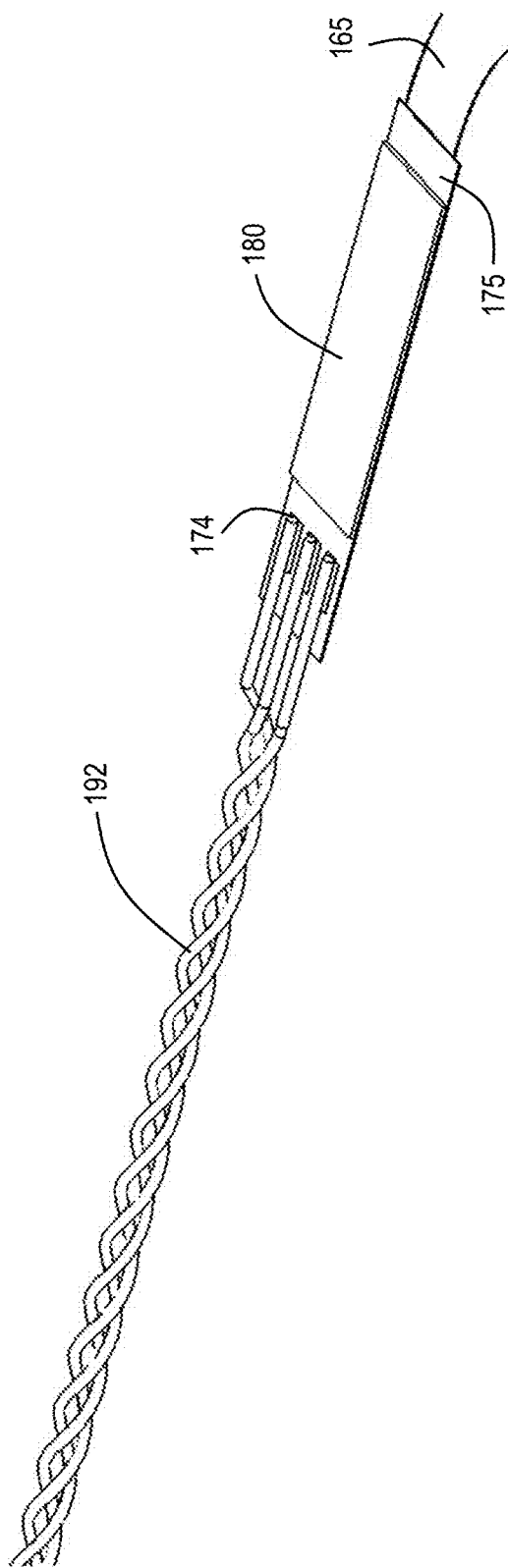

FIG. 10 illustrates the lead wires 192 coupled with the contact pad 175. One or more lead wires 192 can be coupled to the one or more wire tether contacts 172. The lead wires 192 can be electrically coupled with the antenna 200 through the tether 190. The lead wires 192 can include platinum-iridium wire, and have a thin electrically isolating coating. Incoming signals from the antenna 200 can be transmitted to the ASIC 180. The ASIC 180 can process these signals and record and stimulate through the electrodes 160 as instructed by the signals. The ASIC 180 can also transmit captured neural signals to a computer or other external device through by a transmission the signals over the antenna 200.

Figure 11:
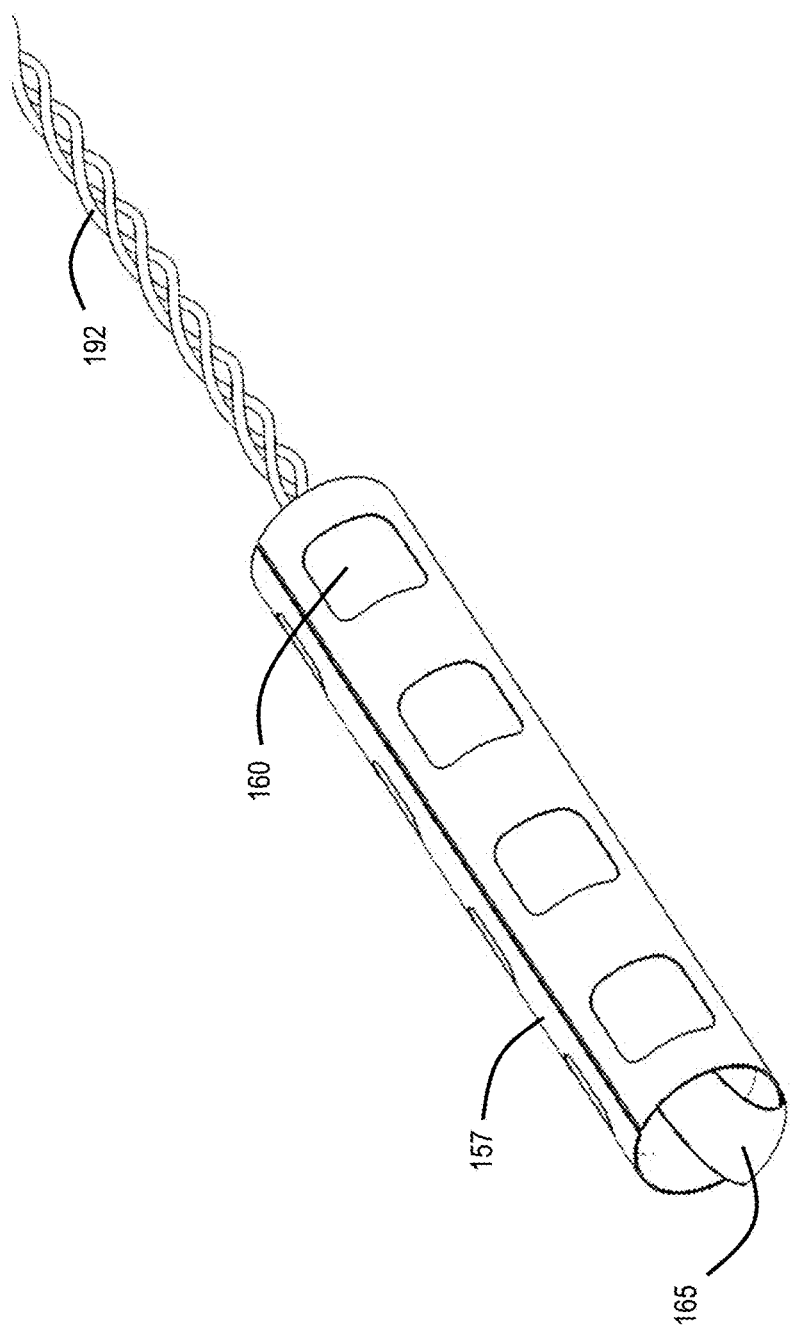

In some implementations, after the components of the leadless stimulator 100 are coupled together (while the MEMS film 150 is in a planar configuration) the MEMS film 150 can be molded into a cylindrical shape. FIG. 11 illustrates the MEMS film 150 molded into a cylindrical shape. The shaping of the MEMS film 150 into a non-planar shape (e.g., a cylinder) can be performed by heat molding the MEMS film 150 while protecting the mounted ASIC 180 or by molding the ASIC 180 in place. As illustrated the contact pad 175, with its coupled ASIC 180, is toward the MEMS film 150. The exterior portion 157 can then be rolled around the contact pad 175, such that the contact pad 175 with its coupled ASIC 180 (e.g., the stimulation source, the power supply, and the recording circuit) is within a lumen created by the rolled exterior portion 157.

Figure 12:
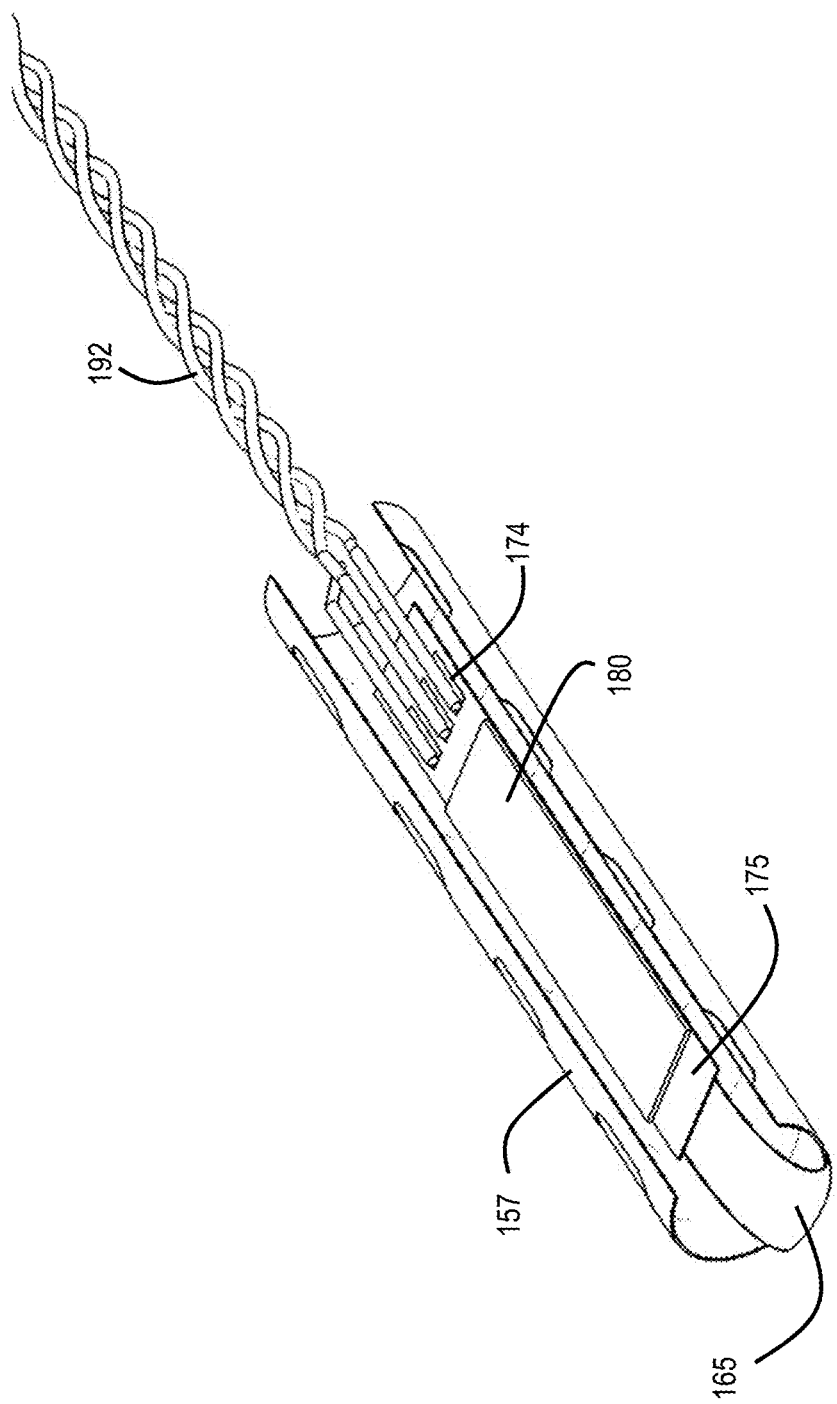

FIG. 12 illustrates a cutaway view of the MEMS film 150 molded into a cylindrical shape. FIG. 12 illustrates the folding of the MEMS film 150 into a cylindrical and the internal electronics of the MEMS film 150. As illustrated the ribbon cable 165 can be folded back such that the contact pad 175 at least partially overlaps the exterior portion 157. The edges of the exterior portion 157 are then rolled to create a cylinder around the ASIC 180. Once the exterior portion 157 is rolled into a cylindrical form, the created cylinder can be co-molded to create the leadless stimulator 100.

Figure 13:
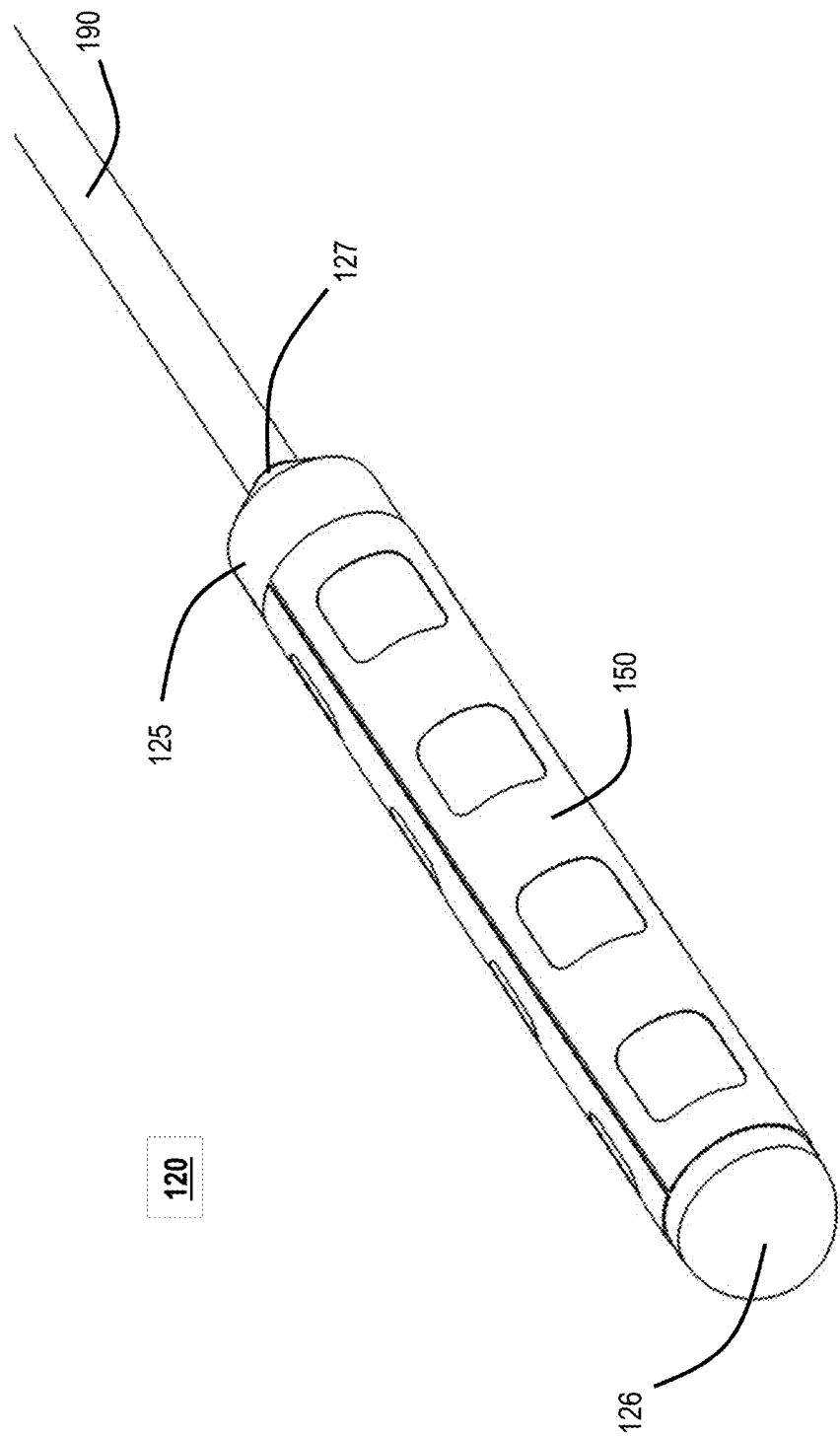

FIG. 13 illustrates an enlarged view of an example stimulation capsule 120. The rolled MEMS film 150 can be over-molded to create a mechanically stable device. In some implementations, the MEMS film 150 is rolled to create the cylindrical shape. The capsule body 125 of the leadless stimulator 100 is then manufactured by co-molding the MEMS film 150 to encapsulate the interior of the MEMS film 150 and the electronics therein. The co-molding of the MEMS film 150 can involve securing the MEMS film 150 in place and having it back-filled with a polymer precursor, such as an epoxy, to backfill the cavities within the molded MEMS film 150. The over-molding material may include epoxy materials, such as EPO-Tek 353, that provide sealing of the electronics and wire traces therein, protecting the electronics from body fluids that may disrupt electrical function. The stimulation capsule 120 can also include a distal tip 126. The distal tip 126 can be coupled with the capsule body 125 or the distal tip 126 can be created as part of the capsule body 125 during the over-molding process. As illustrated the distal tip 126 is hemispherical, although other shapes may be used. For example, the distal tip 126 can be beveled or blunt. The distal tip 126 enables atraumatic insertion of the leadless stimulator 100 into tissue during the implantation procedure.

FIG. 13 also illustrates the tether 190. The tether 190 can include a jacket, such as a polymeric tubing, around the lead wires 192. In some implementations, the tether 190 can be hollow and have a lumen through which the lead wires 192 run. In other implementations, the tether 190 can be filled, encapsulating the lead wires 192 or other electronic components in the lumen of the tether 190. In some implementations, the tether 190 is of a diameter of 0.5 mm, is flexible and easily wraps around a finger of a surgeon for example.

In some implementations, the leadless stimulator 100 may not include an antenna 200 at the surface of the skull. For example, the leadless stimulator 100 may include an integrated antenna (also referred to as a micro-antenna) on the stimulation capsule 120. An integrated antenna can reduce the risk of malfunction due to broken lead wires.

Figure 14:
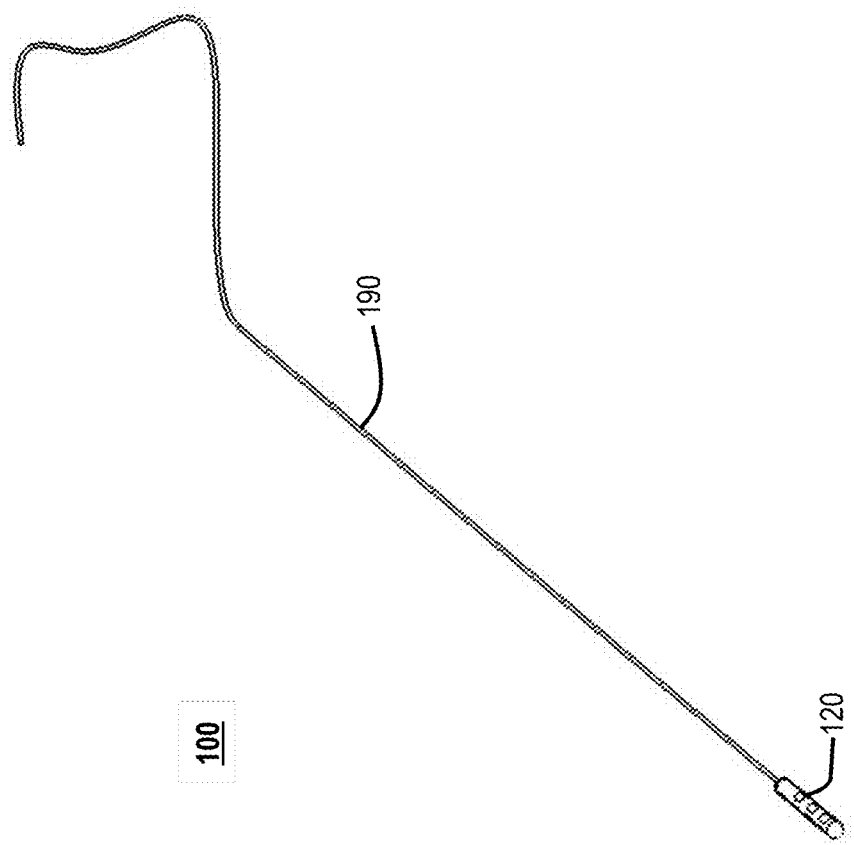
FIG. 14 illustrates an example leadless stimulator with a micro-antenna.

FIG. 14 illustrates an example leadless stimulator 100 with a micro-antenna. The leadless stimulator 100 with a micro-antenna can include a stimulation capsule 120 and a tether 190. In some implementations, for example with a micro-antenna, the tether 190 may not include lead wires to form an antenna; however, the leadless stimulator 100 may still include the tether 190 to facilitate the removal of the leadless stimulator 100 from a patient's tissue after implantation.

Figure 15:
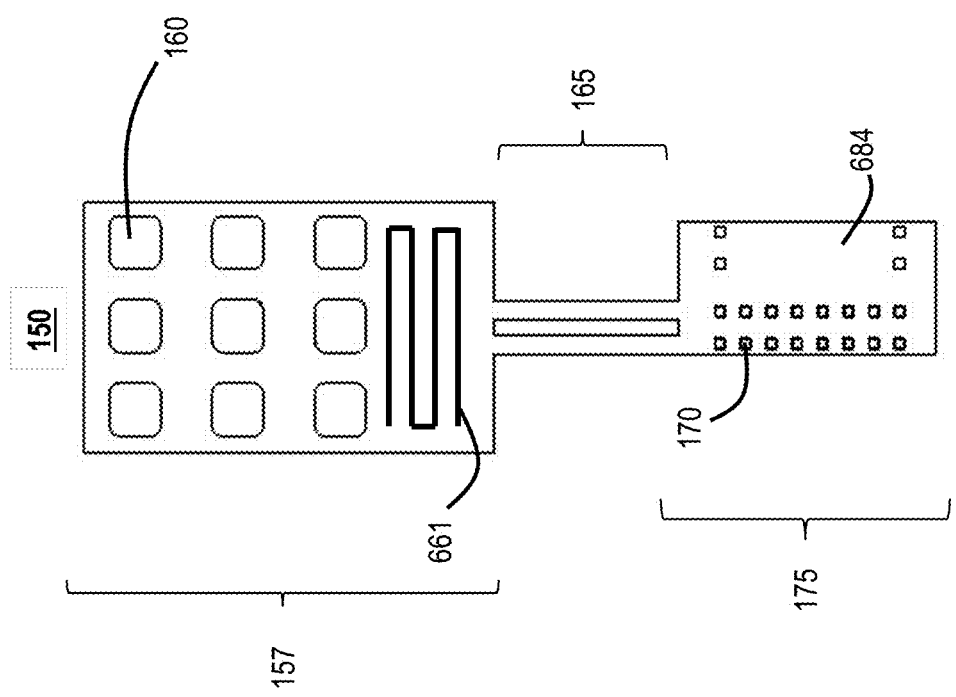
FIGS. 15-17 illustrate an example MEMS film for the example leadless stimulator of FIG. 14.
Figure 16:
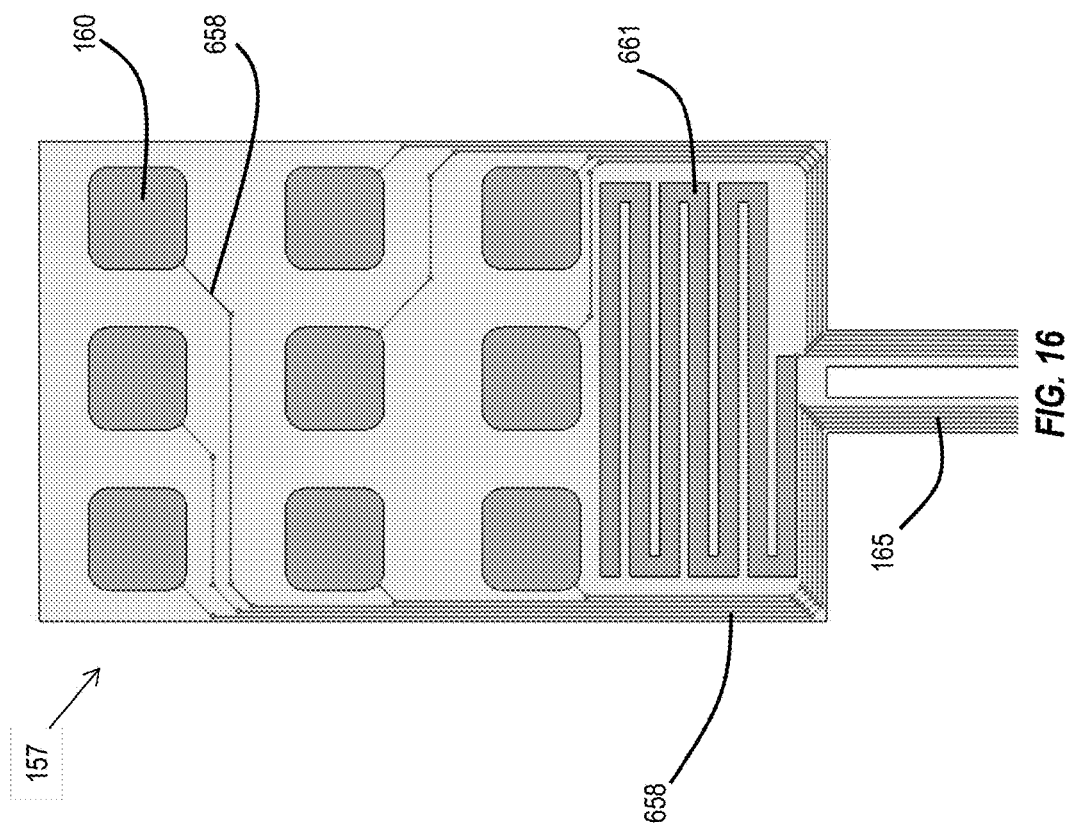

FIGS. 15 and 16 illustrate an example MEMS film 150 with a micro-antenna. The MEMS film 150 can include an exterior portion 157, a ribbon cable 165, and contacts 170. The exterior portion 157 includes nine electrodes 160 and a micro-antenna 661. In some implementations, the exterior portion 157 includes more than or fewer than nine electrodes 160. As illustrated in FIG. 15, the contact pad 175 includes a battery pad 684, on which a battery may be coupled. The battery may be coupled with the battery pad 684 in a means (e.g., flip chip bonding) similar to the means that an ASIC 180 is coupled to the contact pad 175. After the electronic components are coupled with the MEMS film 150, the battery pad 684 can be folded over on the contacts 170 of the contact pad 175. In the example illustrated in FIG. 15, the ribbon cable 165 is divided into two separate ribbon cables. In some implementations, the metal layer of the MEMS film 150 that includes the traces from the electrodes 160 to the contacts 170 and the micro-antenna 661 is covered by a top insulating layer to electrically insulate the components.

FIG. 16 illustrates an enlarged view of the example MEMS film 150 from FIG. 15. In FIG. 16 the top insulating layer of the MEMS film 150 is removed to illustrate the electrical elements embedded within the MEMS film 150. For example, removal of the top insulating layer exposes the micro-antenna 661 and the electrical traces 658. The electrical traces couple the electrodes 160 with the contacts 170 (or other electrodes 160). The micro-antenna 661 is embedded in the metal layer of the MEMS film 150. The micro-antenna 661 is serpentine in shape and is designed in order to be highly efficient at the chosen transmission frequencies.

Figure 17:
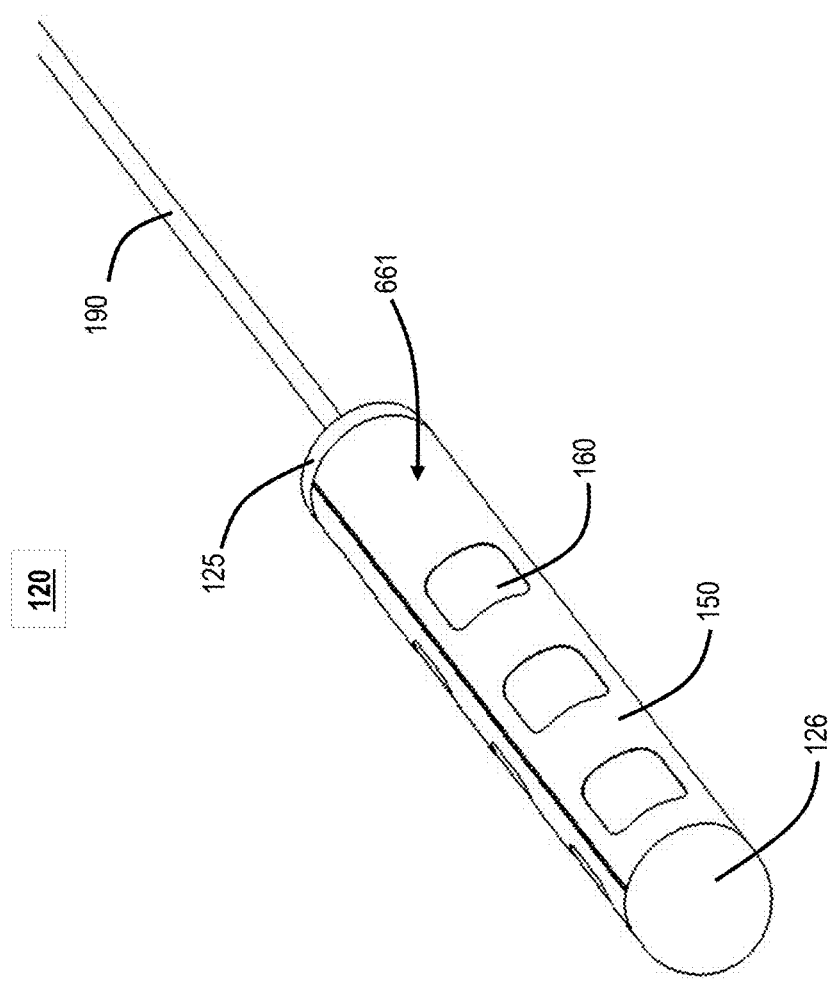

FIG. 17 illustrates a perspective view of an example leadless stimulator 100 with a micro-antenna 661. The MEMS film 150 can be rolled into a cylindrical shape. The MEMS film 150 can then be over-molded to create a capsule body 125. In some implementations with a micro-antenna 661, the tether 190 does not include antenna wires, and the tether 190 is used for the extraction of the leadless stimulator 100 from a patient after implantation. In some implementations, the tether 190 is embedded within the distal tip 126. Having the tether 190 run through the length of the body can reduce the chance of the tether 190 breaking free of the stimulation capsule 120.

Figure 18:
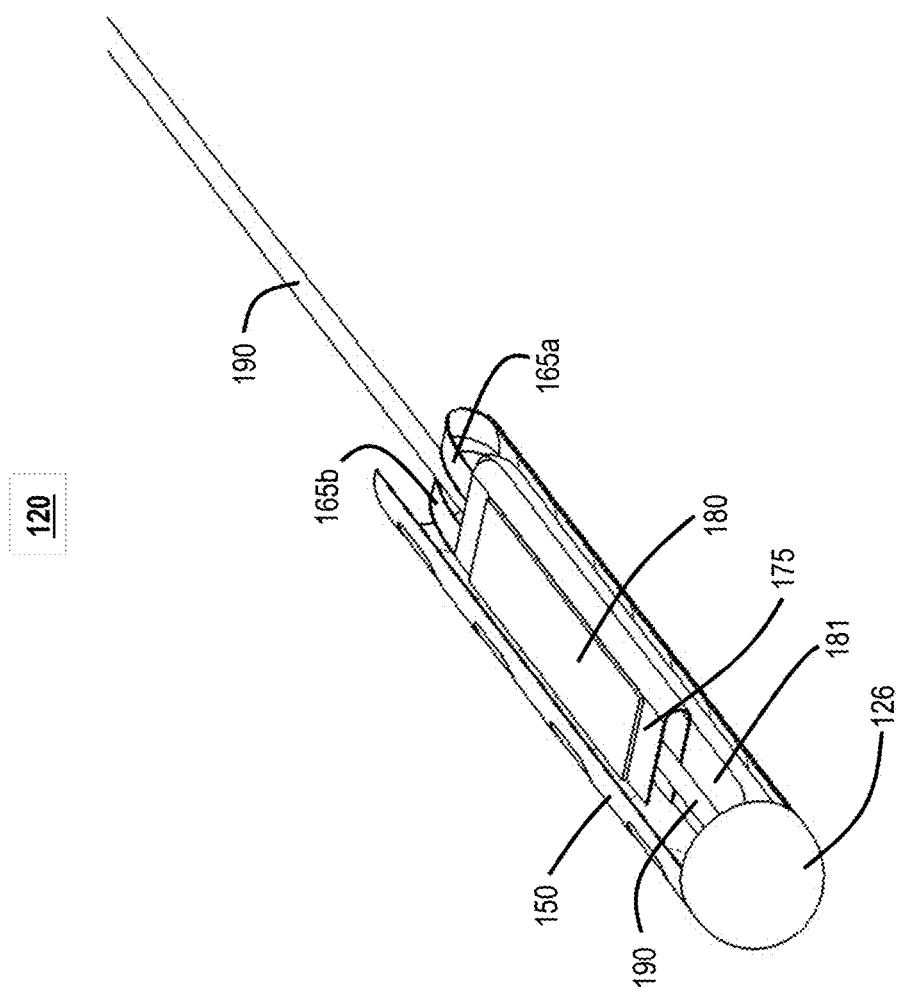
FIGS. 18 and 19 illustrate a cutaway view of an example leadless stimulator with micro-antenna.
Figure 19:
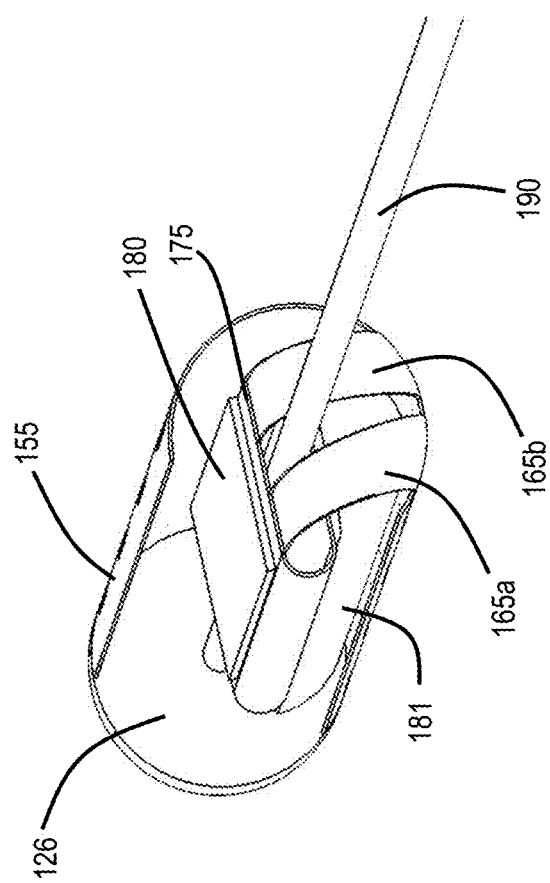

FIGS. 18 and 19 illustrate a cutaway view of an example leadless stimulator 100 with micro-antenna 661. As discussed above in relation to FIG. 17, the tether 190 can be coupled to the distal tip 126. FIG. 18 illustrates that the tether 190 passes through the body of the stimulation capsule 120 and is coupled with the distal tip 126. The ribbon cable 165 is divided into two parts (ribbon cable 165A and ribbon cable 165B) to facilitate the passage of the tether 190 through the capsule body 125. As illustrated in FIG. 19, the tether 190 can pass between the two parts of the ribbon cable 165. FIGS. 18 and 19 also illustrate the placement of the power supply 181. In some implementations, the power supply 181 is a battery. The power supply 181 may be recharged by the external programmer 500. Generally, the power supply 181 can have enough charge to provide stimulation for at least one day, or about 200 mAh, and in some implementations up to several weeks, or around 2300 mAh.

FIGS. 20A and 20B illustrate the internal arrangement of an example leadless stimulator 100 with a micro-antenna. The contacts 170 of the ASIC 180 can be aligned with and bonded to the respective contacts 170 of the contact pad 175. The contacts 170 of the power supply 181 can be aligned with and bonded to the respective contacts 170 of the battery pad 684. In some implementations, the ASIC 180 (or other components) can be wire bonded to the MEMS film 150 through wire bonds. Referring to FIGS. 20A-20B, among others, the power supply 181 and the ASIC 180 are placed on opposite sides of the tether 190 as the tether 190 passes through the body of the stimulation capsule 120.

Figure 21:
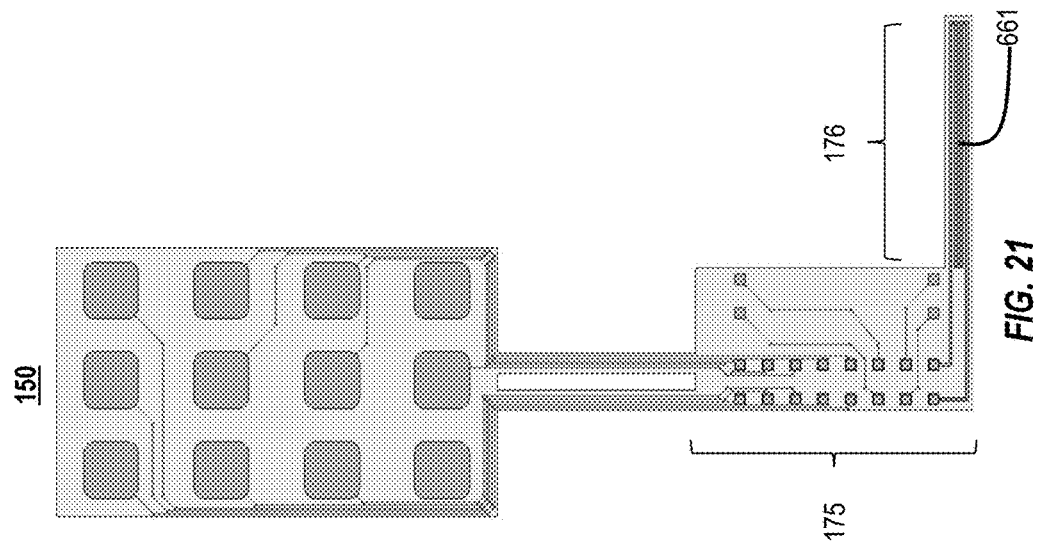
FIGS. 21 and 22 illustrate another example MEMS film with a micro-antenna.
Figure 22:
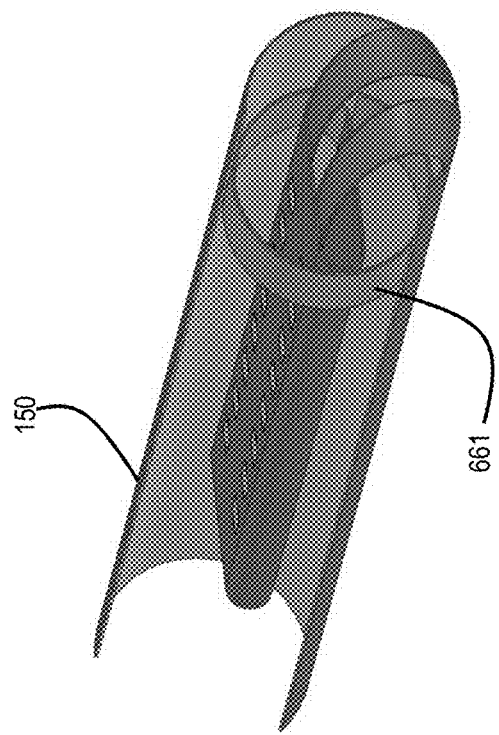

FIGS. 21 and 22 illustrate an example MEMS film 150 with a micro-antenna 661. As illustrated in FIG. 21, the MEMS film 150 includes a micro-antenna 661 on the distal portion of the contact pad 175. The micro-antenna 661 is disposed on a projection 176 from the contact pad 175. When forming the stimulation capsule 120, the micro-antenna 661 can be rolled to form a loop, which is housed within the rolled MEMS film 150. FIG. 22 illustrates a cutaway view of the stimulation capsule 120 with the rolled micro-antenna 661 located in the internal portion created by the rolled MEMS film 150.

FIGS. 23A-23M illustrate a cross-sectional view of an example thin-film micro-fabrication method for fabricating the MEMS film 150. The MEMS film 150 can be fabricated using a plurality of techniques and the below describe method illustrates one possible method for fabricating the MEMS film 150. The fabrication procedure can include a series of procedural steps in which various layers are deposited or removed (e.g., etched) to achieve a final form. The cross sections in FIG. 23A through FIG. 23M demonstrate the process steps to build a MEMS film 150.

In a first step illustrated in FIG. 23A, a carrier substrate 2301 is provided, such as a wafer composed of a crystalline material, such as silicon, or an amorphous material, such as a thermal shock resistant borosilicate glass or other suitable smooth supportive material. A first layer 2302, which can include one or more sub-layers, is applied to a surface of the wafer 2301. One of the sub-layers can be a sacrificial layer deposited on the wafer 2301, which is removed in a subsequent electrochemical etching step. In some implementations, the sacrificial sub-layer is preceded by another sub-layer, referred to as an underlayer, which can serve to form the electrochemical cell required to etch the sacrificial layer. The sacrificial sub-layer can be aluminum, or an alloy of aluminum such as AlSi, which has a smaller granularity, whereas the underlayer can be a TiW alloy such as Chrome or similar metal.

Referring to FIG. 23B, the next step in the fabrication process can include depositing a first polymeric layer 2305. The first polymeric layer 2305 can be deposited upon the sacrificial layer 2302 by MEMS processes such as, but not limited to, (i) spin coating a liquid polymer precursor such as Polyimide or Silicone precursor; (ii) depositing a polymer through chemical vapor deposition as is done with parylene-C; or (iii) laminating a polymer sheet onto the wafer. In some embodiments, the polymer layer 2305 is heated, or baked, to polymerize. In some implementations, the first polymeric layer 2305 includes polyamic-acid dissolved in NMP and spun onto the sacrificial layer 2302 in liquid form. The polymeric layer 2305 is heated into a imidized polyimide. The polymer in its cured form is between about 5 μm and about 15 μm thick.

Referring next to FIG. 23C, the deposition of a barrier layer. The barrier layer can serve both as a layer to aid the adhesion and durability of subsequent layers. The barrier layer can also serve as an ionic barrier, and limit ions from reaching the metal layers, which could compromise electrical performance. The barrier layer can also block humidity from reaching the interlayers and the metal layer, which could create short circuits and compromise electrical isolation.

In some implementations, the barrier layer is deposited onto the first polymeric layer 2305 by vapor deposition techniques such as chemical vapor deposition (CV) and plasma enhanced chemical vapor deposition (PECVD), or by sputtering techniques such as direct current (DC) or RF (Radio Frequency) sputtering. The barrier layer can include Silicon Nitride, Silicon Oxide, Silicon Carbide, Poly-Silicon, or Amorphous-Silicon. In some implementations, the barrier layer can also include other non-conductive materials, such as Titanium Dioxide or Titanium (III) Oxide. The final thickness of the barrier layer can range from about 100 nm to about 2 μm. In some implementations, the barrier layer is about 400 nm to about 600 nm, which can permit the barrier layer to be flexible enough to bend during subsequent assembly techniques.

Now referring to FIG. 23D, a metal layer 2315 can be deposited over the entire wafer on the surface of the barrier layer 2310. Subsequently, a photoresist layer 2317 can be deposited. The photoresist layer 2317 can be defined by exposing areas of the photoresist layer 2317 to ultra-violet light and developing those areas in a solvent. Thus, the exposed areas of the photoresist layer 2317 will be selectively removed and areas of the metal layer 2315 will be exposed. The areas of the metal layer 2315 covered by the photoresist layer 2317 can form the electrodes, traces, and other components of the final product that are within the metal layer.

The metal layer 2315 can include a variety of metals such as titanium, platinum, gold, and others metals used in neuromodulation. To improve adhesion of a metal layer 2315, the metal layer 2315 can be applied in layers. For example, the metal layer 2315 can be applied as a first layer, such as titanium, then a middle layer, such as platinum, and finally an upper layer, such as titanium. This tri-layer metal structure can improve adhesion below and above the platinum layer by using the titanium as an adhesion layer to the barrier layer. The typical thicknesses for the adhesion layer of titanium can be between about 20 nm and about 100 nm or between about 25 nm and about 75 nm. Typical thicknesses for the platinum layer can be between about 200 nm and about 400 nm or between about 250 nm and about 350 nm.

FIG. 23E illustrates the process after the etching of the metal layer 2315. As illustrated, the metal layer 2315 can be locally removed in the areas that were not covered by the photoresist 2317. In some implementations, etching of the metal layer is performed in a plasma etcher such as a Reactive Ion Etcher. In some implementations, titanium and platinum can be etched with chlorine gas. After the etching process is finished, the photoresist layer 2317 can be removed using a solvent.

Another method to deposit and define the metal layer is using the so-called "lift off" technique. In this method the photoresist layer can be deposited onto the barrier layer 2310 first. The photoresist layer can be defined using photolithography. The metal layer 2315 can then be deposited through this "lift off" mask, and the remaining photoresist removed in a solvent. In this method the metal layer is transferred onto the barrier layer without the need of plasma etching and may have some process costs and speed advantages.

Referring next to FIG. 23F, a deposition of a second barrier layer 2320 is performed. The second barrier layer can be deposited using the same techniques as the first barrier layer 2310. The second barrier layer 2320 can be the same thickness, or a different thickness as the first barrier layer. In some implementations, the second barrier layer is optional. The second barrier layer 2320 and the first barrier layer 2310 can substantially surround the metal layer 2315, rendering it electrically isolated. In order to etch and define the first and second barrier layer 2310 and 2320, respectively, a second photoresist layer 2327 is deposited and photolithographically defined with clean room techniques.

The two barrier layers are etched, as illustrated in FIG. 23G. The barrier layers can be etched using a plasma etch. An example of an etching process would be a reactive ion etching using a tetrafluoromethane gas, (CF4). The second photoresist layer 2327 can be removed using a solvent dissolution.

FIG. 23G illustrates that the edges of the barrier layers 2310 and 2320 are defined, but the etch does not reach the metal layer 2315. This is optional, and in some implementations the photolithography can include an opening above the metal layer 2315, which would result in exposing the metal layer 2315.

FIG. 23H illustrates the application of a second polymer layer 2330. The second polymer layer 2330 can be the same or a different polymer from the first polymer layer 2305, and it can be the same or a different thickness.

FIG. 23I illustrates the deposition of a third photoresist 2337, which can form the etching perimeter of the first and second polyimide layers 2305 and 2330, respectively. In some implementations, prior to the applying the third photoresist 2337, a sacrificial layer, such as Silicon Dioxide or Silicon Nitride, is deposited in order to serve as an etch mask for the polyimide etch. For example, a silicon dioxide layer of thickness of about 500 nm can be deposited, which will serve as the etch mask for the process.

FIG. 23J illustrates the result of an oxygen plasma etching of the first and second polyimide layers 2305 and 2330, respectively. If applied, the silicon dioxide layer can be removed through an additional etch.

FIG. 23K illustrates the deposition of a fourth photoresist layer 2347. The fourth photoresist layer 2347 does not cover part of the metal layer 2315. The opening 2332 maintained is designed to create a region for a gold layer to grow.

FIG. 23L illustrates the galvanic growth of a thick gold layer 2350 into the opening 2332. In some implementations, the gold layer 2350 is achieved by connecting the metal traces in the wafer to a perimetric metal band that allows an electrical connection between the edge of the wafer and the metal opening 2332. When immersed in a galvanic bath and a current applied, the gold will grow on the metal layer 2315 using the metal layer 2315 as the seed layer for galvanic growth. In some implementations, the gold layer 2350 is about 2 μm to about 20 μm thick. The fourth photoresist layer 2347 can be removed using a solvent.

FIG. 23M illustrates the removal of the MEMS film from the wafer 2301. The removal of the fourth photoresist layer 2347 exposes the electrode opening 2333. The MEMS film can be removed from the wafer 2301 by the removal of the sacrificial layer 2302 using electrochemically etching.

Removal of the sacrificial layer 2301 frees the underside of the MEMS film from the wafer 2301. In some implementations, the sacrificial layer 2301 is removed by placing the wafer in a saline bath with a high NaCl concentration. A platinum electrode also placed in the bath can be used as a reference, and a voltage can be applied to the aluminum layer with respect to the platinum electrode. The electrochemical cell created by the aluminum and TiW etches the aluminum—separating the MEMS film from the wafer 2301.

When the MEMS wafer is completed, and the individual devices have been removed, they still require several process steps before being assembled into the cylindrical shape that is required.

Figure 23N:
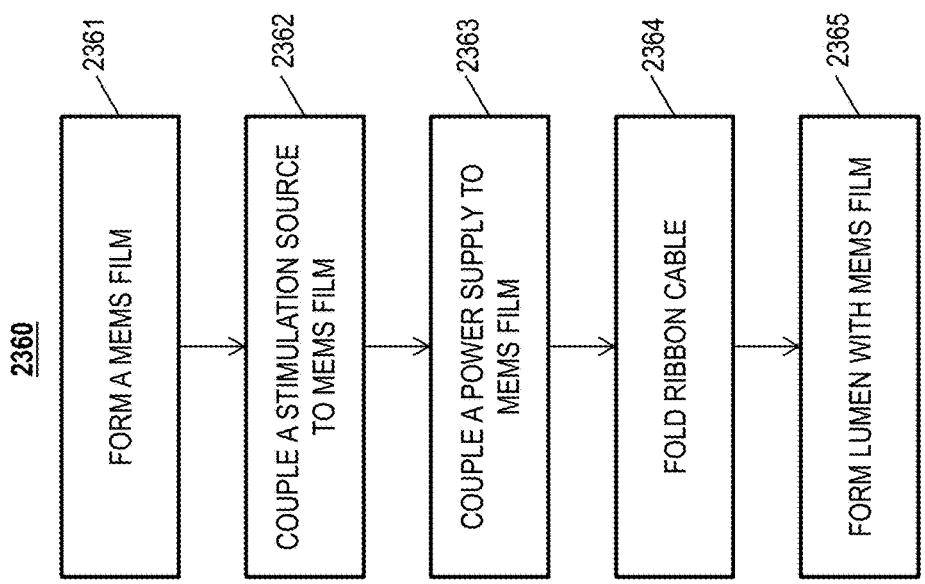
FIG. 23N illustrates an example method for forming the thin-film of FIGS. 23A-23M into a leadless stimulator.

FIG. 23N illustrates a method 2360 for manufacturing a leadless stimulator. At step 2361, a MEMS film is formed. The method for forming the MEMS film is described above in relation to FIGS. 23A-23M. In general, the MEMS film is formed as a planar film. The MEMS film can include a plurality of electrodes and a ribbon cable that extends from the distal end of the MEMS film.

At step 2362, a stimulation source is coupled with the MEMS film. Referring to FIG. 8, the stimulation source may be a component of an ASIC 180. The stimulation source (or ASIC 180) can include a plurality of contacts 170. The ribbon cable can also include a plurality of contacts 170. As illustrated in FIG. 8, the contacts 170 of the ASIC 180 can be coupled with the contacts 170 of the ribbon cable. Coupling the contacts 170 of the ASIC 180 with the contacts 170 of the ribbon cable can enable an electrical connection between the ASIC 180 and one or more electrodes.

Referring again to FIG. 23N, at step 2363, a power supply is coupled with the MEMS film. As illustrated in FIGS. 20A and 20B, a power supply 181 can be coupled with the MEMS film. The power supply can include a plurality of contacts, through which an electrical connection is established with the MEMS film. In some implementations, the power supply is coupled to the same face of the ribbon cable as the stimulation source, and in other implementations the power supply is coupled with a face opposite to the face the stimulation source is coupled. In some implementations, other circuitry such as recording circuitry, control circuitry, or other ASICs can be coupled with the ribbon cable.

At step 2364, the ribbon cable is folded toward a face of the MEMS film. As illustrated in FIG. 12, the ribbon cable 165, with the coupled stimulation source and power supply, are folded toward a face of the MEMS film. The MEMS film can include two primary faces. The first face includes the plurality of electrodes and the second face is the opposite face of the MEMS film. As illustrated in FIG. 12, the ribbon cable 165 is folded toward the second face of the MEMS film.

At step 2365, the MEMS film is formed into a lumen. Also as illustrated in FIG. 12, the sides of the MEMS film are formed around the portion of the ribbon cable to which the stimulation source and power supply are coupled. The formed MEMS film defines a lumen, in which the stimulation source and power supply are disposed. The MEMS film can be heat formed such that the MEMS film maintains it shape after the forming process. In some implementations, the lumen defined by the formed MEMS film is filled with an encapsulating epoxy. The encapsulating epoxy can provide structural stability to the stimulation capsule and can also electrically isolate the electrical components disposed within the lumen.

Figure 24:
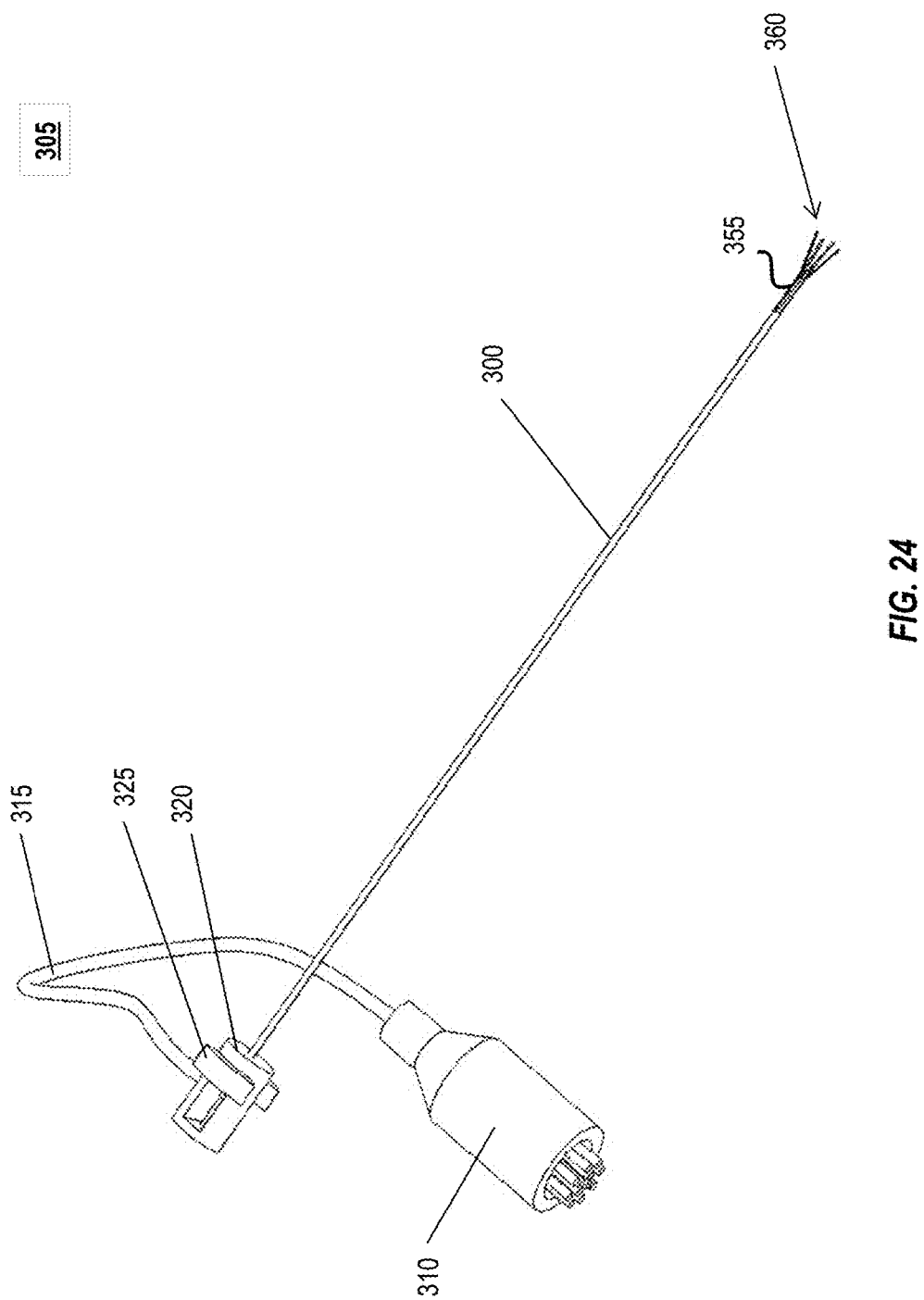
FIG. 24 illustrates an example deployment system of the leadless stimulator system of FIG. 1.

FIG. 24 illustrates an example deployment system 305. The deployment system 305 is used to implant the leadless stimulator 100. The deployment system 305 includes a guide tube 300. At the proximal end, deployment system 305 can include a connection plug 310. The connection plug 310 enables electrical connections between the deployment system 305 and a controller or recording device used during the implantation of the leadless stimulator 100. The connection plug 310 is coupled with the other components of the deployment system 305 via the connection cable 315. The connection cable 315 can include electrical conductors, in the form of wires or traces, which electrically couple the distal electrodes 355 to the connection plug 310. The deployment system 305 also includes a depth stop 320 to enable the surgeon to couple the deployment system 305 with stereotactic equipment. In some implementations, the depth stop 320 may also house pre-amplifier circuitry to improve the signals coming from the distal electrodes 355. The depth stop 320 also includes a deployment handle 325. The deployment handle 325 may be pushed up or down by the surgeon to deploy or retract, respectively, the distal legs 360. In FIG. 24, the distal legs 360 are illustrated in the deployed state. The body of the deployment system 305 includes guide tube 300. The guide tube 300 can include a leg support stent that is disposed around an inner cylinder. A MEMS film can be disposed around the leg support stent to form the distal legs 360.

FIGS. 25A and 25B illustrate a cut away and perspective view, respectively, of the distal end of the guide tube 300. The inner cylinder 330 includes a central lumen 337. The distal most end of the inner cylinder 330 includes a guide 339. The guide 339 can mate with the proximal end of the stimulation capsule 120.

In some implementations, the external diameter of the inner cylinder 330 is between about 0.5 mm and about 3 mm, between about 1 mm and about 2 mm, or about 1 mm and 1.5 mm. In some implementations, the internal diameter of the central lumen 337 is between about 0.25 mm and about 1.5 mm or between about 0.5 mm and about 1 mm. The internal diameter of the central lumen 337 can enable the insertion of the tether 190 and the antenna 200. The guide 339 can have a slightly larger external diameter when compared to the inner cylinder 330. For example, the diameter of the guide 339 may be about 1.5 mm when the outer diameter of the inner cylinder 330 is about 1 mm. The guide 339 can either be a separate piece, which is later coupled with the inner cylinder 330, or the guide 339 can be machined from the same stock material as the inner cylinder 330. The inner wall 340 of the guide 339 can surround the leadless stimulator 100, and the outer wall 341 of the guide 339 can be used to guide the below described distal legs 360 during deployment. In some implementations, the inner cylinder 330 includes a metal, such as surgical stainless steel, and in other implementations, the inner cylinder 330 can include a polymer or other MRI compatible material such as a ceramic or titanium oxide.

Figure 26A:
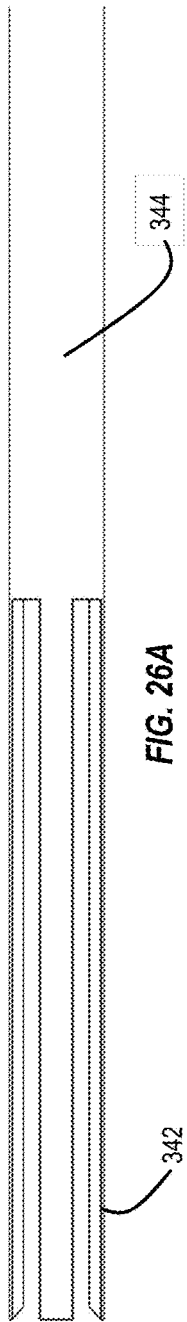
FIGS. 26A-26C illustrate an example leg support stent for the deployment system of FIG. 24.
Figure 26B:
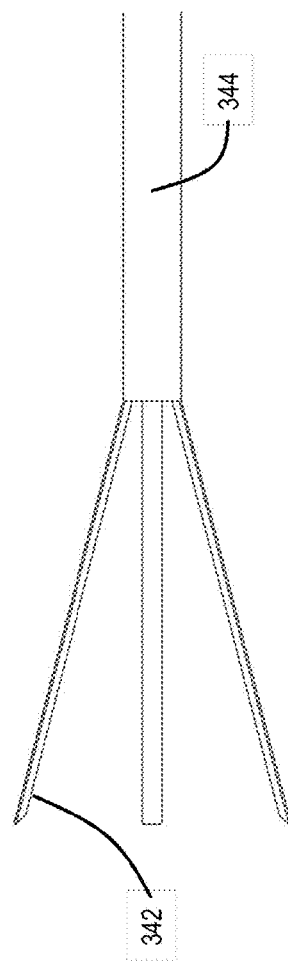
Figure 26C:
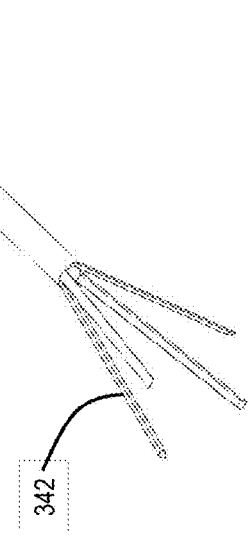

FIGS. 26A-26C illustrate an example leg support stent 344. In some implementations, the external diameter of the leg support stent 344 is between about 0.5 mm and about 3 mm, between about 1 mm and about 2 mm, or about 1 mm and 1.85 mm. The internal diameter of the leg support stent 344 can be at least the external diameter of the inner cylinder 330, such that the leg support stent 344 can be disposed around the inner cylinder 330. The leg support stent 344 can include leg supports 342 at distal end of the leg support stent 344. As illustrated, the leg support stent 344 includes four leg supports 342. In some implementations, the leg supports 342 can be flexible enough to expand with the typical forces that can be applied by hand. FIGS. 26B and 26C illustrate the expanded leg supports 342. In some implementations, the leg supports 342 of the leg support stent 344 slide distally along the inner cylinder 330. When the leg supports 342 come into contact with the outer wall 341 of the guide 339, the outer wall 341 can cause the leg supports 342 to expand.

Figure 27:
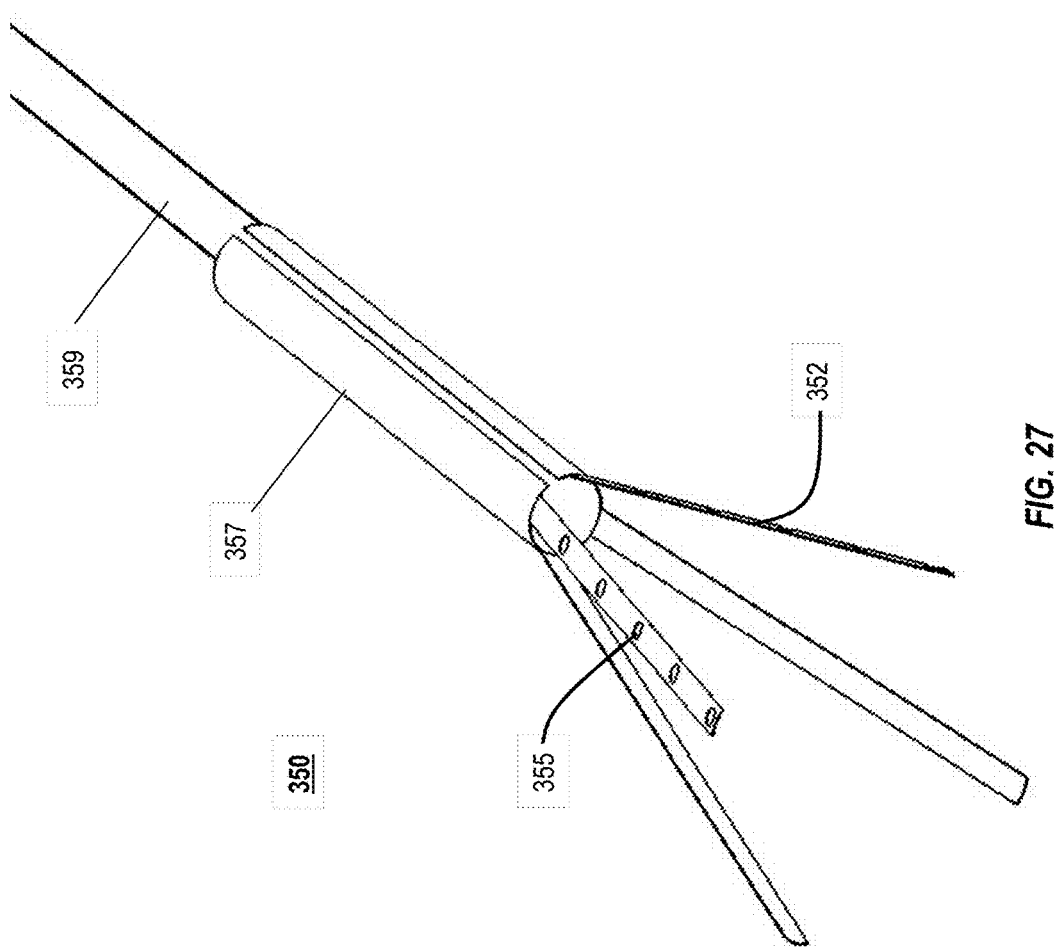
FIG. 27 illustrates an example MEMS film for the deployment system of FIG. 24.

FIG. 27 illustrates an example MEMS film 350 that can be coupled around the leg support stent 344. The MEMS film 350 can include legs 352. As illustrated the MEMS film 150 includes four legs 352. In some implementations, the legs 352 are between about 5 mm and about 15 mm or between about 7 and about 12 mm in length. The legs 352 can be about 0.25 mm to about 1 mm in width. In some implementations, the legs 352 are about the same length and width as the leg supports 342. One or more surfaces of the legs 352 can include a plurality of microelectrode elements 355. As illustrated, each leg 352 includes five microelectrode elements 355. In some implementations, different legs 352 can include a different number of microelectrode elements 355. Each microelectrode elements 355 can include between 1 and about 10 microelectrode elements 355. In some implementations, the legs 352 include more than 10 microelectrode elements 355. The microelectrode elements 355 can be circular or rectangular in shape and have a diameter between about 100 µm and about 1000 µm, or between about 200 µm and about 700 µm, or between about 300 µm and about 500 µm. The MEMS film 350 can also include a shoulder 357 that can be coupled around the leg support stent 344. The MEMS film 350 can further include a tether 359, which carries traces from the microelectrode elements 355 to the proximal end of the guide tube 300. In some implementations, there is one trace for each microelectrode elements 355 and in other implementations one or more microelectrode elements 355 may be coupled with the same trace.

Figure 28A:
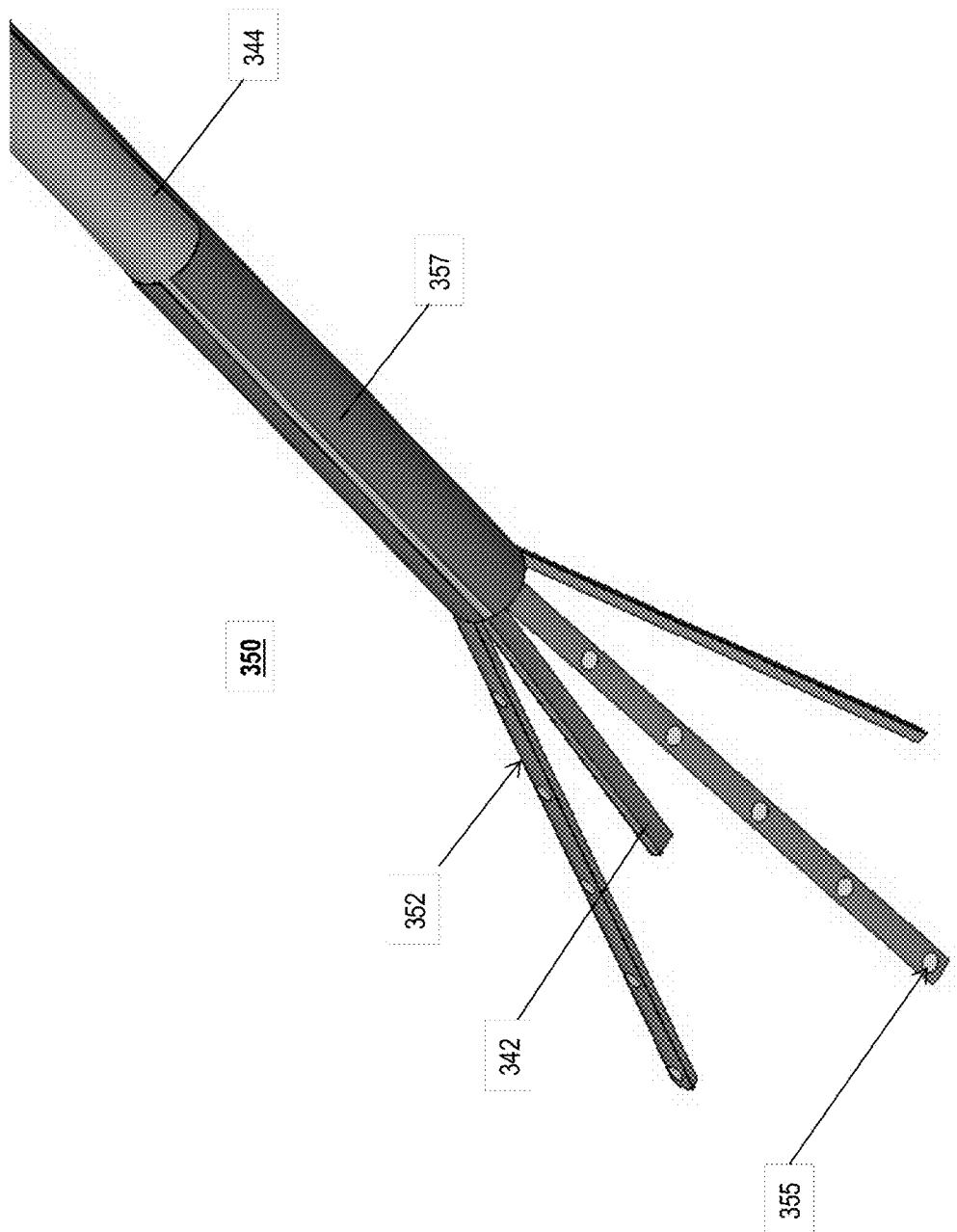
FIGS. 28A and 28B illustrate the MEMS film coupled with the leg support stent.
Figure 28B:
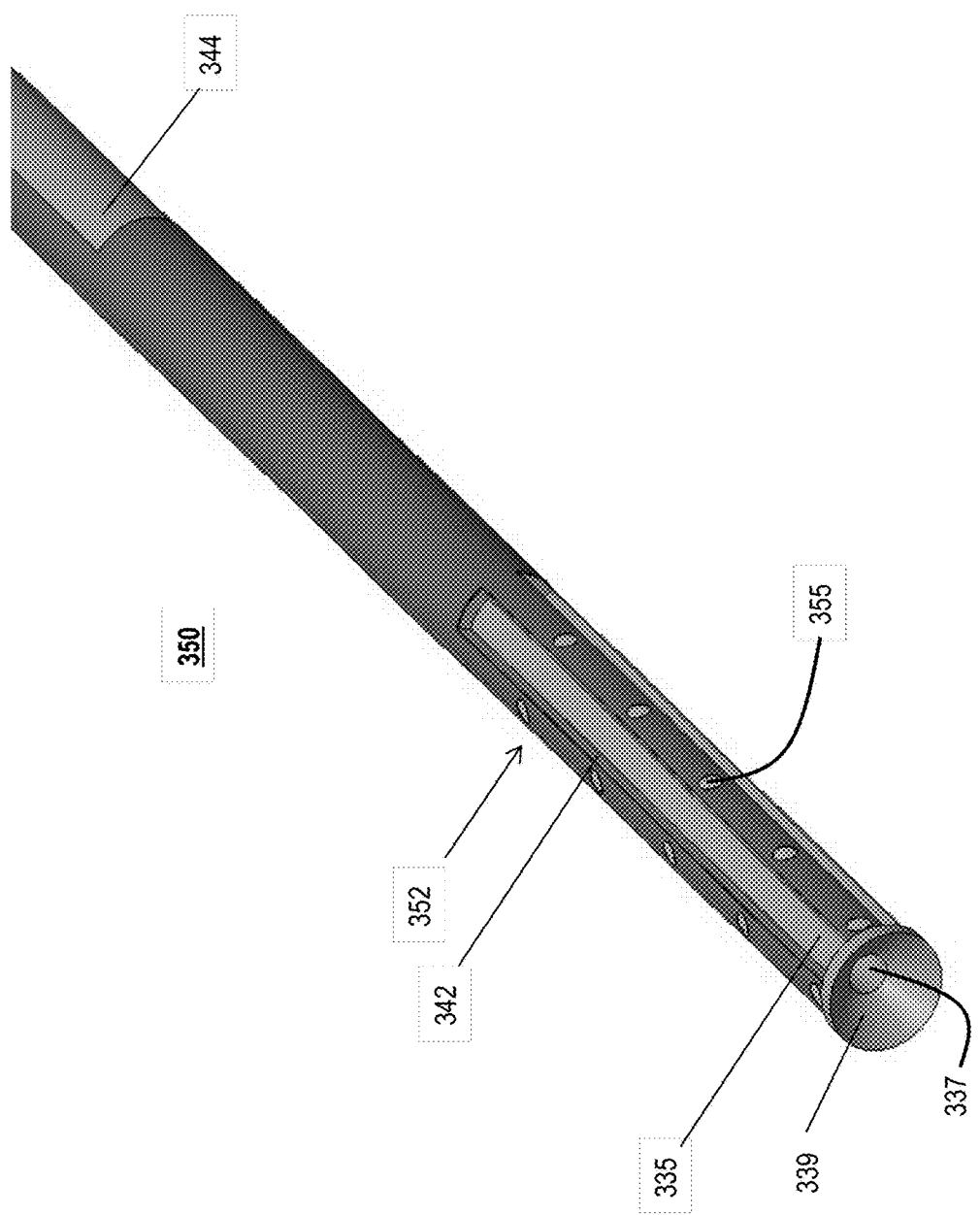

FIG. 28A illustrates the MEMS film 350 coupled with the leg support stent 344. The MEMS film 350 can be coupled to the leg support stent 344 with glue or pressure bonding. The legs 352 are aligned and coupled with the leg supports 342. FIG. 28B illustrates the MEMS film 150 coupled with the leg support stent 344, with the leg supports 342 in the retracted state.

Figure 29A:
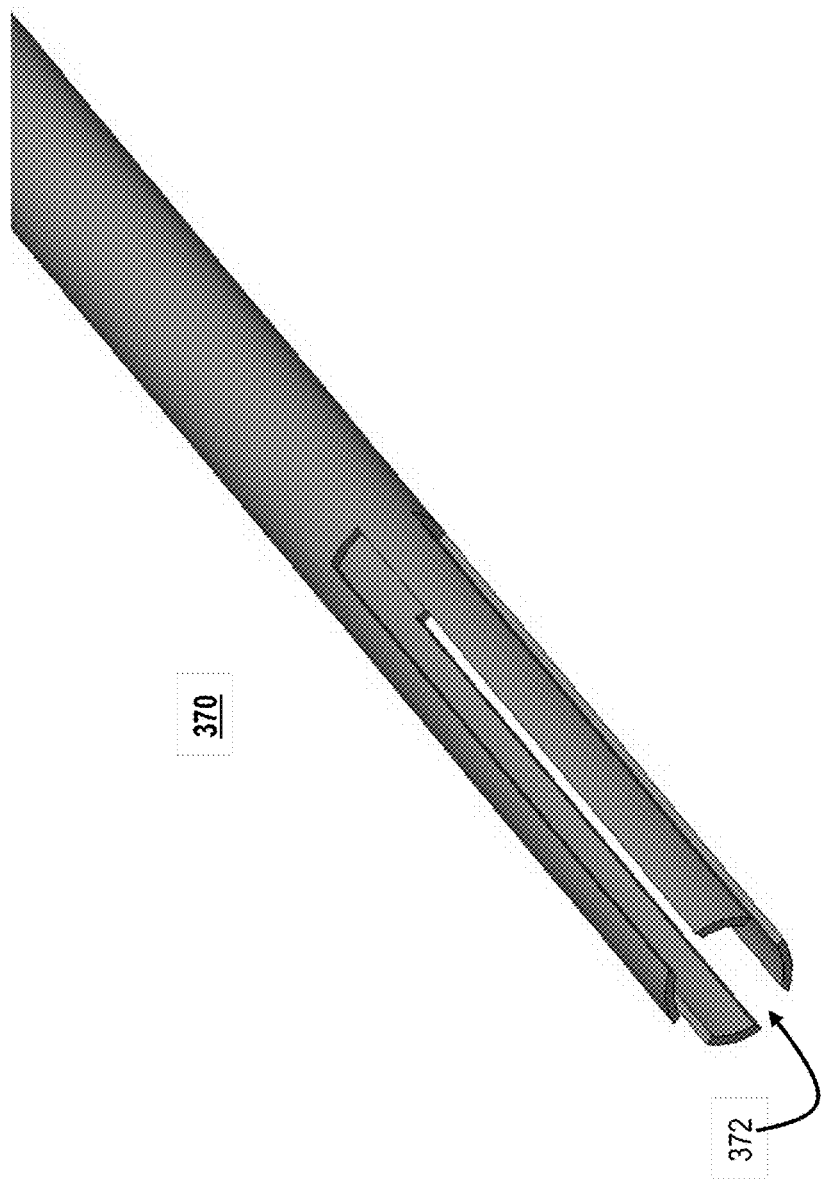
FIGS. 29A and 29B illustrate an example outer tube of the guide tube.

FIG. 29A illustrates an example outer tube 370 of the guide tube 300. The distal end of the outer tube 370 can include leg gaps 372. The outer tube 370 can enable the leg supports 342 to fit within the leg gaps 372. In some implementations, the outer tube 370 can have an outer diameter between about 0.5 and about 2.5 mm. In some implementations, the wall thickness of the outer tube 370 is about 0.2 mm. The outer tube 370 is generally implemented in a medical grade Stainless Steel such as 316, or could be implemented in a polymer such as polyimide to promote improved MRI Compatibility.

Figure 29B:
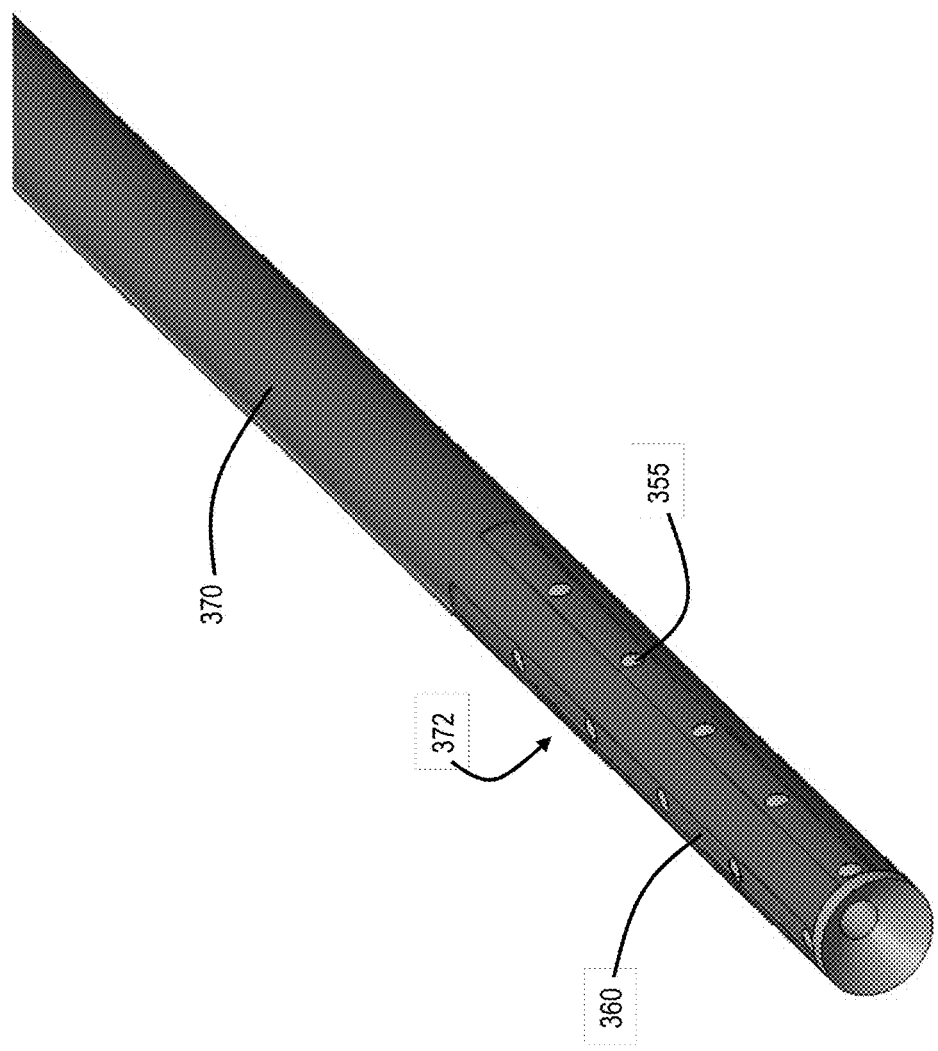

FIG. 29B illustrates an example guide tube 300 with an outer tube 370 in place. The outer tube 370 can be placed concentrically over the MEMS film 350 and the leg support stent 344. As illustrated in FIG. 29B, the assembly guide tube 300 exposes the microelectrode elements 355 through the leg gaps 372 of the outer tube 370. In some implementations, exposure of the microelectrode elements 355 through the leg gaps 372 enables the microelectrode elements 355 to record neural activity as the guide tube 300 descends into brain tissue. In some implementations, the guide tube 300 can perform neural recording to enable a surgeon to identify the guide tube's location with a patient's tissue.

Figures 30A, 30B:
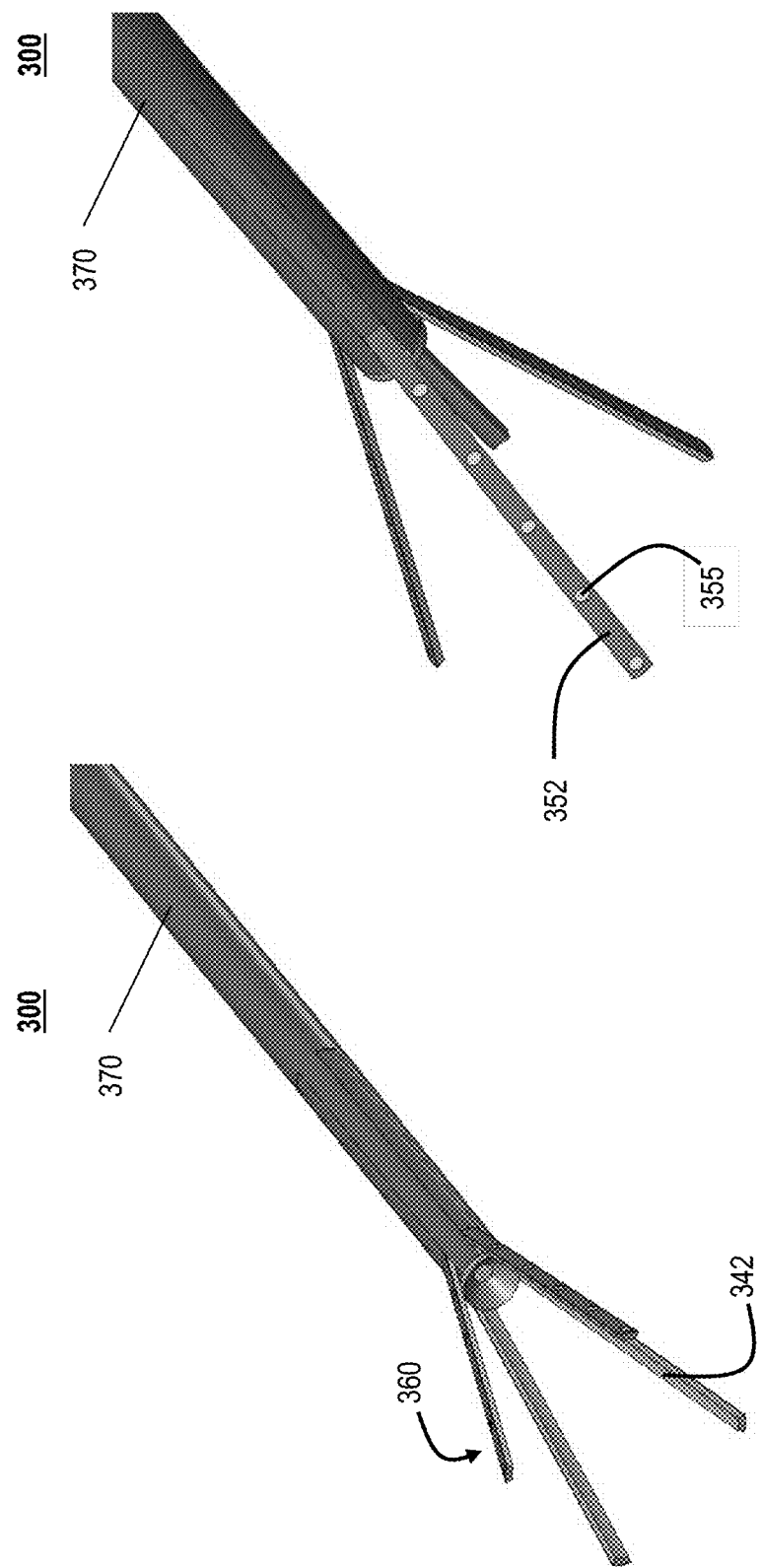
FIGS. 30A and 30B illustrate two views of the guide tube with the distal legs deployed.

FIGS. 30A and 30B illustrate two views of the guide tube 300 with the distal legs 360 deployed. In some implementations, when reaching a target site within the tissue, the distal legs 360 can be deployed by a surgeon to perform neural recording. Each of the distal legs 360 can include a plurality of microelectrode elements 355. In the illustrated example of FIGS. 30A and 30B, each of the four distal legs 360 include five microelectrode elements 355, for a total of twenty recording and stimulation sites. In some implementations, the guide tube 300 can include more or fewer distal legs 360, each with more or fewer microelectrode elements 355.

Figures 31A, 31B:
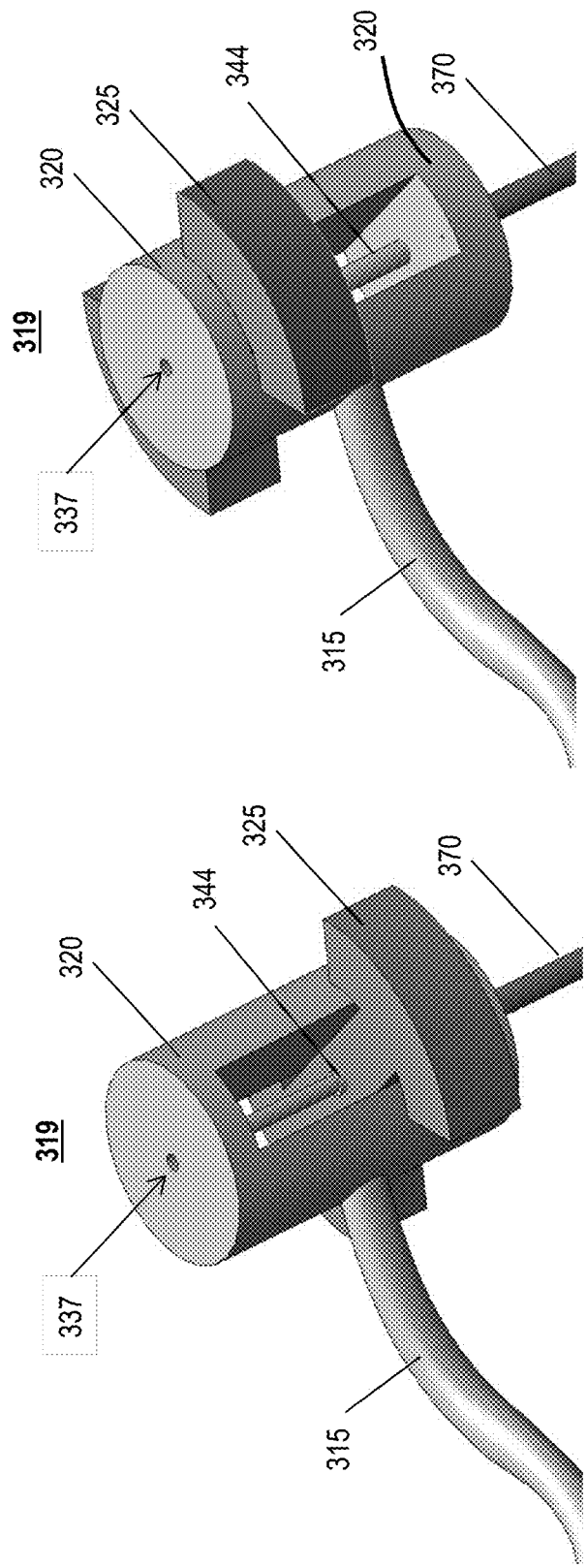
FIGS. 31A and 31B illustrate an example deployment mechanism for the deployment system of FIG. 24.

FIGS. 31A and 31B illustrate an example deployment mechanism 319. In some implementations, the deployment mechanism 319 can include a handle 325 that can be used to deploy the distal legs 360, as illustrated in FIGS. 30A and 30B. The leg support stent 344 can be attached to the deployment handle 325. Accordingly, movement of the deployment handle 325 can be translated into movement of the leg support stent 344, which results in the deployment or retraction of the distal legs 360. FIG. 31A illustrates the position of the deployment handle 325 when the distal legs 360 are in the deployed state, and FIG. 31B illustrates the position of the deployment handle 325 when the distal legs 360 are in the retracted state. The central lumen 337 is visible on the proximal end of the deployment mechanism 319. The deployment mechanism 319 can include depth stops 320 that can limit the movement of the deployment handle 325 in the proximal and distal directions.

FIGS. 32A and 32B illustrate the distal end of the example deployment system 305 coupled with the leadless stimulator 100. The deployment system 305 includes the guide tube 300 coupled with the leadless stimulator 100. The stimulation capsule 120 is exposed at the distal end of the guide tube 300. In some implementations, the proximal end 127 of the leadless stimulator 100 (hidden in FIGS. 32A and 32B) can couple with the guide 339 (hidden in FIGS. 32A and 32B) of the guide tube 300. When the leadless stimulator 100 is coupled with the guide tube 300, the guide tube 300 can be used to push the leadless stimulator 100 toward the target location in the tissue.

Figures 33A, 33B:
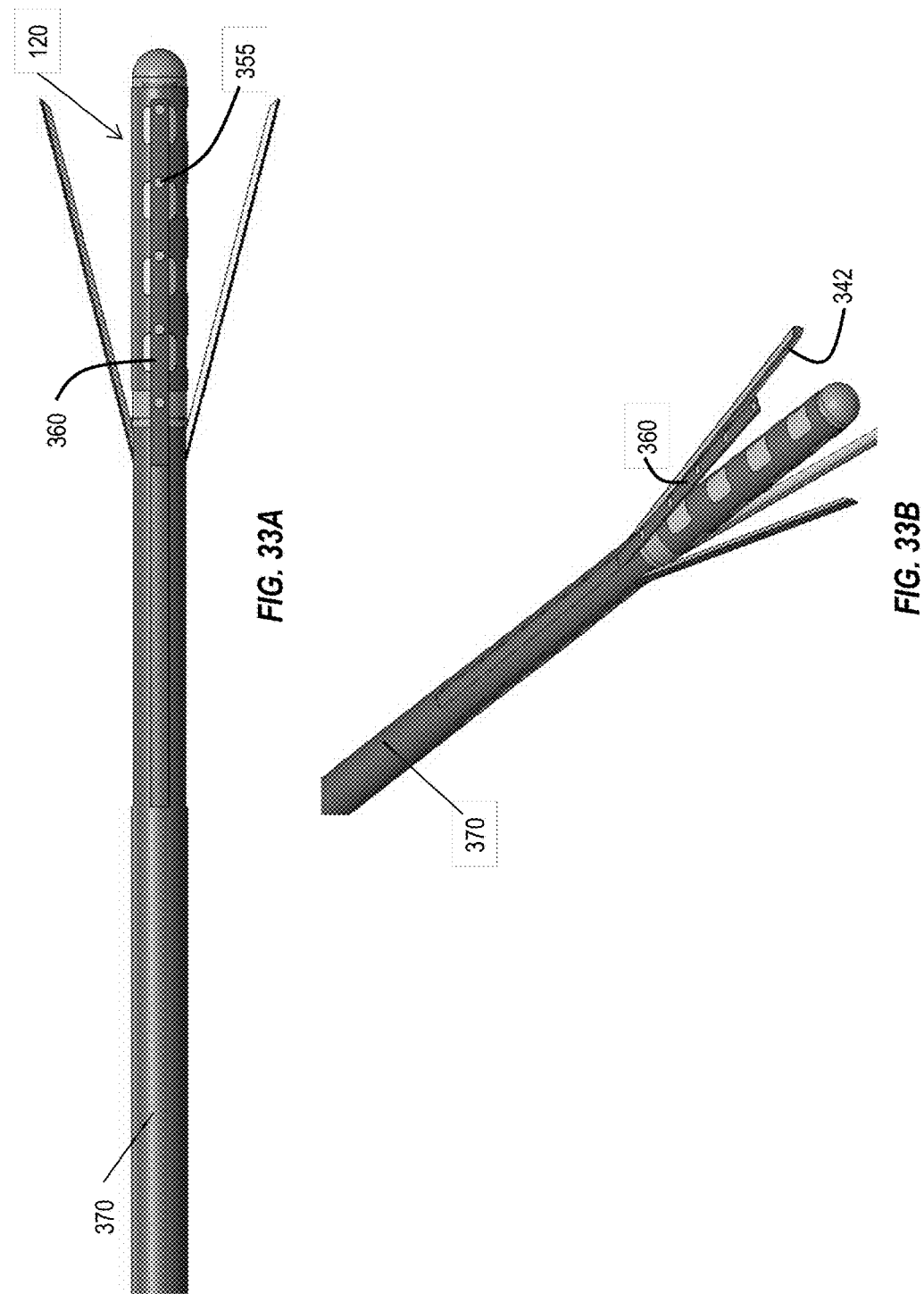
FIGS. 33A and 33B illustrate the distal end of the example deployment system of FIG. 24, with the distal legs deployed.

FIGS. 33A and 33B illustrate the distal end of the example deployment system 305, with the distal legs 360 deployed. In some implementations, when deployed, the distal legs 360 can enable the recording and stimulation of the region surrounding the stimulation capsule 120. In some implementations, the intra-operative recording and stimulation procedure can be used to further determine the final position of the leadless stimulator 100. In some implementations, the recording and stimulation procedure can be used to determine an improved stimulation and recording configuration for the leadless stimulator 100. For example, the procedure may be used to determine if a subset of the electrodes 160 of the leadless stimulator 100 should be used for recording and stimulating.

FIGS. 34A and 34B illustrate the distal end of the example deployment system 305, with the guide tube 300 and stimulation capsule 120 separated—for example, after the surgeon has begun to retract the deployment system 305 from the patient's tissue. In some implementations, the distal legs 360 are retracted and then the deployment system 305 can be retracted from the tissue, leaving, as illustrated in FIGS. 34A and 34B, the leadless stimulator 100 at the target location.

FIGS. 35-38 illustrate an example method of implanting the leadless stimulator 100. FIGS. 35A and 35B illustrate the leadless stimulator 100 in the preimplantation position. The leadless stimulator 100 is positioned above a craniotomy 1055 in a patient's skull 1050. The craniotomy exposes a portion of the brain 1060. In some implementations, the leadless stimulator 100 and deployment system 305 are lowered into place from the exterior of the patient using stereotactic implantation tools (not illustrated).

Figure 36A:
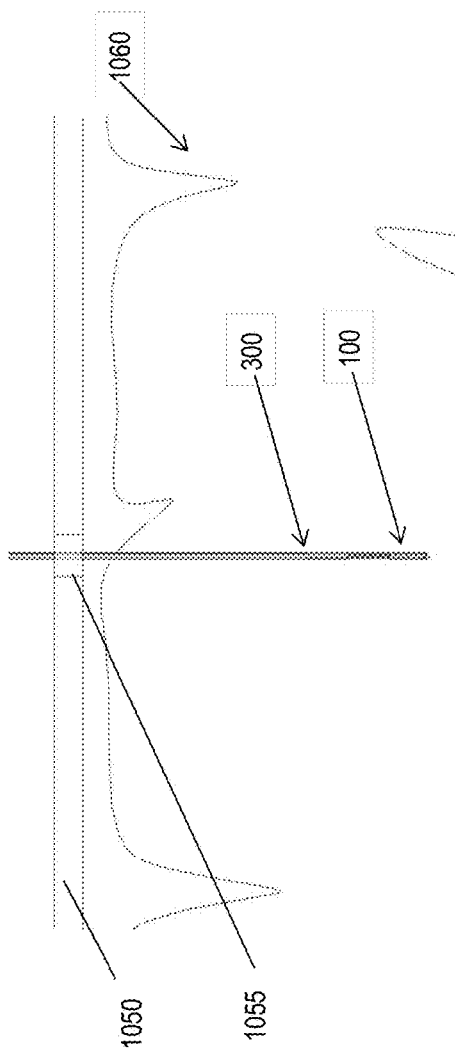
Figure 36B:
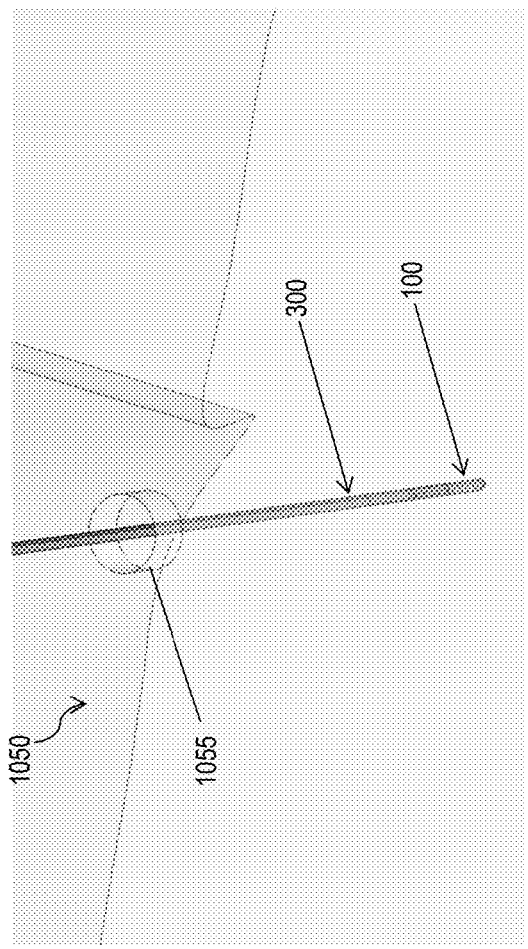

FIGS. 36A and 36B illustrate the positioning of the leadless stimulator 100 into the patient's brain 1060. Using the stereotactic implantation tools, the surgeon drives the deployment system 305 into the patient's brain 1060, which in turn pushes the leadless stimulator 100 into the position. In some implementations, the surgeon can record neural activity as with the deployment system 305 and leadless stimulator 100 as they are lowered toward the target location.

Figure 37A:
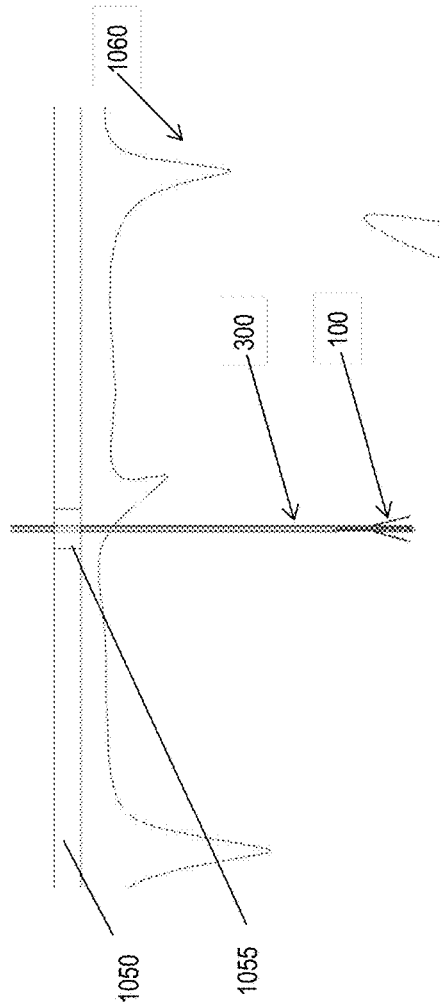
Figure 37B:
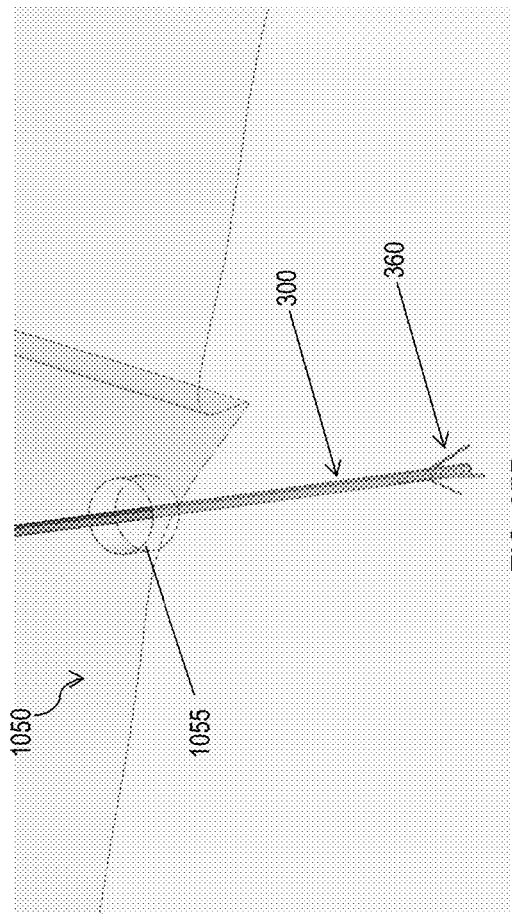

FIGS. 37A and 37B illustrate the deployment of the distal legs 360 of the leadless stimulator 100. In some implementations, the distal legs 360 are deployed to record neural activity when the leadless stimulator 100 is believed to be at the proper implantation location. The microelectrode elements 355 of the guide tube 300, and optionally the electrodes 160 of the leadless stimulator 100 can be used to record the neural activity of the implanted location. This procedure may be referred to as "targeting." Targeting procedure may include recording the electrical activity of the target anatomy using the microelectrode elements 355 and the electrodes 160. A signal processing software can record and display the neural activity to the neurosurgical team. Responsive to the recorded neural activity, the team may determine if the leadless stimulator 100 is placed in the proper anatomical location. In some implementations, the microelectrode elements 355 and the electrodes 160 can be used to stimulate the anatomical target in order to evoke a physiological response in the patient—for example, eye twitching or parasthesia. This procedure of neurophysiological recording and evoked patient responses can lead the neurosurgical team to determine the best placement of the leadless stimulator 100.

Figure 38A:
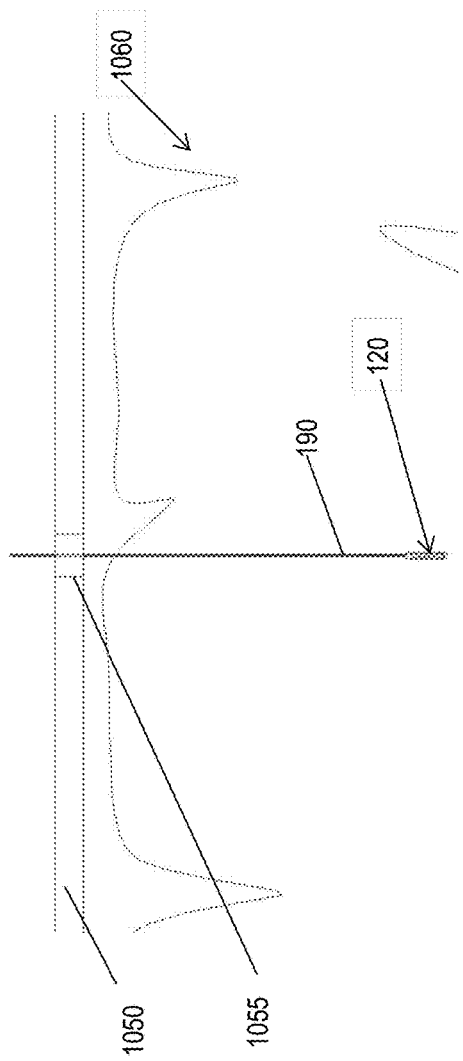
Figure 38B:
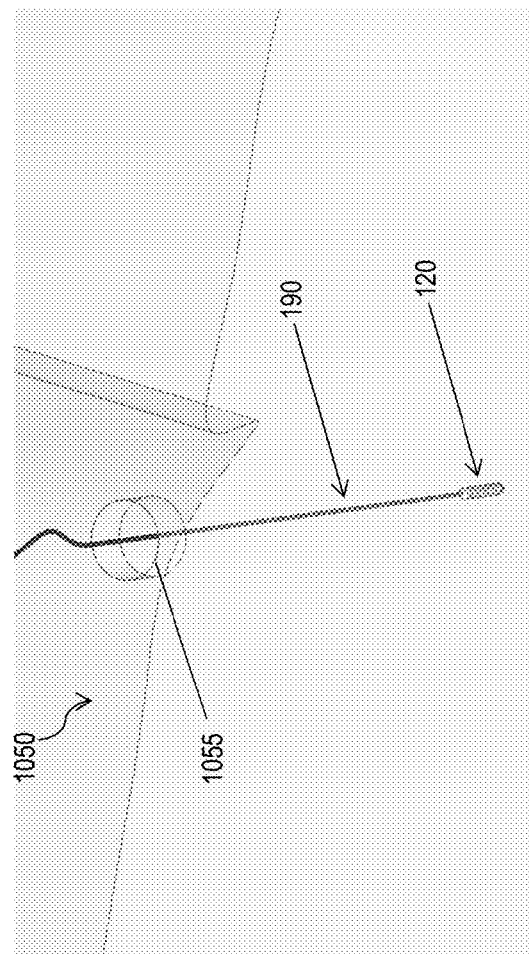

FIGS. 38A and 38B illustrate the placement of the leadless stimulator 100 after the retraction of the deployment system 305. Following the targeting procedure, the distal legs 360 can be retracted. The leadless stimulator 100 can be left in place and the deployment system 305 is retracted from the patient. As the deployment system 305 is retracted, the stimulation capsule 120 remains in place and is tethered with the antenna 200 by the tether 190. The antenna 200 may exit the patient through the craniotomy 1055. The surgeon may fill the craniotomy 1055 with surgical cement or bone paste, which can secure the antenna 200 in place. In some implementations, the antenna 200 is wound into a burr hole cover frame to secure and position the antenna 200.

Figure 40:
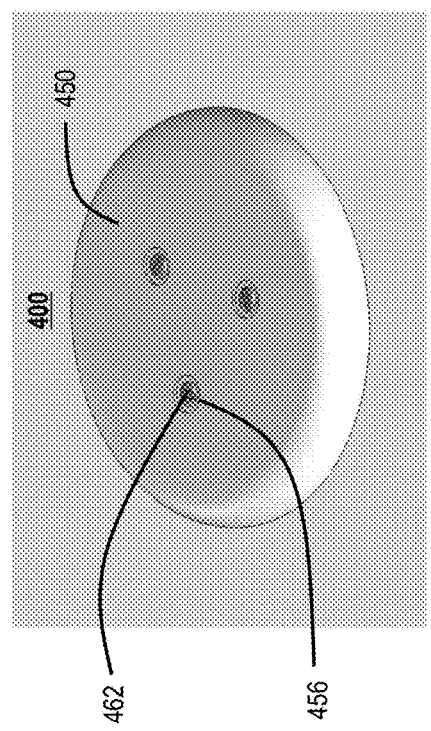
FIG. 40 illustrates a top view of the example burr hole cover frame after implantation into the craniotomy.

FIG. 39 illustrates a patient 1000 with a burr hole cover frame 400 in place. FIG. 40 illustrates a closer view of the example burr hole cover frame 400. The burr hole cover frame 400 can include a burr hole cover cap 450 that protects the antenna 200 and area of the skull where the craniotomy was performed. The burr hole cover frame 400 can also include a lower part 410. In some implementations, the burr hole cover cap 450 can be secured to the lower part 410 by the burr hole cover cap 450 clipping into the lower part 410. In another implementation, as illustrated in FIG. 40, the burr hole cover cap 450 can be secured to the lower part 410 by screws 462 through screw holes 456.

Figure 41:
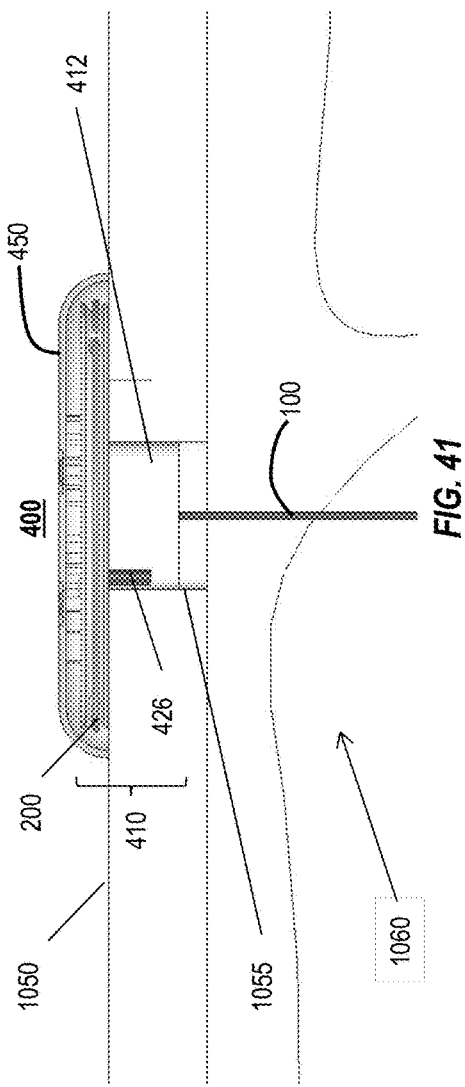
FIG. 41 illustrates a side view of the example burr hole cover frame after implantation into the craniotomy.

FIG. 41 illustrates a side view of the example burr hole cover frame 400 after implantation into the craniotomy 1055. The burr hole cover frame 400 can include the burr hole cover cap 450 coupled with the lower part 410. The lower part 410 can include a burr hole insert 412, through which the leadless stimulator 100 exits the patient. The burr hole insert 412 can fill the hole in the skull left by the craniotomy. The antenna 200 can wrap around the circumference of the lower part 410 to ensure the antenna 200 maintains a predetermined loop diameter. In some implementations, the lower part 410 is secured to the patient by one or more screws 462 or glue.

Figure 42C:
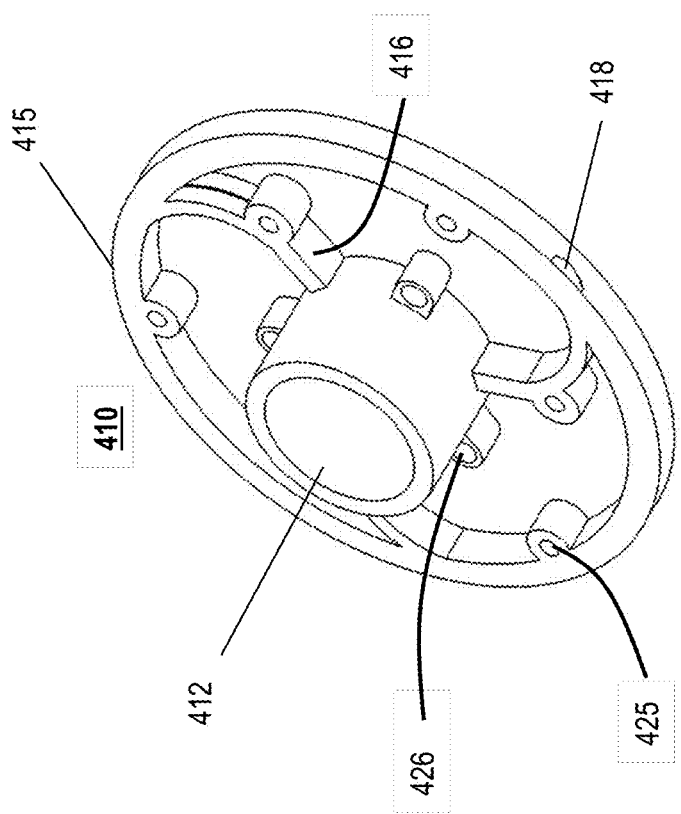

FIGS. 42A-42C illustrate the example lower part 410 of the burr hole cover frame 400. FIGS. 42A, 42B, and 42C illustrate side, top, and perspective views of the lower part 410, respectively. The lower part 410 can include a cartwheel frame 415. The cartwheel frame 415 can include an antenna notch 417 around the perimeter of the cartwheel frame 415. In some implementations, the antenna 200 is wound around the perimeter of the cartwheel frame 415 and lies within the antenna notch 417. The antenna notch 417 of the cartwheel frame 415 can include a hole 418 from which the antenna 200 can exit the central lumen 411 of the lower part 410 to be wrapped around the perimeter of the cartwheel frame 415. The lower part 410 can also include a burr hole insert 412 that is inserted into the craniotomy 1055 of the patient. The burr hole insert 412 is about 8 mm in diameter in some implementations, but can range from 3 mm to 15 mm in diameter. The burr hole insert 412 is about 4 mm deep, but can range from 1 mm to 8 mm deep in some implementations.

FIG. 42B illustrates that the lower part 410 can include securing screw holes 425 on the inner perimeter of the cartwheel frame 415 and on the spokes 416 of the lower part 410. The securing screw holes 425 can be used to secure the burr hole cover frame 400 to the patient's skull by screwing screws through the securing screw holes 425 and into the patient's skull. The lower part 410 can also include screw holes 426 to secure the lower part 410 to the burr hole cover cap 450. In some implementations, the lower part 410 has a diameter 420 of about 25 mm. Generally, the diameter is equivalent to the most efficient antenna diameter for the chosen transmission frequency as described above.

FIGS. 43A, 43B, and 43C illustrate side, top, and perspective views of the burr hole cover cap 450, respectively. In some implementations, the burr hole cover cap 450 can protect the antenna 200 and the patient's brain after its exposure by the craniotomy. The burr hole cover cap 450 can include a smoothed edge 452. The smoothed edge 452 can reduce tissue erosion once implanted. The burr hole cover cap 450 can also include three securing screw holes 456 that can align with screw holes 426.

Figure 44B:
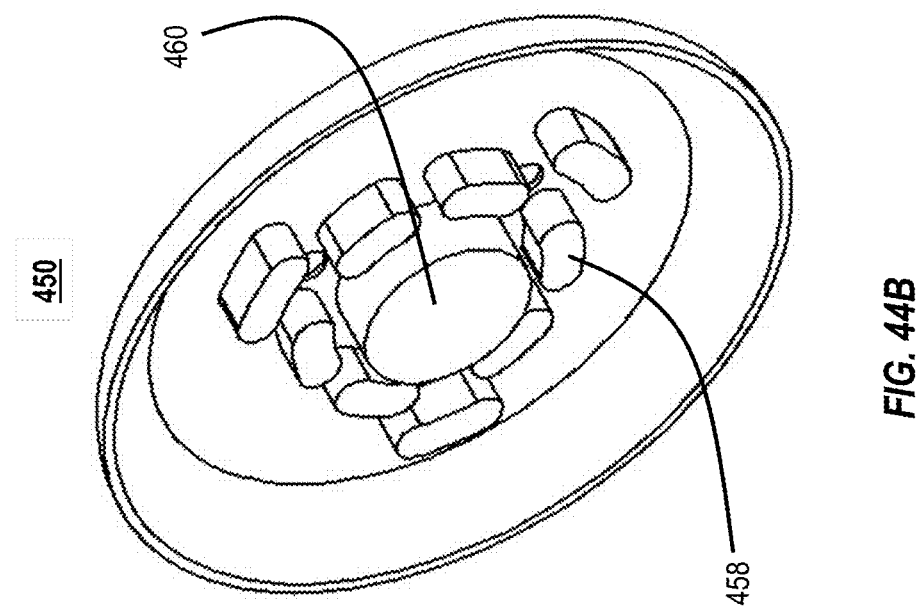
FIGS. 44A and 44B illustrate different views of the bottom-side of the burr hole cover cap from FIGS. 43A-43C.
Figure 44A:
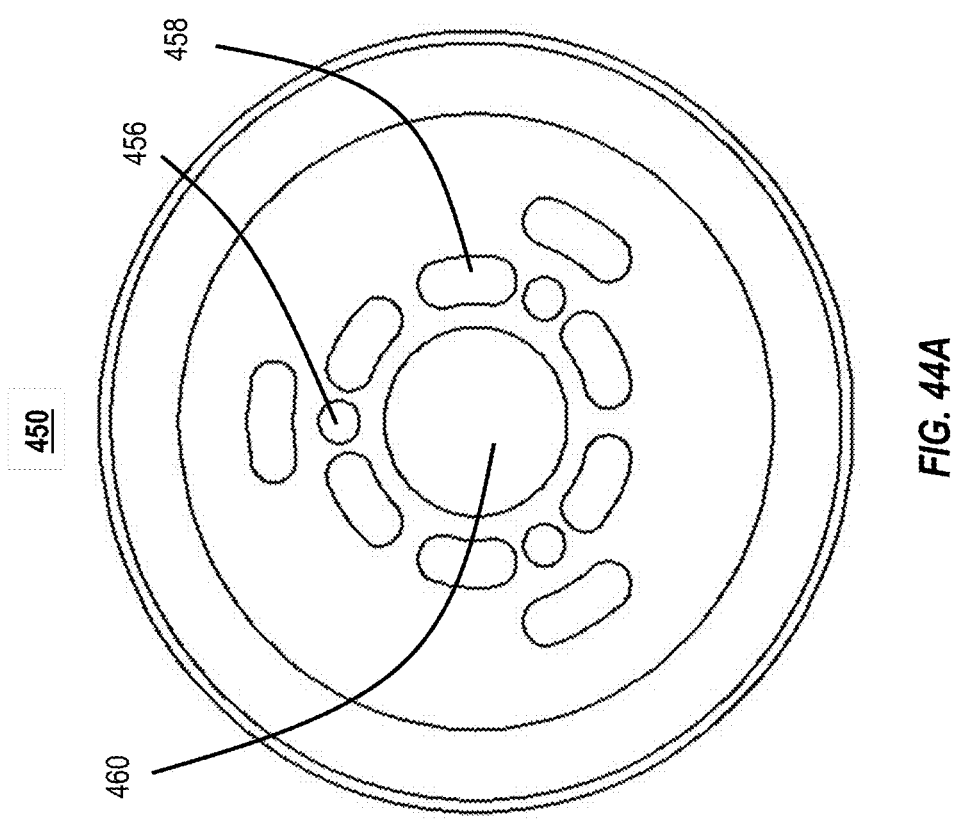

FIGS. 44A and 44B illustrate different views of the bottom-side of the burr hole cover cap 450. The burr hole cover cap 450 can include a plurality of alignment guides 458 that are used to align the burr hole cover cap 450 with the lower part 410 before the two components are secured together. The burr hole cover cap 450 can also include a central boss 460 that can be used in the alignment of the two components and to plug the central lumen 411.

Figure 45:
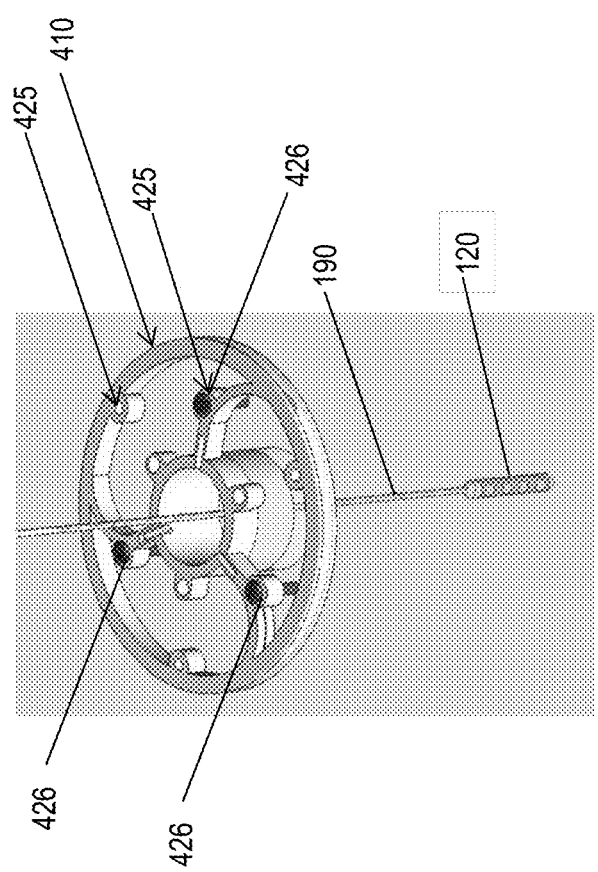
FIGS. 45-47 illustrate the wrapping of the antenna around the lower part of the burr hole cover frame from FIG. 39.
Figure 46:
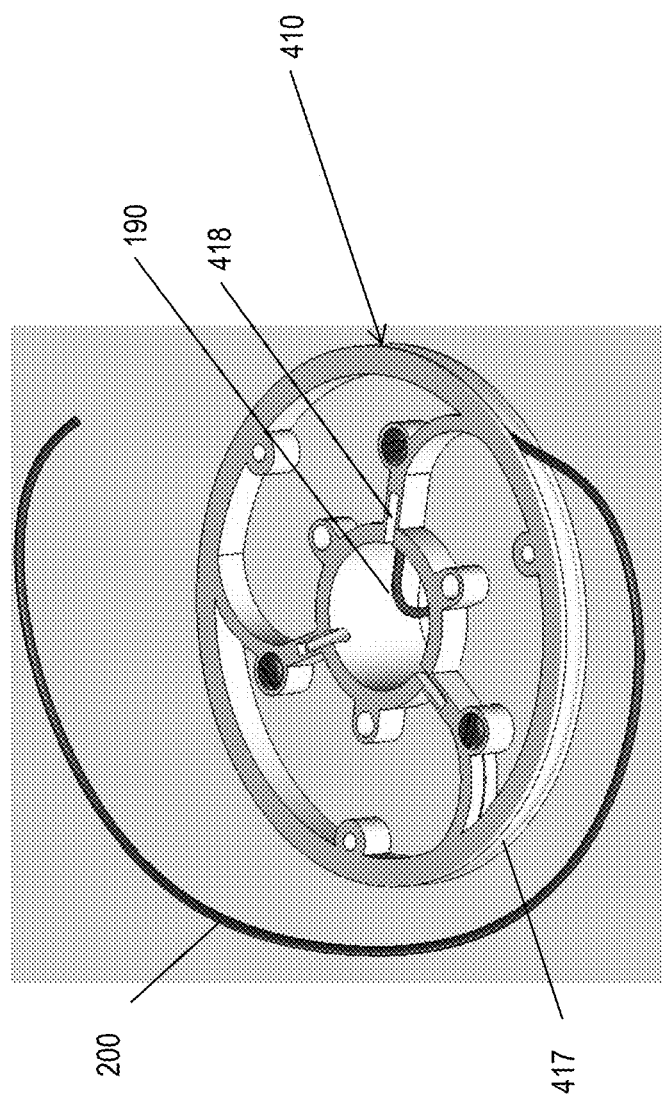
Figure 47:
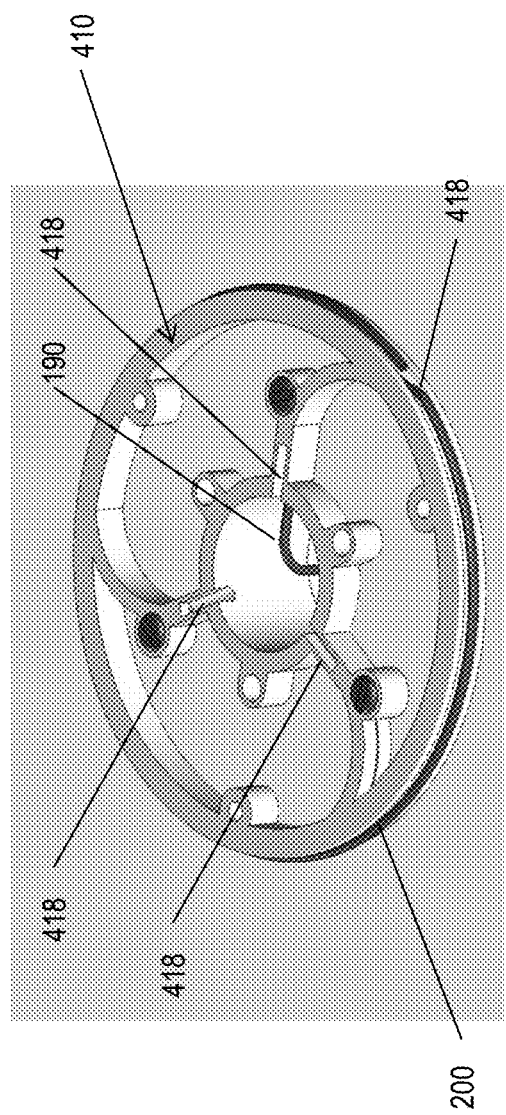

FIGS. 45-47 illustrate the wrapping of the antenna 200 around the lower part 410. FIG. 45 illustrates the lower part 410 and the leadless stimulator 100 after implantation. The leadless stimulator 100 is implanted into the patient's brain and the lower part 410 has been inserted into the craniotomy. The tether 190 is coupled with the stimulation capsule 120 and extends through the central lumen 411 and transitions into the antenna 200.

FIG. 46 illustrates the insertion of antenna 200 into the hole 418. The hole 418 begins in the central lumen 411 and traverses through one of the spokes of the lower part 410 to the antenna notch 417.

As illustrated in FIG. 47, the antenna 200 can then be wrapped around the lower part 410 in the antenna notch 417. Wrapping the antenna 200 around lower part 410 can ensure that the antenna 200 forms a loop of proper diameter to increase the effectiveness of the antenna 200. In some implementations, the antenna 200 can be secured to the lower part 410 with a clip or with a bonding agent. In some implementations, the proximal end of the antenna 200 includes a loop, which can be stretched over the perimeter of the cartwheel frame 415 and into the antenna notch 417.

Deep Brain Stimulation can relieve the symptoms of Movement Disorders. The systems and methods described herein provide a more efficient and simple device to deliver the required therapeutic stimulation and in some cases provide neural recording. In the case of Movement Disorders the systems and methods described herein can provide efficient stimulation of the sub-thalamic nucleus, the Globus Pallidus interna, the Globus Pallidus externus, the Zone Incerta, or the Ventral Intermediate Nucleus to relieve symptoms such as rigidity and tremor. In other therapeutic domains such as psychiatric diseases, the systems and devices described herein can be implanted in the Cingulate Gyrus 25, the Medial Forebrain Bundle, the Nucleus Accumbens, the Ventral Striatum to deliver electrical stimulation and relieve the symptoms of Depression, Anxiety, Phobias, Obsessive Compulsive Disorder, or Post Traumatic Stress Disorder.

In some implementations, the leadless stimulator 100 can be implanted into anatomy of the patient other than the brain. For example, the leadless stimulator 100 may be used for pain management, spasticity, movement disorders, and spinal cord injury. In some of these implementations, the leadless stimulator 100 can be implanted near the patient's spinal cord. FIG. 48A demonstrates a representative human anatomy of the spinal column 4800. There are a series of vertebrae 4820 separated by intervertebral discs 4830. The spinal cord 4840 is also represented in the spinal canal 4845. FIG. 48B illustrates a magnified section of the anatomy 4800 demonstrating the same anatomical sections with greater detail.

Figure 48D:
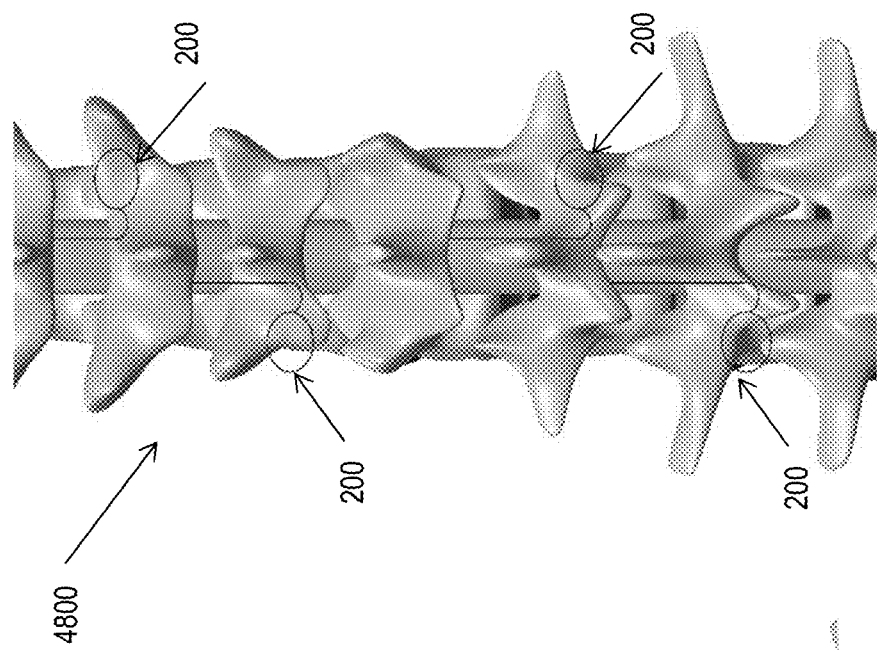
Figure 48C:
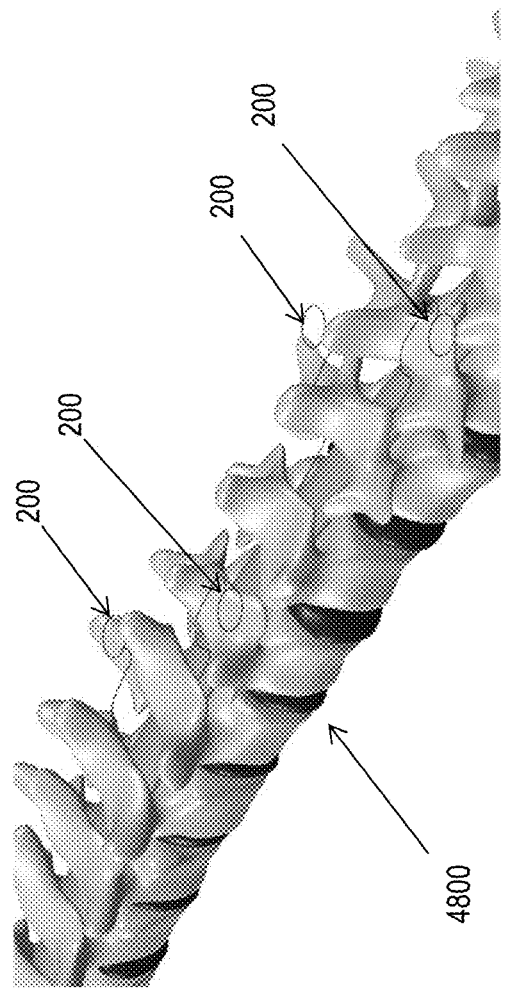
Figure 48E:
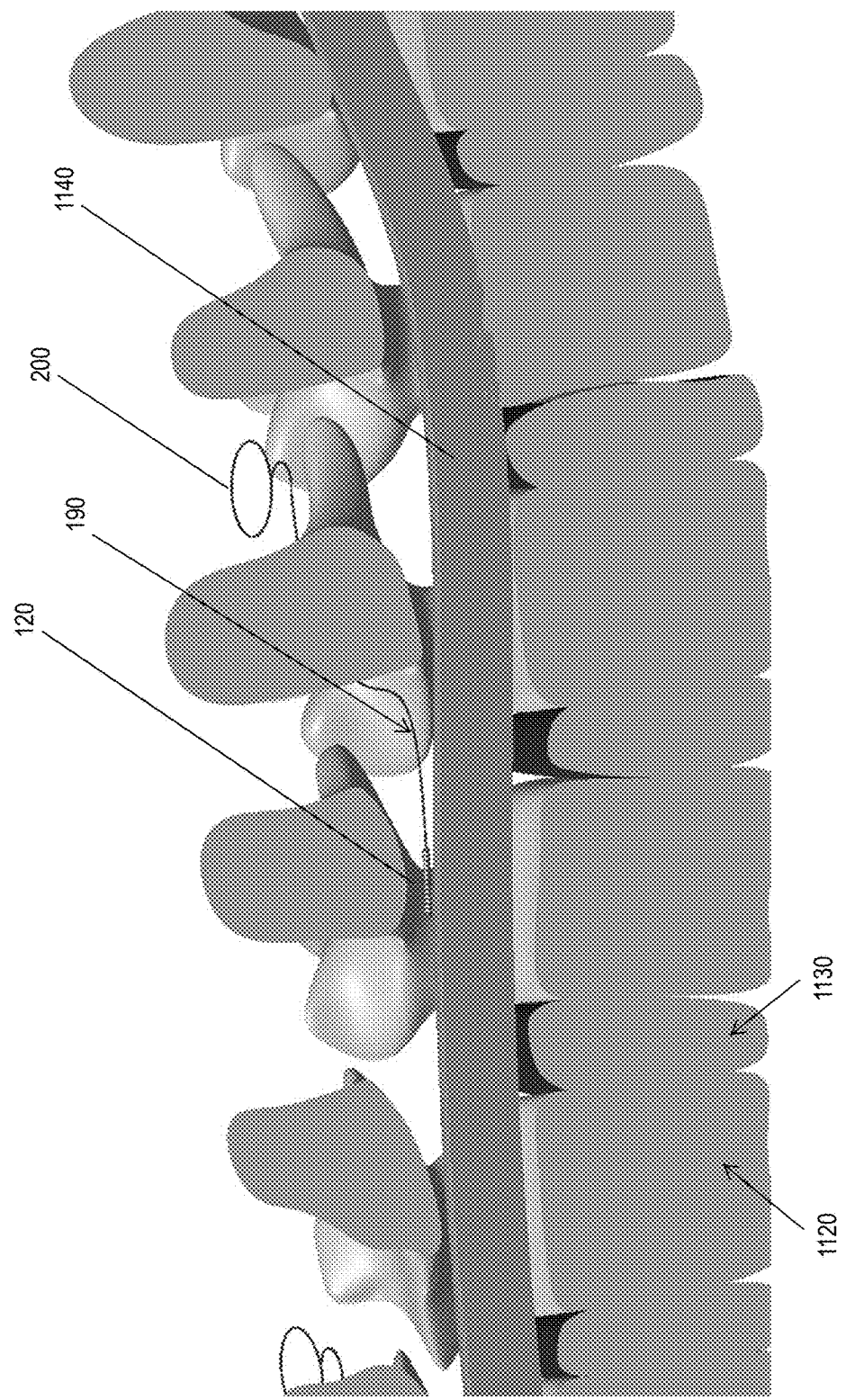

FIG. 48C illustrates a perspective view of the anatomy 4800 with four implanted stimulation capsules 120. The implantable antennas 200 remain outside of the epidural space, while the distal ends have been implanted on the surface of the spinal cord. FIG. 48D demonstrates the same surgical position from a different viewpoint angle. FIG. 48E illustrates a side, cut-away view of the patient's spinal cord. The stimulation capsule 120 is implanted dorsal to the spinal cord 1140, vertebrae 1120, and the intervertebral discs 1130.

Figure 49:
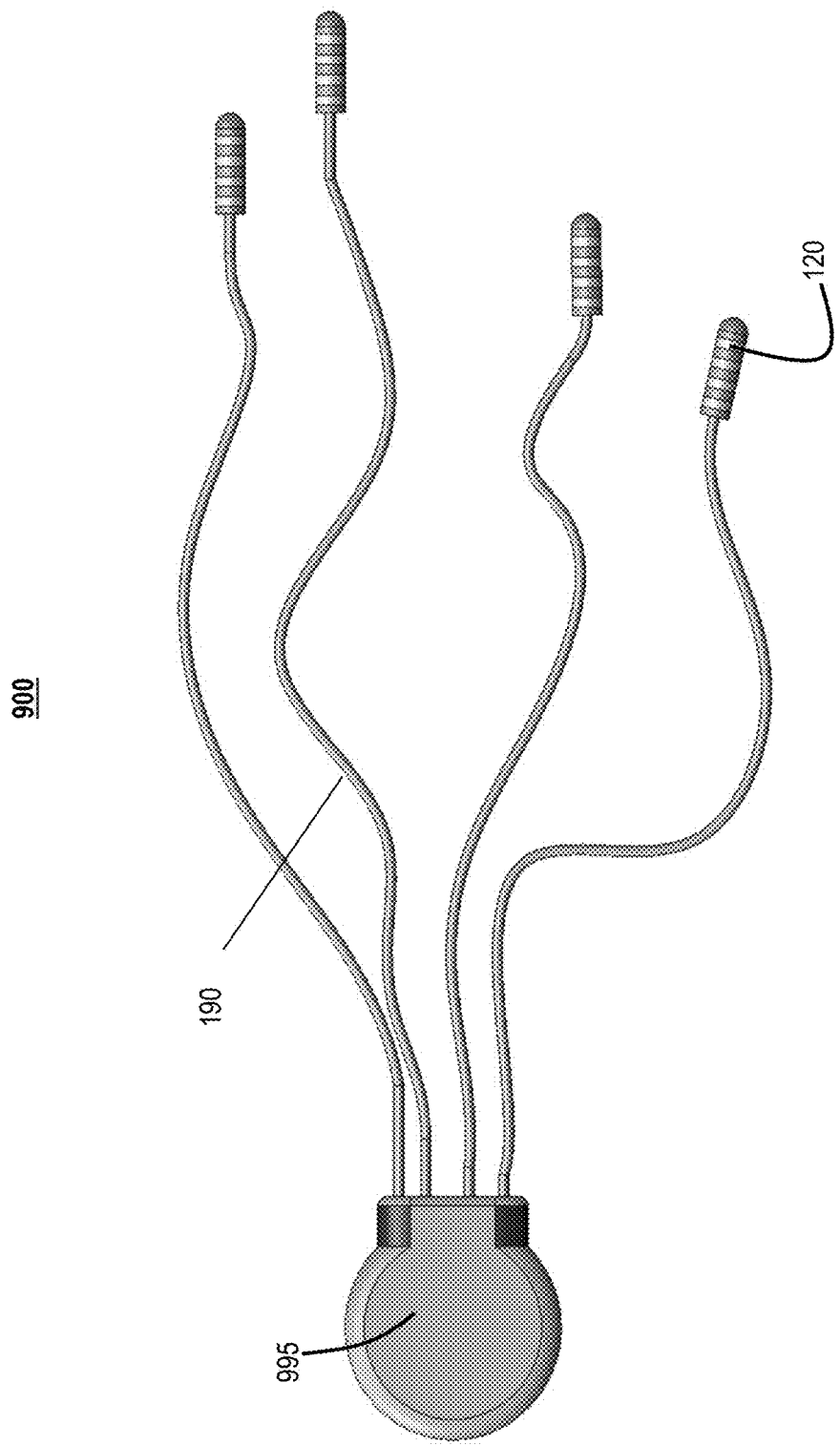
FIG. 49 illustrates an example distributed stimulator.

FIG. 49 illustrates an example distributed stimulator 900. In some implementations, a plurality of leadless stimulators 100 can be implanted into a patient, and in other implementations a distributed stimulator 900 can be implanted into the patient. The distributed stimulator 900 includes a plurality of stimulation capsules 120 (four as illustrated in FIG. 49) that can act in unison or similar to a plurality of independently implanted stimulation capsules 120. The stimulation capsules 120 are coupled to a central control device 995, which can include central antenna for the plurality of stimulation capsules 120. Each of the stimulation capsules 120 are coupled to the central control device 995 by a tether 190. As illustrated, the stimulation capsule 120 includes a plurality of ring electrodes around the circumference of each stimulation capsule 120.

Figure 50:
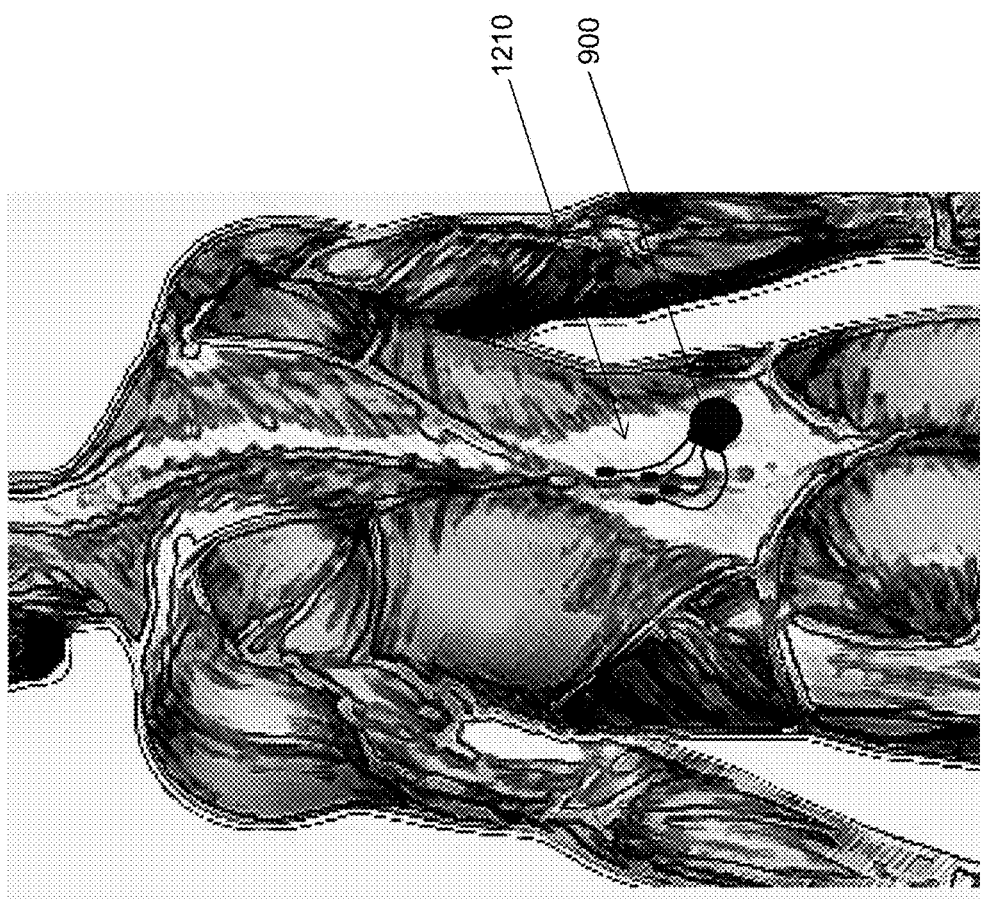
FIG. 50 illustrates the example distributed stimulator of FIG. 49 implanted into a patient.

FIG. 50 illustrates the example distributed stimulator 900 implanted into a patient. The distributed stimulator 900 is implanted into the lumbar region 1210 of the patient. The distributed stimulator 900 has been implanted in a region that permits the distributed distal capsules to cover a region which would be advantageous to the surgical procedure, for example, the placement of the stimulation capsules 120 near the patient's spinal column as illustrated in FIG. 48E.

Various implementations of the microelectrode device have been described herein. These embodiments are giving by way of example and not to limit the scope of the present disclosure. The various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the disclosure.

Devices described herein as either acute or chronic may be used acutely or chronically. They may be implanted for such periods, such as during a surgery, and then removed. They may be implanted for extended periods, or indefinitely. Any devices described herein as being chronic may also be used acutely.

The present disclosure is not to be limited in terms of the particular embodiments described in this application, which are intended as illustrations of various aspects. Modifications and variations can be made without departing from its spirit and scope of this disclosure. Functionally equivalent methods and apparatuses may exist within the scope of this disclosure. Such modifications and variations are intended to fall within the scope of the appended claims. The subject matter of the present disclosure includes the full scope of equivalents to which it is entitled. This disclosure is not limited to particular methods, reagents, compounds compositions or biological systems, which can vary. The terminology used herein is for the purpose of describing particular embodiments, and is not intended to be limiting.

With respect to the use of substantially any plural or singular terms herein, the plural can include the singular or the singular can include the plural as is appropriate to the context or application.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Claims directed toward the described subject matter may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, such recitation can mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction would include but not be limited to systems that have A alone, B alone, C alone, A and B together, A and C together, B and C together, and/or A, B, and C together, etc.). Any disjunctive word or phrase presenting two or more alternative terms, whether in the description, claims, or drawings, can contemplate the possibilities of including one of the terms, either of the terms, or both terms. For example, the phrase "A or B" includes the possibilities of "A" or "B" or "A and B."

In addition, where features or aspects of the disclosure are described in terms of Markush groups, the disclosure is also described in terms of any individual member or subgroup of members of the Markush group.

Any ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. Language such as "up to," "at least," "greater than," "less than," and the like include the number recited and refer to ranges which can be subsequently broken down into subranges as discussed above. Finally, a range includes each individual member.

One or more or any part thereof of the techniques described herein can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program can be stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis, preprocessing, and other methods described herein can also be implemented as a computer-readable storage medium, configured with a computer program, where the storage medium so configured causes a computer to operate in a specific and predefined manner to perform the functions described herein. In some embodiments, the computer readable media is tangible and substantially non-transitory in nature, e.g., such that the recorded information is recorded in a form other than solely as a propagating signal.

In some embodiments, a program product may include a signal bearing medium. The signal bearing medium may include one or more instructions that, when executed by, for example, a processor, may provide the functionality described above. In some implementations, signal bearing medium may encompass a computer-readable medium, such as, but not limited to, a hard disk drive, a Compact Disc (CD), a Digital Video Disk (DVD), a digital tape, memory, etc. In some implementations, the signal bearing medium may encompass a recordable medium, such as, but not limited to, memory, read/write (R/W) CDs, R/W DVDs, etc. In some implementations, signal bearing medium may encompass a communications medium such as, but not limited to, a digital or an analog communication medium (e.g., a fiber optic cable, a waveguide, a wired communications link, a wireless communication link, etc.). Thus, for example, the program product may be conveyed by an RF signal bearing medium, where the signal bearing medium is conveyed by a wireless communications medium (e.g., a wireless communications medium conforming with the IEEE 802.11 standard).

Any of the signals and signal processing techniques may be digital or analog in nature, or combinations thereof.

While certain embodiments of this disclosure have been particularly shown and described with references to preferred embodiments thereof, various changes in form and details may be made therein without departing from the scope of the disclosure.

The invention claimed is:

1. A neurostimulation device, comprising:
a capsule body comprising a proximal and a distal end;
a MEMS film formed to define a lumen, the MEMS film comprising an exterior portion coupled with the capsule body, a plurality of electrodes, and a contact pad;
an antenna coupled with the MEMS film and configured to receive signals from an external programmer;
a stimulation source coupled with the contact pad of the MEMS film and disposed within the lumen and in electrical communication with at least one of the plurality of electrodes; and
a power supply coupled with the contact pad of the MEMS film and disposed within the lumen and in electrical communication with the stimulation source.

2. The device of claim 1, wherein the MEMS film further comprises the antenna.

3. The device of claim 1, wherein the antenna is a strip antenna or a serpentine antenna.

4. The device of claim 1, comprising:
a tether coupled with the distal end of the capsule body, the tether comprising the antenna.

5. The device of claim 1, wherein the antenna is configured to operate at a center frequency of one of 6.790 MHz, 13.560 MHz, 27.120 MHz, 40.680 MHz, 433.920 MHz, 915.000 MHz, 2.450 GHz, 5.800 GHz, and 24.125 GHz.

6. The device of claim 1, wherein the antenna forms a loop around a burr hole cover frame.

7. The device of claim 1, wherein the antenna comprises one or more wires in electrical communication with the stimulation capsule.

8. The device of claim 7, wherein the one or more wires are each coupled with a wire tether contact disposed on the contact pad.

9. The device of claim 1, comprising:
a ribbon cable coupled between the exterior portion and the contact pad, wherein the ribbon cable extends from a distal end of the MEMS film into the lumen.

10. The device of claim 1, wherein a diameter of the stimulation capsule is less than a diameter of the tether.

11. The device of claim 1, comprising a recording circuit coupled with the contact pad of the MEMS film and disposed in the lumen, the recording circuit in electrical communication with a portion of the plurality of electrodes.

12. The device of claim 1, wherein the power supply is a battery or super-capacitor.

13. The device of claim 1, wherein the MEMS film comprises a first polymeric layer, a first barrier layer, a metal layer, a second barrier layer, and a second polymeric layer.

14. The device of claim 1, wherein the lumen defined by the MEMS film is backfilled with a polymer precursor to form the capsule body.

15. A method, comprising:
  implanting, with a guide tube, a neurostimulation device near a target area, the neurostimulation device comprising:
    a capsule body comprising a proximal and a distal end;
    a MEMS film formed to define a lumen, the MEMS film comprising an exterior portion coupled with the capsule body, a plurality of electrodes, and a contact pad;
    an antenna coupled with the MEMS film and configured to receive signals from an external programmer;
    a stimulation source coupled with the contact pad of the MEMS film and disposed within the lumen and in electrical communication with at least one of the plurality of electrodes; and
    a power supply coupled with the contact pad of the MEMS film and disposed within the lumen and in electrical communication with the stimulation source;
  retracting the guide tube;
  generating, by the stimulation source, a stimulation signal; and
  stimulating, via at least one of the plurality of electrodes, the target area with the stimulation signal.

16. The method of claim 15, comprising:
  wirelessly recharging, via the antenna, the power supply.

17. The method of claim 15, wherein the MEMS film further comprises the antenna.

18. The method of claim 15, comprising:
  retracting from the target area, by a tether coupled with the neurostimulation device, the neurostimulation device.

19. The method of claim 15, comprising:
  programming, wirelessly via the antenna, a stimulation parameter of the neurostimulation device.

20. The method of claim 15, comprising:
  receiving, wirelessly via the antenna, recorded physiological data from the neurostimulation device.

* * * * *